United States Patent
Clarke et al.

(10) Patent No.: US 9,828,388 B2
(45) Date of Patent: Nov. 28, 2017

(54) THIENO[3,2-D]PYRIMIDINE, FURO[3,2-D]PYRIMIDINE, AND PYRROLO[3,2-D]PYRIMIDINES USEFUL FOR TREATING RESPIRATORY SYNCITIAL VIRUS INFECTIONS

(71) Applicant: Gilead Sciences, Inc., Foster City, CA (US)

(72) Inventors: Michael O'Neil Hanrahan Clarke, Redwood City, CA (US); Richard L. Mackman, Millbrae, CA (US); Dustin Siegel, San Carlos, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 14/806,227

(22) Filed: Jul. 22, 2015

(65) Prior Publication Data
US 2016/0024107 A1    Jan. 28, 2016

Related U.S. Application Data

(60) Provisional application No. 62/029,896, filed on Jul. 28, 2014.

(51) Int. Cl.
| | | |
|---|---|---|
| *C07H 7/06* | (2006.01) | |
| *C07H 11/04* | (2006.01) | |
| *C07D 495/04* | (2006.01) | |

(52) U.S. Cl.
CPC ............ *C07D 495/04* (2013.01); *C07H 7/06* (2013.01); *C07H 11/04* (2013.01)

(58) Field of Classification Search
None
See application file for complete search history.

(56) References Cited

U.S. PATENT DOCUMENTS

2010/0234584 A1* 9/2010 Chang ................... C07H 19/06
536/27.11

FOREIGN PATENT DOCUMENTS

| EP | 2615101 A1 | 7/2013 |
|---|---|---|
| WO | WO2008/141079 | * 11/2008 |
| WO | WO-2008/141079 A1 | 11/2008 |
| WO | WO-2009/132135 A1 | 10/2009 |
| WO | WO-2012/039791 A1 | 3/2012 |
| WO | WO-2012/040124 A1 | 3/2012 |
| WO | WO-2015/069939 A1 | 5/2015 |

OTHER PUBLICATIONS

Clarke, Mo., et al., (2015), "Discovery of β-D-2'-deoxy-2'-a-fluoro-4'-a-cyano-5-aza-7,9-dideaza adenosine as a potent nucleoside inhibitor of respiratory syncytial virus with excellent selectivity over mitochondrial RNA and DNA polymerases", Bioorg Med Chem Lett, 25:2484-7.
ISR and Written Opinion for PCT/US2015/041574 with mail date of Oct. 19, 2015, 13pgs.
IPRP for PCT/US2015/041574, dated Feb. 9, 2017, 8pgs.

* cited by examiner

*Primary Examiner* — Traviss C McIntosh, III

(57) ABSTRACT

Provided herein are formulations, methods and substituted thieno[3,2-d]pyrimidine, furo[3,2-d]pyrimidine, and pyrrolo[3,2-d]pyrimidine compounds of Formula (I) for treating Pneumovirinae virus infections, including respiratory syncytial virus infections, as well as methods and intermediates for synthesis of substituted thieno[3,2-d]pyrimidine, furo[3,2-d]pyrimidine, and pyrrolo[3,2-d]pyrimidine compounds.

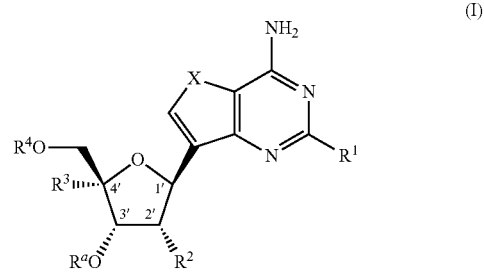

28 Claims, No Drawings

THIENO[3,2-D]PYRIMIDINE, FURO[3,2-D]PYRIMIDINE, AND PYRROLO[3,2-D]PYRIMIDINES USEFUL FOR TREATING RESPIRATORY SYNCITIAL VIRUS INFECTIONS

CROSS REFERENCE TO RELATED APPLICATIONS

This application claims priority to and the benefit of U.S. Provisional Application No. 62/029,896, filed Jul. 28, 2014, which is hereby incorporated by reference in its entirety.

FIELD

Provided herein are substituted thieno[3,2-d]pyrimidine, furo[3,2-d]pyrimidine, and pyrrolo[3,2-d]pyrimidine compounds, methods and pharmaceutical formulations for treating Pneumovirinae virus infections, particularly including respiratory syncytial virus infections, and methods and intermediates useful for preparing the compounds.

BACKGROUND

Pneumovirinae viruses are negative-sense, single-stranded, RNA viruses that are responsible for many prevalent human and animal diseases. The Pneumovirinae subfamily of viruses is a part of the family Paramyxoviridae and includes human respiratory syncytial virus (HRSV). Almost all children will have had an HRSV infection by their second birthday. HRSV is the major cause of lower respiratory tract infections in infancy and childhood with 0.5% to 2% of those infected requiring hospitalization. The elderly and adults with chronic heart, lung disease or those that are immunosuppressed also have a high risk for developing severe HRSV disease (http://www.cdc.gov/rsv/index.html). No vaccine to prevent HRSV infection is currently available. The monoclonal antibody palivizumab is available for immunoprophylaxis, but its use is restricted to infants at high risk, e.g., premature infants or those with either congenital heart or lung disease, and the cost for general use is often prohibitive. In addition, nucleoside analog ribavirin has been approved as the only antiviral agent to treat HRSV infections but has limited efficacy. Therefore, there is a need for anti-Pneumovirinae therapeutics.

Examples of pyrrolo[2,3-d]pyrimidine compounds useful for treating viral infections are described in U.S. 2012/0009147 A1 (Cho et al.), U.S. 2012/0020921 A1 (Cho et al.), WO 2008/089105 A2 (Babu et al.), WO 2008/141079 A1 (Babu et al.), WO 2009/132135 A1 (Butler et al.), WO 2010/002877 A2 (Francom), WO 2011/035231 A1 (Cho et al.), WO 2011/035250 A1 (Butler et al.), WO 2011/150288 A1 (Cho et al.), WO 2012/012465 (Cho et al.), WO 2012/012776 A1 (Mackman et al.), WO 2012/037038 (Clarke et al.), WO 2012/087596 A1 (Delaney et al.), and WO 2012/142075 A1 (Girijavallabhan et al.).

There remains a need for new antiviral agents useful in treating Paramyxoviridae viral infections, including Pneumovirinae viral infections, such as HRSV infections, that are effective and have acceptable toxicity profiles.

SUMMARY

Provided are compounds, methods, and pharmaceutical formulations for the treatment of infections caused by the Pneumovirinae virus family, including treatment of infections caused by human respiratory syncytial virus.

Provided is a compound of Formula (I), or a pharmaceutically acceptable salt thereof:

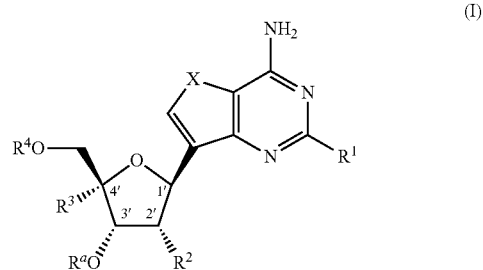

wherein:
X is selected from the group of O, S, NH, or $N(C_1-C_6$ alkyl);
$R^1$ is selected from the group of H, $CH_3$, $CH_3$, F, Cl, and $NH_2$;
$R^2$ is selected from the group of F, Cl, $OR^a$, $NHR^a$, CN, and $N_3$;
$R^3$ is selected from the group of CN, $OR^a$, $C_1-C_6$ alkyl, $C_2-C_6$ alkenyl, $C_2-C_6$ alkynyl, —$CH_2$—O—$C_1-C_6$ alkyl, —$CH_2$—S—$C_1-C_6$ alkyl, $C_3-C_4$ cycloalkyl, azido, halogen, $C_1-C_3$ haloalkyl, $SR^a$, —$CH_2$—$C_3-C_4$ cycloalkyl, —O—$C_3$—C $R^3$ is selected from the group of CN, $OR^a$, $C_1-C_6$ alkyl, $C_2-C_6$ alkenyl, $C_2-C_6$ alkynyl, —$CH_2$—O—$C_1-C_6$ alkyl, —$CH_2$—S—$C_1-C_6$ alkyl, $C_3-C_4$ cycloalkyl, azido, halogen, $C_1-C_3$ haloalkyl, $SR^a$, —$CH_2$—$C_3-C_4$ cycloalkyl, —O—$C_3-C_4$ cycloalkyl, and —O—$C_1-C_3$ haloalkyl;
or
when $R^2$ is $OR^a$, the two ORa groups at the 2' and 3' positions together may form with the furanyl ring to which they are bound a structure selected from the group of:

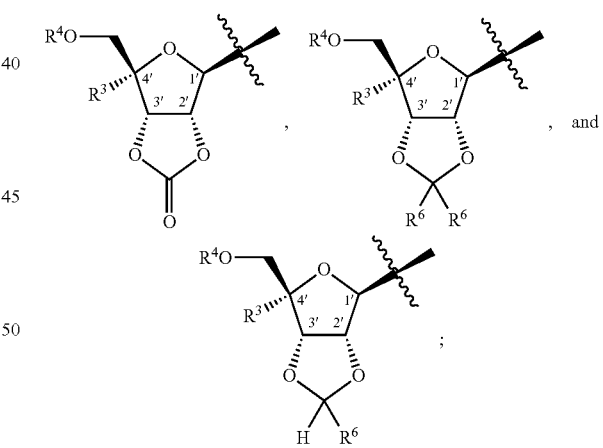

$R^4$ is selected from the group of H, —C(=O)$R^6$, —C(=O)O$R^6$, and —C(=O)N$R^6R^7$;
or
a) $R^4$ is a group of the formula:

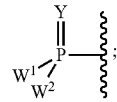

wherein:

each Y is O, S, NR, $^+$N(O)(R), N(OR), $^+$N(O)(OR), or N—NR$_2$; and

W$^1$ and W$^2$, when taken together, are —Y$^3$(C(R$^y$)$_2$)$_3$Y$^3$—;

or one of W$^1$ or W$^2$ together with the 3' hydroxy group is —Y$^3$— and the other of W$^1$ or W$^2$ is Formula Ia;

or W$^1$ and W$^2$ are each, independently, a group of the Formula Ia:

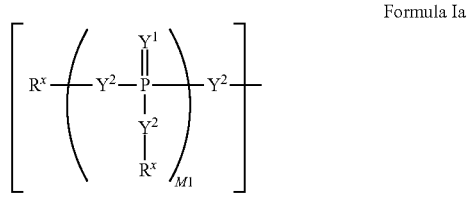

Formula Ia wherein:

each Y$^1$ is, independently, O, S, NR, $^+$N(O)(R), N(OR), $^+$N(O)(OR), or N—NR$_2$;

each Y$^2$ is independently a bond, O, CR$_2$, —O—CR$_2$—, NR, $^+$N(O)(R), N(OR), $^+$N(O)(OR), N—NR$_2$, S, S—S, S(O), or S(O)$_2$;

each Y$^3$ is independently O, S, or NR;

M1 is 0, 1, 2, or 3;

each R$^x$ is independently R$^y$ or the formula:

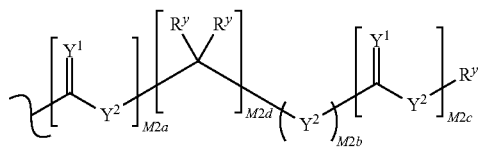

wherein:

each M2a, M2b, and M2c is independently 0 or 1;

M2d is 0, 1, 2, 3, 4, 5, 6, 7, 8, 9, 10, 11 or 12;

each R$^y$ is independently H, F, Cl, Br, I, OH, R, —C(=Y$^1$)R, —C(=Y$^1$)OR, —C(=Y$^1$)N(R)$_2$, —N(R)$_2$, —$^+$N(R)$_3$, —SR, —S(O)R, —S(O)$_2$R, —S(O)(OR), —S(O)$_2$(OR), —OC(=Y$^1$)R, —OC(=Y$^1$)OR, —OC(=Y$^1$)(N(R)$_2$), —SC(=Y$^1$)R, —SC(=Y$^1$)OR, —SC(=Y$^1$)(N(R)$_2$), —N(R)C(=Y$^1$)R, —N(R)C(=Y$^1$)OR, —N(R)C(=Y$^1$)N(R)$_2$, —SO$_2$NR$_2$, —CN, —N$_3$, —NO$_2$, —OR, or W$^3$;

or when taken together, two R$^y$ on the same carbon atom form a carbocyclic ring having 3, 4, 5, 6, or 7 carbon ring atoms;

or when taken together, two R$^y$ on the same carbon atom form along with the carbon atom a heterocycle having 3, 4, 5, 6, or 7 ring atoms wherein one ring atom is selected from 0 or N and all other ring atoms are carbon;

each R is independently H, (C$_1$-C$_8$)alkyl, (C$_1$-C$_8$) substituted alkyl, (C$_2$-C$_8$)alkenyl, (C$_2$-C$_8$) substituted alkenyl, (C$_2$-C$_8$)alkynyl, (C$_2$-C$_8$) substituted alkynyl, C$_6$-C$_{10}$ aryl, C$_6$-C$_{10}$ substituted aryl, a 3- to 10-membered heterocycle, a substituted 3- to 10-membered heterocycle, a 5- to 12-membered heteroaryl, a substituted 5- to 12-membered heteroaryl, arylalkyl, substituted arylalkyl, heteroarylalkyl, or substituted heteroarylalkyl; and W$^3$ is W$^4$ or W$^5$;

W$^4$ is R, —C(Y$^1$)R$^y$, —C(Y$^1$)W$^5$, —SO$_2$R$^y$, or —SO$_2$W$^5$;

W$^5$ is selected from phenyl, naphthyl, a C$_3$-C$_8$ carbocycle, or a 3- to 10-membered heterocycle, wherein W$^5$ is independently substituted with 0, 1, 2, 3, 4, 5, or 6 R$^y$ groups;

each R$^6$ and R$^7$ is independently H, (C$_1$-C$_8$)alkyl, (C$_2$-C$_8$)alkenyl, (C$_2$-C$_8$)alkynyl, (C$_4$-C$_8$)carbocyclylalkyl, C$_6$-C$_{10}$ aryl, C$_6$-C$_{10}$ substituted aryl, 5- to 10-membered heteroaryl, substituted 5- to 10-membered heteroaryl, —C(=O)(C$_1$-C$_8$)alkyl, —S(O)$_n$(C$_1$-C$_8$)alkyl or aryl(C$_1$-C$_8$)alkyl;

or R$^6$ and R$^7$ taken together with a nitrogen to which they are both attached form a 3- to 7-membered heterocycle wherein any one ring carbon atom of said heterocycle can optionally be replaced with —O—, —S— or —NR$^a$—;

and wherein each (C$_1$-C$_8$)alkyl, (C$_2$-C$_8$)alkenyl, (C$_2$-C$_8$)alkynyl or aryl(C$_1$-C$_8$)alkyl of each R$^6$ or R$^7$ is, independently, optionally substituted with one, two, three, or four substituents selected from halo, hydroxy, CN, N$_3$, N(R$^a$)$_2$ or OR$^a$; and wherein one, two, or three of the non-terminal carbon atoms of each said (C$_1$-C$_8$)alkyl may be optionally replaced with —O—, —S— or —NR$^a$—; or b) R$^4$ is a group selected from:

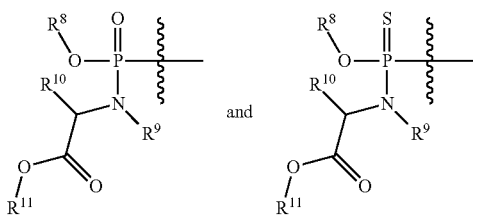

wherein:

R$^8$ is selected from phenyl, 1-naphthyl, 2-naphthyl,

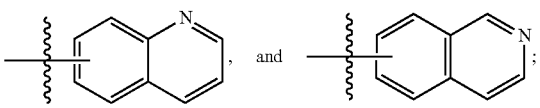

R$^9$ is selected from H and CH$_3$;

R$^{10}$ is selected from H or C$_1$-C$_6$ alkyl; and

R$^{11}$ is selected from H, C$_1$-C$_8$ alkyl, benzyl, C$_3$-C$_6$ cycloalkyl, and —CH$_2$—C$_3$-C$_6$ cycloalkyl; or c) R$^4$ and the 3' hydroxy group combine to form the structure selected from:

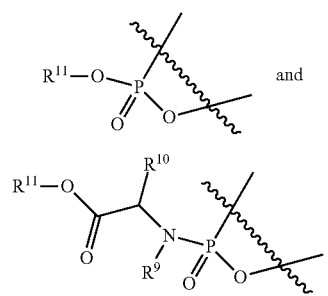

DETAILED DESCRIPTION

Provided is a compound of Formula (I), or a pharmaceutically acceptable salt thereof, wherein X is S and $R^a$, $R^1$, $R^2$, $R^3$, $R^4$, $R^5$, $R^6$, $R^7$, $R^8$, $R^9$, $R^{10}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$ are as defined above for Formula (I).

Provided is a compound of Formula (I), or a pharmaceutically acceptable salt thereof, wherein X is O and $R^a$, $R^1$, $R^2$, $R^3$, $R^4$, $R^5$, $R^6$, $R^7$, $R^8$, $R^9$, $R^{10}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$ are as defined above for Formula (I).

Provided is a compound of Formula (I), or a pharmaceutically acceptable salt thereof, wherein X is NH or $N(C_1-C_6$ alkyl) and $R^a$, $R^1$, $R^2$, $R^3$, $R^4$, $R^5$, $R^6$, $R^7$, $R^8$, $R^9$, $R^{10}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$ are as defined above for Formula (I).

Provided within each of the embodiments is a further embodiment comprising a compound of the embodiment, or a pharmaceutically acceptable salt thereof wherein $R^3$ is selected from the group of CN, $OR^a$, $C_1-C_4$ alkyl, $C_2-C_4$ alkenyl, $C_2-C_4$ alkynyl, —$CH_2$—O—$C_1-C_4$ alkyl, —$CH_2$—S—$C_1-C_4$ alkyl, $C_3-C_4$ cycloalkyl, azido, halogen, $C_1-C_3$ chloroalkyl, $C_1-C_3$ bromoalkyl, and $C_1-C_3$ fluoroalkyl; and all other variables, including X, $R^a$, $R^1$, $R^2$, $R^4$, $R^5$, $R^6$, $R^7$, $R^8$, $R^9$, $R^{10}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$, are as defined above for the embodiment.

Also provided within each of the embodiments is a further embodiment comprising a compound of the embodiment, or a pharmaceutically acceptable salt thereof wherein $R^3$ is selected from the group of CN, $OR^a$, $C_1-C_3$ alkyl, $C_2-C_3$ alkenyl, $C_2-C_3$ alkynyl, —$CH_2$—O—$C_1-C_3$ alkyl, —$CH_2$—S—$C_1-C_3$ alkyl, $C_3-C_4$ cycloalkyl, azido, halogen, $C_1-C_3$ chloroalkyl, $C_1-C_3$ bromoalkyl, and $C_1-C_3$ fluoroalkyl; and all other variables, including X, $R^a$, $R^1$, $R^2$, $R^4$, $R^5$, $R^6$, $R^7$, $R^8$, $R^9$, $R^{10}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$, are as defined above for the embodiment.

Also provided is a compound of Formula (I), or a pharmaceutically acceptable salt thereof, wherein:
$R^1$ is selected from the group of H, $CH_3$, F, Cl, and $NH_2$;
$R^2$ is selected from the group of OH, F, Cl, $N_3$, $NH_2$, and CN;
$R^3$ is selected from the group of CN, $N_3$, methyl, ethyl, propyl, vinyl, propenyl, ethynyl, $CH_2F$, $CHF_2$, $CH_2Cl$, $CH_2SMe$, and $CH_2OMe$; and
X, $R^a$, $R^4$, $R^5$, $R^6$, $R^7$, $R^8$, $R^9$, $R^{10}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$ are as defined above for Formula (I).

Also provided is a compound of Formula (I), or a pharmaceutically acceptable salt thereof, wherein:
X is S;
$R^1$ is selected from the group of H, $CH_3$, F, Cl, and $NH_2$;
$R^2$ is selected from the group of OH, F, Cl, $N_3$, $NH_2$, and CN;
$R^3$ is selected from the group of CN, $N_3$, methyl, ethyl, propyl, vinyl, propenyl, ethynyl, $CH_2F$, $CHF_2$, $CH_2Cl$, $CH_2SMe$, and $CH_2OMe$; and
$R^a$, $R^4$, $R^5$, $R^6$, $R^7$, $R^8$, $R^9$, $R^{10}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$ are as defined above for Formula (I).

Also provided is a compound of Formula (I), or a pharmaceutically acceptable salt thereof, wherein:
X is O;
$R^1$ is selected from the group of H, $CH_3$, F, Cl, and $NH_2$;
$R^2$ is selected from the group of OH, F, Cl, $N_3$, $NH_2$, and CN;
$R^3$ is selected from the group of CN, $N_3$, methyl, ethyl, propyl, vinyl, propenyl, ethynyl, $CH_2F$, $CHF_2$, $CH_2Cl$, $CH_2SMe$, and $CH_2OMe$; and
X, $R^a$, $R^4$, $R^5$, $R^6$, $R^7$, $R^8$, $R^9$, $R^{10}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$ are as defined above for Formula (I).

Also provided is a compound of Formula (I), or a pharmaceutically acceptable salt thereof, wherein:
X is NH;
$R^1$ is selected from the group of H, $CH_3$, F, Cl, and $NH_2$;
$R^2$ is selected from the group of OH, F, Cl, $N_3$, $NH_2$, and CN;
$R^3$ is selected from the group of CN, $N_3$, methyl, ethyl, propyl, vinyl, propenyl, ethynyl, $CH_2F$, $CHF_2$, $CH_2Cl$, $CH_2SMe$, and $CH_2OMe$; and
$R^a$, $R^4$, $R^5$, $R^6$, $R^7$, $R^8$, $R^9$, $R^{10}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$ are as defined above for Formula (I).

Another embodiment comprises a compound of Formula (II), or a pharmaceutically acceptable salt thereof:

wherein $R^1$ is selected from the group of H, $CH_3$, F, Cl, and $NH_2$;
$R^2$ is selected from the group of F, Cl, OH, $NH_2$, CN, and $N_3$;
$R^3$ is selected from the group of CN, $N_3$, methyl, ethyl, propyl, vinyl, propenyl, ethynyl, $CH_2F$, $CHF_2$, $CH_2Cl$, $CH_2SMe$, and $CH_2OMe$; and
$R^a$, $R^4$, $R^5$, $R^6$, $R^7$, $R^8$, $R^9$, $R^{10}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$ are as defined above for Formula (I).

An embodiment comprises a compound of Formula (II) wherein $R^1$ is H and $R^2$, $R^3$, and $R^4$ are as defined above, or a pharmaceutically acceptable salt thereof. A further embodiment comprises a compound of Formula (II) wherein $R^1$ is F and $R^2$, $R^3$, and $R^4$ are as defined above, or a pharmaceutically acceptable salt thereof. A further embodiment comprises a compound of Formula (II) wherein $R^1$ is Cl and $R^2$, $R^3$, and $R^4$ are as defined above, or a pharmaceutically acceptable salt thereof. A further embodiment comprises a compound of Formula (II) wherein $R^1$ is $NH_2$ and $R^2$, $R^3$, and $R^4$ are as defined above, or a pharmaceutically acceptable salt thereof.

Another embodiment comprises a compound of Formula (II) wherein $R^1$ is H, $R^2$ is F, and $R^3$ and $R^4$ are as defined above, or a pharmaceutically acceptable salt thereof. A further embodiment comprises a compound of Formula (II) wherein $R^1$ is H, $R^2$ is Cl, and $R^3$ and $R^4$ are as defined above, or a pharmaceutically acceptable salt thereof. Another embodiment comprises a compound of Formula (II)

wherein $R^1$ is H, $R^2$ is OH, and $R^3$ and $R^4$ are as defined above, or a pharmaceutically acceptable salt thereof. Still another embodiment comprises a compound of Formula (II) wherein $R^1$ is H, $R^2$ is $NH_2$, and $R^3$ and $R^4$ are as defined above, or a pharmaceutically acceptable salt thereof. Another embodiment comprises a compound of Formula (II) wherein $R^1$ is H, $R^2$ is $N_3$, and $R^3$ and $R^4$ are as defined above, or a pharmaceutically acceptable salt thereof.

Another embodiment comprises a compound of Formula (II), or a pharmaceutically acceptable salt thereof, wherein $R^1$ is H, $R^2$ is F, $R^3$ is selected from the group of CN and $N_3$, and $R^4$ is as defined above. A further embodiment comprises a compound of Formula (II), or a pharmaceutically acceptable salt thereof, wherein $R^1$ is H, $R^2$ is F, $R^3$ is selected from the group of methyl, ethyl, propyl, vinyl, propenyl, ethynyl and $CH_2OMe$, and $R^4$ is as defined above. A further embodiment comprises a compound of Formula (II), or a pharmaceutically acceptable salt thereof, wherein $R^1$ is H, $R^2$ is F, $R^3$ is selected from the group of methyl, ethyl, and propyl, and $R^4$ is as defined above. Another embodiment comprises a compound of Formula (II), or a pharmaceutically acceptable salt thereof, wherein $R^1$ is H, $R^2$ is F, $R^3$ is selected from the group of vinyl, propenyl, and ethynyl, and $R^4$ is as defined above. Another embodiment comprises a compound of Formula (II), or a pharmaceutically acceptable salt thereof, wherein $R^1$ is H, $R^2$ is F, $R^3$ is selected from the group of $CH_2F$, $CHF_2$, and $CH_2Cl$, and $R^4$ is as defined above.

Another embodiment comprises a compound of Formula (II), or a pharmaceutically acceptable salt thereof, wherein $R^1$ is H, $R^2$ is Cl, $R^3$ is selected from the group of CN and $N_3$, and $R^4$ is as defined above. A further embodiment comprises a compound of Formula (II), or a pharmaceutically acceptable salt thereof, wherein $R^1$ is H, $R^2$ is Cl, $R^3$ is selected from the group of methyl, ethyl, propyl, vinyl, propenyl, ethynyl and $CH_2OMe$, and $R^4$ is as defined above. A further embodiment comprises a compound of Formula (II), or a pharmaceutically acceptable salt thereof, wherein $R^1$ is H, $R^2$ is Cl, $R^3$ is selected from the group of methyl, ethyl, and propyl, and $R^4$ is as defined above. Another embodiment comprises a compound of Formula (II), or a pharmaceutically acceptable salt thereof, wherein $R^1$ is H, $R^2$ is Cl, $R^3$ is selected from the group of vinyl, propenyl, and ethynyl, and $R^4$ is as defined above. Another embodiment comprises a compound of Formula (II), or a pharmaceutically acceptable salt thereof, wherein $R^1$ is H, $R^2$ is Cl, $R^3$ is selected from the group of $CH_2F$, $CHF_2$, and $CH_2Cl$, and $R^4$ is as defined above.

Another embodiment comprises a compound of Formula (II), or a pharmaceutically acceptable salt thereof, wherein $R^1$ is H, $R^2$ is OH, $R^3$ is selected from the group of CN and $N_3$, and $R^4$ is as defined above. A further embodiment comprises a compound of Formula (II), or a pharmaceutically acceptable salt thereof, wherein $R^1$ is H, $R^2$ is OH, $R^3$ is selected from the group of methyl, ethyl, propyl, vinyl, propenyl, ethynyl and $CH_2OMe$, and $R^4$ is as defined above. A further embodiment comprises a compound of Formula (II), or a pharmaceutically acceptable salt thereof, wherein $R^1$ is H, $R^2$ is OH, $R^3$ is selected from the group of methyl, ethyl, and propyl, and $R^4$ is as defined above. Another embodiment comprises a compound of Formula (II), or a pharmaceutically acceptable salt thereof, wherein $R^1$ is H, $R^2$ is OH, $R^3$ is selected from the group of vinyl, propenyl, and ethynyl, and $R^4$ is as defined above. Another embodiment comprises a compound of Formula (II), or a pharmaceutically acceptable salt thereof, wherein $R^1$ is H, $R^2$ is OH, $R^3$ is selected from the group of $CH_2F$, $CHF_2$, and $CH_2Cl$, and $R^4$ is as defined above.

Another embodiment comprises a compound of Formula (II), or a pharmaceutically acceptable salt thereof, wherein $R^1$ is H, $R^2$ is $NH_2$, $R^3$ is selected from the group of CN and $N_3$, and $R^4$ is as defined above. A further embodiment comprises a compound of Formula (II), or a pharmaceutically acceptable salt thereof, wherein $R^1$ is H, $R^2$ is $NH_2$, $R^3$ is selected from the group of methyl, ethyl, propyl, vinyl, propenyl, ethynyl and $CH_2OMe$, and $R^4$ is as defined above. A further embodiment comprises a compound of Formula (II), or a pharmaceutically acceptable salt thereof, wherein $R^1$ is H, $R^2$ is $NH_2$, $R^3$ is selected from the group of methyl, ethyl, and propyl, and $R^4$ is as defined above. Another embodiment comprises a compound of Formula (II), or a pharmaceutically acceptable salt thereof, wherein $R^1$ is H, $R^2$ is $NH_2$, $R^3$ is selected from the group of vinyl, propenyl, and ethynyl, and $R^4$ is as defined above. Another embodiment comprises a compound of Formula (II), or a pharmaceutically acceptable salt thereof, wherein $R^1$ is H, $R^2$ is $NH_2$, $R^3$ is selected from the group of $CH_2F$, $CHF_2$, and $CH_2Cl$, and $R^4$ is as defined above.

Another embodiment comprises a compound of Formula (II), or a pharmaceutically acceptable salt thereof, wherein $R^1$ is H, $R^2$ is $N_3$, $R^3$ is selected from the group of CN and $N_3$, and $R^4$ is as defined above. A further embodiment comprises a compound of Formula (II), or a pharmaceutically acceptable salt thereof, wherein $R^1$ is H, $R^2$ is $N_3$, $R^3$ is selected from the group of methyl, ethyl, propyl, vinyl, propenyl, ethynyl and $CH_2OMe$, and $R^4$ is as defined above. A further embodiment comprises a compound of Formula (II), or a pharmaceutically acceptable salt thereof, wherein $R^1$ is H, $R^2$ is $N_3$, $R^3$ is selected from the group of methyl, ethyl, and propyl, and $R^4$ is as defined above. Another embodiment comprises a compound of Formula (II), or a pharmaceutically acceptable salt thereof, wherein $R^1$ is H, $R^2$ is $N_3$, $R^3$ is selected from the group of vinyl, propenyl, and ethynyl, and $R^4$ is as defined above. Another embodiment comprises a compound of Formula (II), or a pharmaceutically acceptable salt thereof, wherein $R^1$ is H, $R^2$ is $N_3$, $R^3$ is selected from the group of $CH_2F$, $CHF_2$, and $CH_2Cl$, and $R^4$ is as defined above.

Another embodiment comprises a compound of Formula (III):

wherein:

$R^2$ is F, Cl, OH, $NH_2$, CN, and $N_3$;

$R^3$ is selected from the group of CN, $N_3$, methyl, ethyl, propyl, vinyl, propenyl, ethynyl, $CH_2F$, $CHF_2$, $CH_2Cl$, $CH_2SMe$, and $CH_2OMe$; and $R^4$ is H or group of the formula:

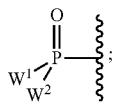

wherein $W^1$ and $W^2$ are each, independently, OH or a group of the Formula Ia:

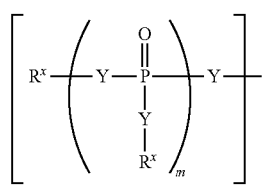

wherein:
each Y is independently a bond or O;
m is 0, 1, 2, or 3;
each $R^x$ is H, halogen or OH;
or
$R^4$ is selected from H and:

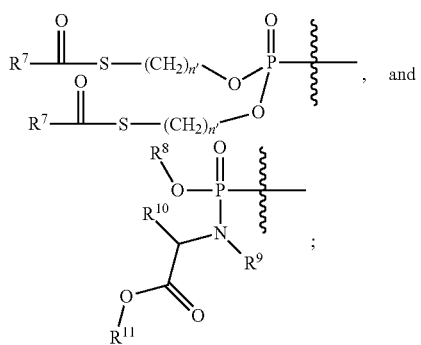

wherein:
n' is selected from the group of 1, 2, 3, and 4;
$R^7$ is selected from the group of $C_1$-$C_8$ alkyl, —O—$C_1$-$C_8$ alkyl, benzyl, —O-benzyl, —$CH_2$—$C_3$-$C_6$ cycloalkyl, —O—$CH_2$—$C_3$-$C_6$ cycloalkyl, and $CF_3$;
$R^8$ is selected from the group of phenyl, 1-naphthyl, 2-naphthyl,

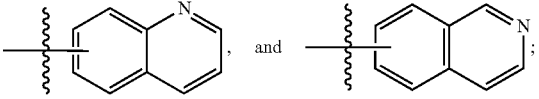

$R^9$ is selected from H and $CH_3$;
$R^{10}$ is selected from H or $C_1$-$C_6$ alkyl;
$R^{11}$ is selected from H, $C_1$-$C_8$ alkyl, benzyl, $C_3$-$C_6$ cycloalkyl, and —$CH_2$—$C_3$-$C_6$ cycloalkyl.

Another embodiment comprises a compound of Formula (III) wherein $R^1$ is H, $R^2$ is F, and $R^3$ and $R^4$ are as defined above, or a pharmaceutically acceptable salt thereof. A further embodiment comprises a compound of Formula (III) wherein $R^2$ is Cl and $R^3$ and $R^4$ are as defined above, or a pharmaceutically acceptable salt thereof. Another embodiment comprises a compound of Formula (III) wherein $R^2$ is OH and $R^3$ and $R^4$ are as defined above, or a pharmaceutically acceptable salt thereof. Still another embodiment comprises a compound of Formula (III) wherein $R^2$ is $NH_2$ and $R^3$ and $R^4$ are as defined above, or a pharmaceutically acceptable salt thereof. Another embodiment comprises a compound of Formula (III) wherein $R^2$ is $N_3$ and $R^3$ and $R^4$ are as defined above, or a pharmaceutically acceptable salt thereof.

Another embodiment comprises a compound of Formula (III), or a pharmaceutically acceptable salt thereof, wherein $R^2$ is F, $R^3$ is selected from the group of CN and $N_3$, and $R^4$ is as defined above. A further embodiment comprises a compound of Formula (III), or a pharmaceutically acceptable salt thereof, wherein $R^2$ is F, $R^3$ is selected from the group of methyl, ethyl, propyl, vinyl, propenyl, ethynyl and $CH_2OMe$, and $R^4$ is as defined above. A further embodiment comprises a compound of Formula (III), or a pharmaceutically acceptable salt thereof, wherein $R^2$ is F, $R^3$ is selected from the group of methyl, ethyl, and propyl, and $R^4$ is as defined above. Another embodiment comprises a compound of Formula (III), or a pharmaceutically acceptable salt thereof, wherein $R^2$ is F, $R^3$ is selected from the group of vinyl, propenyl, and ethynyl, and $R^4$ is as defined above. Another embodiment comprises a compound of Formula (III), or a pharmaceutically acceptable salt thereof, wherein $R^2$ is F, $R^3$ is selected from the group of $CH_2F$, $CHF_2$, and $CH_2Cl$, and $R^4$ is as defined above.

Another embodiment comprises a compound of Formula (III), or a pharmaceutically acceptable salt thereof, wherein $R^2$ is Cl, $R^3$ is selected from the group of CN and $N_3$, and $R^4$ is as defined above. A further embodiment comprises a compound of Formula (III), or a pharmaceutically acceptable salt thereof, wherein $R^2$ is Cl, $R^3$ is selected from the group of methyl, ethyl, propyl, vinyl, propenyl, ethynyl and $CH_2OMe$, and $R^4$ is as defined above. A further embodiment comprises a compound of Formula (III), or a pharmaceutically acceptable salt thereof, wherein $R^2$ is Cl, $R^3$ is selected from the group of methyl, ethyl, and propyl, and $R^4$ is as defined above. Another embodiment comprises a compound of Formula (III), or a pharmaceutically acceptable salt thereof, wherein $R^2$ is Cl, $R^3$ is selected from the group of vinyl, propenyl, and ethynyl, and $R^4$ is as defined above. Another embodiment comprises a compound of Formula (III), or a pharmaceutically acceptable salt thereof, wherein $R^2$ is Cl, $R^3$ is selected from the group of $CH_2F$, $CHF_2$, and $CH_2Cl$, and $R^4$ is as defined above.

Another embodiment comprises a compound of Formula (III), or a pharmaceutically acceptable salt thereof, wherein $R^2$ is OH, $R^3$ is selected from the group of CN and $N_3$, and $R^4$ is as defined above. A further embodiment comprises a compound of Formula (III), or a pharmaceutically acceptable salt thereof, wherein $R^2$ is OH, $R^3$ is selected from the group of methyl, ethyl, propyl, vinyl, propenyl, ethynyl and $CH_2OMe$, and $R^4$ is as defined above. A further embodiment comprises a compound of Formula (III), or a pharmaceutically acceptable salt thereof, wherein $R^2$ is OH, $R^3$ is selected from the group of methyl, ethyl, and propyl, and $R^4$ is as defined above. Another embodiment comprises a compound of Formula (III), or a pharmaceutically acceptable salt thereof, wherein $R^2$ is OH, $R^3$ is selected from the group of vinyl, propenyl, and ethynyl, and $R^4$ is as defined above. Another embodiment comprises a compound of Formula (III), or a pharmaceutically acceptable salt thereof, wherein $R^2$ is OH, $R^3$ is selected from the group of $CH_2F$, $CHF_2$, and $CH_2Cl$, and $R^4$ is as defined above.

Another embodiment comprises a compound of Formula (III), or a pharmaceutically acceptable salt thereof, wherein $R^2$ is $NH_2$, $R^3$ is selected from the group of CN and $N_3$, and $R^4$ is as defined above. A further embodiment comprises a compound of Formula (III), or a pharmaceutically acceptable salt thereof, wherein $R^2$ is $NH_2$, $R^3$ is selected from the group of methyl, ethyl, propyl, vinyl, propenyl, ethynyl and $CH_2OMe$, and $R^4$ is as defined above. A further embodiment comprises a compound of Formula (III), or a pharmaceutically acceptable salt thereof, wherein $R^2$ is $NH_2$, $R^3$ is selected from the group of methyl, ethyl, and propyl, and $R^4$ is as defined above. Another embodiment comprises a compound of Formula (III), or a pharmaceutically acceptable salt thereof, wherein $R^2$ is $NH_2$, $R^3$ is selected from the group of vinyl, propenyl, and ethynyl, and $R^4$ is as defined above. Another embodiment comprises a compound of Formula (III), or a pharmaceutically acceptable salt thereof, wherein $R^2$ is $NH_2$, $R^3$ is selected from the group of $CH_2F$, $CHF_2$, and $CH_2Cl$, and $R^4$ is as defined above.

Another embodiment comprises a compound of Formula (III), or a pharmaceutically acceptable salt thereof, wherein $R^2$ is $N_3$, $R^3$ is selected from the group of CN and $N_3$, and $R^4$ is as defined above. A further embodiment comprises a compound of Formula (III), or a pharmaceutically acceptable salt thereof, wherein $R^2$ is $N_3$, $R^3$ is selected from the group of methyl, ethyl, propyl, vinyl, propenyl, ethynyl and $CH_2OMe$, and $R^4$ is as defined above. A further embodiment comprises a compound of Formula (III), or a pharmaceutically acceptable salt thereof, wherein $R^2$ is $N_3$, $R^3$ is selected from the group of methyl, ethyl, and propyl, and $R^4$ is as defined above. Another embodiment comprises a compound of Formula (III), or a pharmaceutically acceptable salt thereof, wherein $R^2$ is $N_3$, $R^3$ is selected from the group of vinyl, propenyl, and ethynyl, and $R^4$ is as defined above. Another embodiment comprises a compound of Formula (III), or a pharmaceutically acceptable salt thereof, wherein $R^2$ is $N_3$, $R^3$ is selected from the group of $CH_2F$, $CHF_2$, and $CH_2Cl$, and $R^4$ is as defined above.

Within each of the groups and embodiments described herein for a compound of Formula (I), Formula (II), and Formula (III), or a pharmaceutically acceptable salt thereof, there is a further embodiment wherein $R^1$, $R^2$, and $R^3$ are as defined for the individual group or embodiment and $R^4$ is selected from:

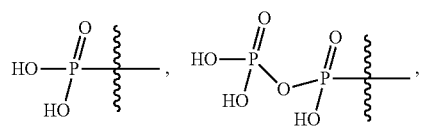,

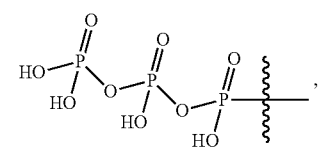,

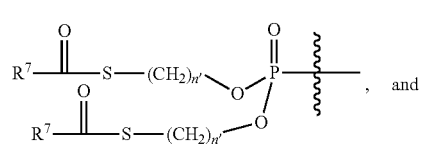, and

-continued

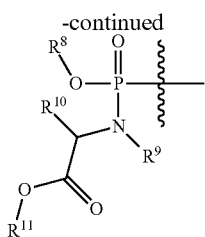;

wherein:

n' is selected from 1, 2, 3, and 4;

$R^7$ is selected from $C_1$-$C_8$ alkyl, —O—$C_1$-$C_8$ alkyl, benzyl, —O-benzyl, —$CH_2$—$C_3$-$C_6$ cycloalkyl, —O—$CH_2$—$C_3$-$C_6$ cycloalkyl, and $CF_3$;

$R^8$ is selected from phenyl, 1-naphthyl, 2-naphthyl,

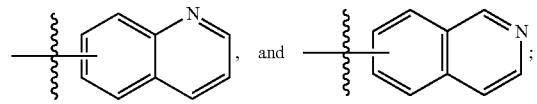

$R^9$ is selected from H and $CH_3$;

$R^{10}$ is selected from H or $C_1$-$C_6$ alkyl;

$R^{11}$ is selected from H, $C_1$-$C_8$ alkyl, benzyl, $C_3$-$C_6$ cycloalkyl, and —$CH_2$—$C_3$-$C_6$ cycloalkyl.

Within each of the groups and embodiments described herein for a compound of Formula (I), Formula (II), and Formula (III), or a pharmaceutically acceptable salt thereof, there is also a further embodiment wherein $R^1$, $R^2$, and $R^3$ are as defined for the individual group or embodiment and $R^4$ is selected from:

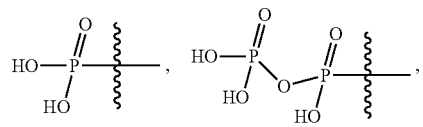,

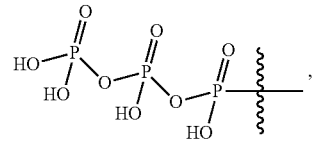,

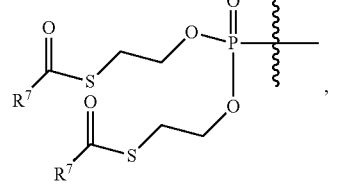, and

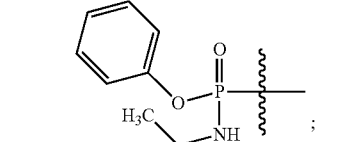;

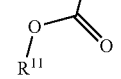

wherein:

$R^7$ is selected from $C_1$-$C_8$ alkyl, —O—$C_1$-$C_8$ alkyl, benzyl, and —$CH_2$—$C_3$-$C_6$ cycloalkyl; and $R^{11}$ is selected from $C_1$-$C_8$ alkyl, benzyl, $C_3$-$C_6$ cycloalkyl, and —$CH_2$—$C_3$-$C_6$ cycloalkyl.

Within each of the groups and embodiments described herein for a compound of Formula (I), Formula (II), and Formula (III), or a pharmaceutically acceptable salt thereof, there is also a further embodiment wherein $R^1$, $R^2$, and $R^3$ are as defined for the individual group or embodiment and $R^4$ is selected from:

(a)
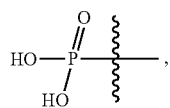

(b)
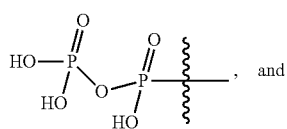, and (c)
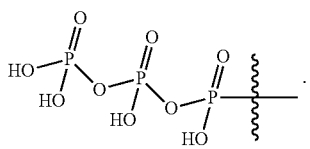 [SMILES: *P(=O)(O)OP(=O)(O)OP(=O)(O)O]

Within each of the groups and embodiments described herein for a compound of Formula (I), Formula (II), and Formula (III), or a pharmaceutically acceptable salt thereof, there is also a further embodiment wherein $R^1$, $R^2$, and $R^3$ are as defined for the individual group or embodiment and $R^4$ is a group of the formula:

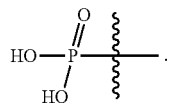

Within each of the groups and embodiments described herein for a compound of Formula (I), Formula (II), and Formula (III), or a pharmaceutically acceptable salt thereof, there is also a further embodiment wherein $R^1$, $R^2$, and $R^3$ are as defined for the individual group or embodiment and $R^4$ is a group of the formula:

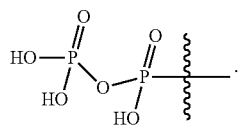

Within each of the groups and embodiments described herein for a compound of Formula (I), Formula (II), and Formula (III), or a pharmaceutically acceptable salt thereof, there is also a further embodiment wherein $R^1$, $R^2$, and $R^3$ are as defined for the individual group or embodiment and $R^4$ is a group of the formula:

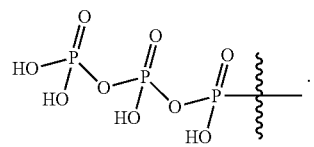

Also provided is a compound of Formula (IV):

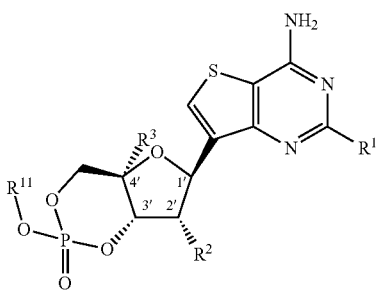

wherein:
$R^1$ is selected from the group of H, $CH_3$, F, Cl, and $NH_2$;
$R^2$ is selected from the group of F, Cl, OH, $NH_2$, and $N_3$;
$R^3$ is selected from the group of CN, $N_3$, methyl, ethyl, propyl, vinyl, propenyl, ethynyl, $CH_2F$, $CHF_2$, $CH_2Cl$, $CH_2SMe$, and $CH_2OMe$; and
$R^{11}$ is selected from H, $C_1$-$C_8$ alkyl, benzyl, $C_3$-$C_6$ cycloalkyl, and —$CH_2$—$C_3$-$C_6$ cycloalkyl;
or a pharmaceutically acceptable salt thereof.

An embodiment comprises a compound of Formula (IV) wherein $R^1$ is H and $R^2$, $R^3$, and $R^{11}$ are as defined above, or a pharmaceutically acceptable salt thereof. A further embodiment comprises a compound of Formula (IV) wherein $R^1$ is F and $R^2$, $R^3$, and $R^{11}$ are as defined above, or a pharmaceutically acceptable salt thereof. A further embodiment comprises a compound of Formula (IV) wherein $R^1$ is Cl and $R^2$, $R^3$, and $R^{11}$ are as defined above, or a pharmaceutically acceptable salt thereof. A further embodiment comprises a compound of Formula (IV) wherein $R^1$ is $NH_2$ and $R^2$, $R^3$, and $R^{11}$ are as defined above, or a pharmaceutically acceptable salt thereof.

Another embodiment comprises a compound of Formula (IV) wherein $R^1$ is H, $R^2$ is F, and $R^3$ and $R^{11}$ are as defined above, or a pharmaceutically acceptable salt thereof. A further embodiment comprises a compound of Formula (IV) wherein $R^1$ is H, $R^2$ is Cl, and $R^3$ and $R^{11}$ are as defined above, or a pharmaceutically acceptable salt thereof. Another embodiment comprises a compound of Formula (IV) wherein $R^1$ is H, $R^2$ is OH, and $R^3$ and R11 are as defined above, or a pharmaceutically acceptable salt thereof. Still another embodiment comprises a compound of Formula (IV) wherein $R^1$ is H, $R^2$ is $NH_2$, and $R^3$ and $R^{11}$ are as defined above, or a pharmaceutically acceptable salt thereof. Another embodiment comprises a compound of Formula (IV) wherein $R^1$ is H, $R^2$ is $N_3$, and $R^3$ and $R^{11}$ are as defined above, or a pharmaceutically acceptable salt thereof.

Another embodiment comprises a compound of Formula (IV), or a pharmaceutically acceptable salt thereof, wherein $R^1$ is H, $R^2$ is F, $R^3$ is selected from the group of CN and $N_3$, and $R^{11}$ is as defined above. A further embodiment comprises a compound of Formula (IV), or a pharmaceutically acceptable salt thereof, wherein $R^1$ is H, $R^2$ is F, $R^3$ is selected from the group of methyl, ethyl, propyl, vinyl, propenyl, ethynyl and CH$_2$OMe, and R$^{11}$ is as defined above. A further embodiment comprises a compound of Formula (IV), or a pharmaceutically acceptable salt thereof, wherein R$^1$ is H, R$^2$ is F, R$^3$ is selected from the group of methyl, ethyl, and propyl, and R$^{11}$ is as defined above. Another embodiment comprises a compound of Formula (IV), or a pharmaceutically acceptable salt thereof, wherein R$^1$ is H, R$^2$ is F, R$^3$ is selected from the group of vinyl, propenyl, and ethynyl, and R$^{11}$ is as defined above. Another embodiment comprises a compound of Formula (IV), or a pharmaceutically acceptable salt thereof, wherein R$^1$ is H, R$^2$ is F, R$^3$ is selected from the group of CH$_2$F, CHF$_2$, and CH$_2$Cl, and R$^{11}$ is as defined above.

Another embodiment comprises a compound of Formula (IV), or a pharmaceutically acceptable salt thereof, wherein R$^1$ is H, R$^2$ is Cl, R$^3$ is selected from the group of CN and N$_3$, and R$^{11}$ is as defined above. A further embodiment comprises a compound of Formula (IV), or a pharmaceutically acceptable salt thereof, wherein R$^1$ is H, R$^2$ is Cl, R$^3$ is selected from the group of methyl, ethyl, propyl, vinyl, propenyl, ethynyl and CH$_2$OMe, and R$^{11}$ is as defined above. A further embodiment comprises a compound of Formula (IV), or a pharmaceutically acceptable salt thereof, wherein R$^1$ is H, R$^2$ is Cl, R$^3$ is selected from the group of methyl, ethyl, and propyl, and R$^{11}$ is as defined above. Another embodiment comprises a compound of Formula (IV), or a pharmaceutically acceptable salt thereof, wherein R$^1$ is H, R$^2$ is Cl, R$^3$ is selected from the group of vinyl, propenyl, and ethynyl, and R$^{11}$ is as defined above. Another embodiment comprises a compound of Formula (IV), or a pharmaceutically acceptable salt thereof, wherein R$^1$ is H, R$^2$ is Cl, R$^3$ is selected from the group of CH$_2$F, CHF$_2$, and CH$_2$Cl, and R$^{11}$ is as defined above.

Another embodiment comprises a compound of Formula (IV), or a pharmaceutically acceptable salt thereof, wherein R$^1$ is H, R$^2$ is OH, R$^3$ is selected from the group of CN and N$_3$, and R$^{11}$ is as defined above. A further embodiment comprises a compound of Formula (IV), or a pharmaceutically acceptable salt thereof, wherein R$^1$ is H, R$^2$ is OH, R$^3$ is selected from the group of methyl, ethyl, propyl, vinyl, propenyl, ethynyl and CH$_2$OMe, and R$^{11}$ is as defined above. A further embodiment comprises a compound of Formula (IV), or a pharmaceutically acceptable salt thereof, wherein R$^1$ is H, R$^2$ is OH, R$^3$ is selected from the group of methyl, ethyl, and propyl, and R$^{11}$ is as defined above. Another embodiment comprises a compound of Formula (IV), or a pharmaceutically acceptable salt thereof, wherein R$^1$ is H, R$^2$ is OH, R$^3$ is selected from the group of vinyl, propenyl, and ethynyl, and R$^{11}$ is as defined above. Another embodiment comprises a compound of Formula (IV), or a pharmaceutically acceptable salt thereof, wherein R$^1$ is H, R$^2$ is OH, R$^3$ is selected from the group of CH$_2$F, CHF$_2$, and CH$_2$Cl, and R$^{11}$ is as defined above.

Another embodiment comprises a compound of Formula (IV), or a pharmaceutically acceptable salt thereof, wherein R$^1$ is H, R$^2$ is NH$_2$, R$^3$ is selected from the group of CN and N$_3$, and R$^{11}$ is as defined above. A further embodiment comprises a compound of Formula (III), or a pharmaceutically acceptable salt thereof, wherein R$^1$ is H, R$^2$ is NH$_2$, R$^3$ is selected from the group of methyl, ethyl, propyl, vinyl, propenyl, ethynyl and CH$_2$OMe, and R$^{11}$ is as defined above. A further embodiment comprises a compound of Formula (IV), or a pharmaceutically acceptable salt thereof, wherein R$^1$ is H, R$^2$ is NH$_2$, R$^3$ is selected from the group of methyl, ethyl, and propyl, and R$^{11}$ is as defined above. Another embodiment comprises a compound of Formula (IV), or a pharmaceutically acceptable salt thereof, wherein R$^1$ is H, R$^2$ is NH$_2$, R$^3$ is selected from the group of vinyl, propenyl, and ethynyl, and R$^{11}$ is as defined above. Another embodiment comprises a compound of Formula (IV), or a pharmaceutically acceptable salt thereof, wherein R$^1$ is H, R$^2$ is NH$_2$, R$^3$ is selected from the group of CH$_2$F, CHF$_2$, and CH$_2$Cl, and R$^{11}$ is as defined above.

Another embodiment comprises a compound of Formula (IV), or a pharmaceutically acceptable salt thereof, wherein R$^1$ is H, R$^2$ is N$_3$, R$^3$ is selected from the group of CN and N$_3$, and R$^{11}$ is as defined above. A further embodiment comprises a compound of Formula (IV), or a pharmaceutically acceptable salt thereof, wherein R$^1$ is H, R$^2$ is N$_3$, R$^3$ is selected from the group of methyl, ethyl, propyl, vinyl, propenyl, ethynyl and CH$_2$OMe, and R$^{11}$ is as defined above. A further embodiment comprises a compound of Formula (IV), or a pharmaceutically acceptable salt thereof, wherein R$^1$ is H, R$^2$ is N$_3$, R$^3$ is selected from the group of methyl, ethyl, and propyl, and R$^{11}$ is as defined above. Another embodiment comprises a compound of Formula (IV), or a pharmaceutically acceptable salt thereof, wherein R$^1$ is H, R$^2$ is N$_3$, R$^3$ is selected from the group of vinyl, propenyl, and ethynyl, and R$^{11}$ is as defined above. Another embodiment comprises a compound of Formula (IV), or a pharmaceutically acceptable salt thereof, wherein R$^1$ is H, R$^2$ is N$_3$, R$^3$ is selected from the group of CH$_2$F, CHF$_2$, and CH$_2$Cl, and R$^{11}$ is as defined above.

Another embodiment comprises a compound of Formula (V):

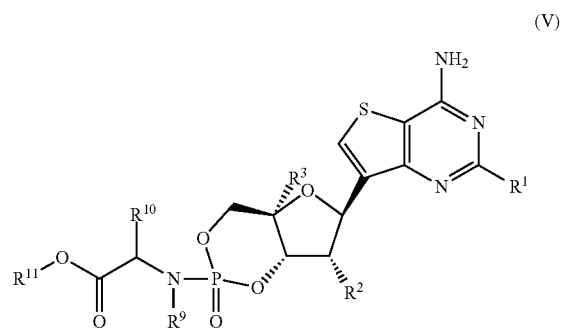

wherein:
R$^1$ is selected from the group of H, CH$_3$, F, Cl, and NH$_2$;
R$^2$ is selected from the group of F, Cl, OH, NH$_2$, and N$_3$;
R$^3$ is selected from the group of CN, N$_3$, methyl, ethyl, propyl, vinyl, propenyl, ethynyl, CH$_2$F, CHF$_2$, CH$_2$Cl, CH$_2$SMe, and CH$_2$OMe;
R$^9$ is selected from H and CH$_3$;
R$^{10}$ is selected from H or C$_1$-C$_6$ alkyl; and
R$^{11}$ is selected from H, C$_1$-C$_8$ alkyl, benzyl, C$_3$-C$_6$ cycloalkyl, and —CH$_2$—C$_3$-C$_6$ cycloalkyl;
or a pharmaceutically acceptable salt thereof.

An embodiment comprises a compound of Formula (V) wherein R$^1$ is H and R$^2$, R$^3$, and R$^{11}$ are as defined above, or a pharmaceutically acceptable salt thereof. A further embodiment comprises a compound of Formula (V) wherein R$^1$ is F and R$^2$, R$^3$, R$^9$, R$^{10}$, and R$^{11}$ are as defined above, or a pharmaceutically acceptable salt thereof. A further embodiment comprises a compound of Formula (V) wherein R$^1$ is Cl and R$^2$, R$^3$, R$^9$, R$^{10}$, and R$^{11}$ are as defined above, or a pharmaceutically acceptable salt thereof. A further embodiment comprises a compound of Formula (V) wherein R$^1$ is NH$_2$ and R$^2$, R$^3$, R$^9$, R$^{10}$, and R$^{11}$ are as defined above, or a pharmaceutically acceptable salt thereof.

Another embodiment comprises a compound of Formula (V) wherein $R^1$ is H, $R^2$ is F, and $R^3$, $R^9$, $R^{10}$, and $R^{11}$ are as defined above, or a pharmaceutically acceptable salt thereof. A further embodiment comprises a compound of Formula (V) wherein $R^1$ is H, $R^2$ is Cl, and $R^3$, $R^9$, $R^{10}$, and $R^{11}$ are as defined above, or a pharmaceutically acceptable salt thereof. Another embodiment comprises a compound of Formula (V) wherein $R^1$ is H, $R^2$ is OH, and $R^3$, $R^9$, $R^{10}$, and $R^{11}$ are as defined above, or a pharmaceutically acceptable salt thereof. Still another embodiment comprises a compound of Formula (V) wherein $R^1$ is H, $R^2$ is $NH_2$, and $R^3$, $R^9$, $R^{10}$, and $R^{11}$ are as defined above, or a pharmaceutically acceptable salt thereof. Another embodiment comprises a compound of Formula (V) wherein $R^1$ is H, $R^2$ is $N_3$, and $R^3$, $R^9$, $R^{10}$, and $R^{11}$ are as defined above, or a pharmaceutically acceptable salt thereof.

Another embodiment comprises a compound of Formula (V), or a pharmaceutically acceptable salt thereof, wherein $R^1$ is H, $R^2$ is F, $R^3$ is selected from the group of CN and $N_3$, and $R^9$, $R^{10}$, and $R^{11}$ are as defined above. A further embodiment comprises a compound of Formula (V), or a pharmaceutically acceptable salt thereof, wherein $R^1$ is H, $R^2$ is F, $R^3$ is selected from the group of methyl, ethyl, propyl, vinyl, propenyl, ethynyl and $CH_2OMe$, and $R^9$, $R^{10}$, and $R^{11}$ are as defined above. A further embodiment comprises a compound of Formula (V), or a pharmaceutically acceptable salt thereof, wherein $R^1$ is H, $R^2$ is F, $R^3$ is selected from the group of methyl, ethyl, and propyl, and $R^9$, $R^{10}$, and $R^{11}$ are as defined above. Another embodiment comprises a compound of Formula (V), or a pharmaceutically acceptable salt thereof, wherein $R^1$ is H, $R^2$ is F, $R^3$ is selected from the group of vinyl, propenyl, and ethynyl, and $R^9$, $R^{10}$, and $R^{11}$ are as defined above. Another embodiment comprises a compound of Formula (V), or a pharmaceutically acceptable salt thereof, wherein $R^1$ is H, $R^2$ is F, $R^3$ is selected from the group of $CH_2F$, $CHF_2$, and $CH_2Cl$, and $R^9$, $R^{10}$, and $R^{11}$ are as defined above.

Another embodiment comprises a compound of Formula (V), or a pharmaceutically acceptable salt thereof, wherein $R^1$ is H, $R^2$ is Cl, $R^3$ is selected from the group of CN and $N_3$, and $R^9$, $R^{10}$, and $R^{11}$ are as defined above. A further embodiment comprises a compound of Formula (V), or a pharmaceutically acceptable salt thereof, wherein $R^1$ is H, $R^2$ is Cl, $R^3$ is selected from the group of methyl, ethyl, propyl, vinyl, propenyl, ethynyl and $CH_2OMe$, and $R^9$, $R^{10}$, and $R^{11}$ are as defined above. A further embodiment comprises a compound of Formula (V), or a pharmaceutically acceptable salt thereof, wherein $R^1$ is H, $R^2$ is Cl, $R^3$ is selected from the group of methyl, ethyl, and propyl, and $R^9$, $R^{10}$, and $R^{11}$ are as defined above. Another embodiment comprises a compound of Formula (V), or a pharmaceutically acceptable salt thereof, wherein $R^1$ is H, $R^2$ is Cl, $R^3$ is selected from the group of vinyl, propenyl, and ethynyl, and $R^9$, $R^{10}$, and $R^{11}$ are as defined above. Another embodiment comprises a compound of Formula (V), or a pharmaceutically acceptable salt thereof, wherein $R^1$ is H, $R^2$ is Cl, $R^3$ is selected from the group of $CH_2F$, $CHF_2$, and $CH_2Cl$, and $R^9$, $R^{10}$, and $R^{11}$ are as defined above.

Another embodiment comprises a compound of Formula (V), or a pharmaceutically acceptable salt thereof, wherein $R^1$ is H, $R^2$ is OH, $R^3$ is selected from the group of CN and $N_3$, and $R^9$, $R^{10}$, and $R^{11}$ are as defined above. A further embodiment comprises a compound of Formula (V), or a pharmaceutically acceptable salt thereof, wherein $R^1$ is H, $R^2$ is OH, $R^3$ is selected from the group of methyl, ethyl, propyl, vinyl, propenyl, ethynyl and $CH_2OMe$, and $R^9$, $R^{10}$, and $R^{11}$ are as defined above. A further embodiment comprises a compound of Formula (V), or a pharmaceutically acceptable salt thereof, wherein $R^1$ is H, $R^2$ is OH, $R^3$ is selected from the group of methyl, ethyl, and propyl, and $R^9$, $R^{10}$, and $R^{11}$ are as defined above. Another embodiment comprises a compound of Formula (V), or a pharmaceutically acceptable salt thereof, wherein $R^1$ is H, $R^2$ is OH, $R^3$ is selected from the group of vinyl, propenyl, and ethynyl, and $R^9$, $R^{10}$, and $R^{11}$ are as defined above. Another embodiment comprises a compound of Formula (V), or a pharmaceutically acceptable salt thereof, wherein $R^1$ is H, $R^2$ is OH, $R^3$ is selected from the group of $CH_2F$, $CHF_2$, and $CH_2Cl$, and $R^9$, $R^{10}$, and $R^{11}$ are as defined above.

Another embodiment comprises a compound of Formula (V), or a pharmaceutically acceptable salt thereof, wherein $R^1$ is H, $R^2$ is $NH_2$, $R^3$ is selected from the group of CN and $N_3$, and $R^9$, $R^{10}$, and $R^{11}$ are as defined above. A further embodiment comprises a compound of Formula (V), or a pharmaceutically acceptable salt thereof, wherein $R^1$ is H, $R^2$ is $NH_2$, $R^3$ is selected from the group of methyl, ethyl, propyl, vinyl, propenyl, ethynyl and $CH_2OMe$, and $R^9$, $R^{10}$, and $R^{11}$ are as defined above. A further embodiment comprises a compound of Formula (V), or a pharmaceutically acceptable salt thereof, wherein $R^1$ is H, $R^2$ is $NH_2$, $R^3$ is selected from the group of methyl, ethyl, and propyl, and $R^9$, $R^{10}$, and $R^{11}$ are as defined above. Another embodiment comprises a compound of Formula (V), or a pharmaceutically acceptable salt thereof, wherein $R^1$ is H, $R^2$ is $NH_2$, $R^3$ is selected from the group of vinyl, propenyl, and ethynyl, and $R^9$, $R^{10}$, and $R^{11}$ are as defined above. Another embodiment comprises a compound of Formula (V), or a pharmaceutically acceptable salt thereof, wherein $R^1$ is H, $R^2$ is $NH_2$, $R^3$ is selected from the group of $CH_2F$, $CHF_2$, and $CH_2Cl$, and $R^9$, $R^{10}$, and $R^{11}$ are as defined above.

Another embodiment comprises a compound of Formula (V), or a pharmaceutically acceptable salt thereof, wherein $R^1$ is H, $R^2$ is $N_3$, $R^3$ is selected from the group of CN and $N_3$, and $R^9$, $R^{10}$, and $R^{11}$ are as defined above. A further embodiment comprises a compound of Formula (V), or a pharmaceutically acceptable salt thereof, wherein $R^1$ is H, $R^2$ is $N_3$, $R^3$ is selected from the group of methyl, ethyl, propyl, vinyl, propenyl, ethynyl and $CH_2OMe$, and $R^9$, $R^{10}$, and $R^{11}$ are as defined above. A further embodiment comprises a compound of Formula (V), or a pharmaceutically acceptable salt thereof, wherein $R^1$ is H, $R^2$ is $N_3$, $R^3$ is selected from the group of methyl, ethyl, and propyl, and $R^9$, $R^{10}$, and $R^{11}$ are as defined above. Another embodiment comprises a compound of Formula (V), or a pharmaceutically acceptable salt thereof, wherein $R^1$ is H, $R^2$ is $N_3$, $R^3$ is selected from the group of vinyl, propenyl, and ethynyl, and $R^9$, $R^{10}$, and $R^{11}$ are as defined above. Another embodiment comprises a compound of Formula (V), or a pharmaceutically acceptable salt thereof, wherein $R^1$ is H, $R^2$ is $N_3$, $R^3$ is selected from the group of $CH_2F$, $CHF_2$, and $CH_2Cl$, and $R^9$, $R^{10}$, and $R^{11}$ are as defined above.

Also provided is a compound of Formula (VI):

wherein:

X is selected from the group of O, S, and NH;
R¹ is selected from the group of H, CH₃, F, Cl, and NH₂;
R² is selected from the group of F, Cl, OH, NH₂, CN, and N₃; and
R³ is selected from the group of CN, N₃, methyl, ethyl, propyl, vinyl, propenyl, ethynyl, CH₂F, CHF₂, CH₂Cl, CH₂SMe, and CH₂OMe;
or a pharmaceutically acceptable salt thereof.

Also provided is a compound of Formula (VII):

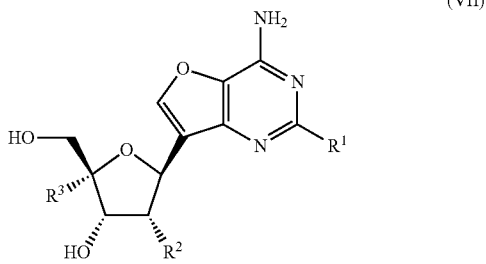

(VII)

wherein:

R¹ is selected from the group of H, CH₃, F, Cl, and NH₂;
R² is selected from the group of F, Cl, OH, NH₂, CN, and N₃; and
R³ is selected from the group of CN, N₃, methyl, ethyl, propyl, vinyl, propenyl, ethynyl, CH₂F, CHF₂, CH₂Cl, CH₂SMe, and CH₂OMe;
or a pharmaceutically acceptable salt thereof.

Also provided is a compound of Formula (VIII):

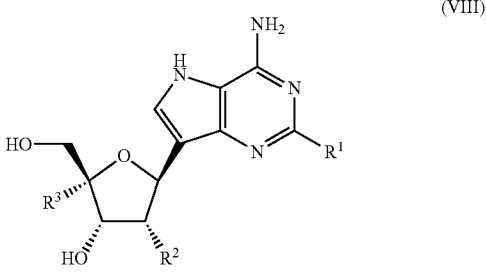

(VIII)

wherein:

R¹ is selected from the group of H, CH₃, F, Cl, and NH₂;
R² is selected from the group of F, Cl, OH, NH₂, CN, and N₃; and
R³ is selected from the group of CN, N₃, methyl, ethyl, propyl, vinyl, propenyl, ethynyl, CH₂F, CHF₂, CH₂Cl, CH₂SMe, and CH₂OMe;
or a pharmaceutically acceptable salt thereof.

Also provided is a compound of Formula (IX):

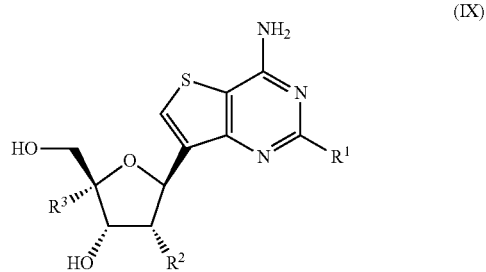

(IX)

wherein:

R¹ is selected from the group of H, CH₃, F, Cl, and NH₂;
R² is selected from the group of F, Cl, OH, NH₂, CN, and N₃; and
R³ is selected from the group of CN, N₃, methyl, ethyl, propyl, vinyl, propenyl, ethynyl, CH₂F, CHF₂, CH₂Cl, CH₂SMe, and CH₂OMe;
or a pharmaceutically acceptable salt thereof.

An embodiment comprises a compound of Formula (IX) wherein R¹ is H and R² and R³ are as defined above, or a pharmaceutically acceptable salt thereof. A further embodiment comprises a compound of Formula (IX) wherein R¹ is F and R² and R³ are as defined above, or a pharmaceutically acceptable salt thereof. A further embodiment comprises a compound of Formula (IX) wherein R¹ is Cl and R² and R³ are as defined above, or a pharmaceutically acceptable salt thereof. A further embodiment comprises a compound of Formula (IX) wherein R¹ is NH₂ and R² and R³ are as defined above, or a pharmaceutically acceptable salt thereof.

Another embodiment comprises a compound of Formula (IX) wherein R¹ is H, R² is F, and R³ is as defined above, or a pharmaceutically acceptable salt thereof. A further embodiment comprises a compound of Formula (IX) wherein R¹ is H, R² is Cl, and R³ is as defined above, or a pharmaceutically acceptable salt thereof. Another embodiment comprises a compound of Formula (IX) wherein R¹ is H, R² is OH, and R³ is as defined above, or a pharmaceutically acceptable salt thereof. Still another embodiment comprises a compound of Formula (IX) wherein R¹ is H, R² is NH₂, and R³ is as defined above, or a pharmaceutically acceptable salt thereof. Another embodiment comprises a compound of Formula (V) wherein R¹ is H, R² is N₃, and R³ is as defined above, or a pharmaceutically acceptable salt thereof.

Another embodiment comprises a compound of Formula (IX), or a pharmaceutically acceptable salt thereof, wherein R¹ is H, R² is F, and R³ is selected from the group of CN and N₃. A further embodiment comprises a compound of Formula (IX), or a pharmaceutically acceptable salt thereof, wherein R¹ is H, R² is F, and R³ is selected from the group of methyl, ethyl, propyl, vinyl, propenyl, ethynyl, CH₂SMe, and CH₂OMe. A further embodiment comprises a compound of Formula (IX), or a pharmaceutically acceptable salt thereof, wherein R¹ is H, R² is F, and R³ is selected from the group of methyl, ethyl, and propyl. Another embodiment comprises a compound of Formula (IX), or a pharmaceutically acceptable salt thereof, wherein R¹ is H, R² is F, and R³ is selected from the group of vinyl, propenyl, and ethynyl. Another embodiment comprises a compound of Formula (IX), or a pharmaceutically acceptable salt thereof, wherein R¹ is H, R² is F, and R³ is selected from the group of CH₂F, CHF₂, and CH₂Cl.

Another embodiment comprises a compound of Formula (IX), or a pharmaceutically acceptable salt thereof, wherein R¹ is H, R² is Cl, and R³ is selected from the group of CN and N₃. A further embodiment comprises a compound of Formula (IX), or a pharmaceutically acceptable salt thereof, wherein R¹ is H, R² is Cl, and R³ is selected from the group of methyl, ethyl, propyl, vinyl, propenyl, ethynyl, CH₂SMe, and CH₂OMe. A further embodiment comprises a compound of Formula (IX), or a pharmaceutically acceptable salt thereof, wherein R¹ is H, R² is Cl, and R³ is selected from the group of methyl, ethyl, and propyl. Another embodiment comprises a compound of Formula (IX), or a pharmaceutically acceptable salt thereof, wherein R¹ is H, R² is Cl, and R³ is selected from the group of vinyl, propenyl, and ethynyl. Another embodiment comprises a compound of Formula (IX), or a pharmaceutically acceptable salt thereof, wherein $R^1$ is H, $R^2$ is Cl, and $R^3$ is selected from the group of $CH_2F$, $CHF_2$, and $CH_2Cl$.

Another embodiment comprises a compound of Formula (IX), or a pharmaceutically acceptable salt thereof, wherein $R^1$ is H, $R^2$ is OH, and $R^3$ is selected from the group of CN and $N_3$. A further embodiment comprises a compound of Formula (IX), or a pharmaceutically acceptable salt thereof, wherein $R^1$ is H, $R^2$ is OH, and $R^3$ is selected from the group of methyl, ethyl, propyl, vinyl, propenyl, ethynyl, $CH_2SMe$, and $CH_2OMe$. A further embodiment comprises a compound of Formula (IX), or a pharmaceutically acceptable salt thereof, wherein $R^1$ is H, $R^2$ is OH, and $R^3$ is selected from the group of methyl, ethyl, and propyl. Another embodiment comprises a compound of Formula (IX), or a pharmaceutically acceptable salt thereof, wherein $R^1$ is H, $R^2$ is OH, and $R^3$ is selected from the group of vinyl, propenyl, and ethynyl. Another embodiment comprises a compound of Formula (IX), or a pharmaceutically acceptable salt thereof, wherein $R^1$ is H, $R^2$ is OH, and $R^3$ is selected from the group of $CH_2F$, $CHF_2$, and $CH_2Cl$.

Another embodiment comprises a compound of Formula (IX), or a pharmaceutically acceptable salt thereof, wherein $R^1$ is H, $R^2$ is $NH_2$, and $R^3$ is selected from the group of CN and $N_3$. A further embodiment comprises a compound of Formula (IX), or a pharmaceutically acceptable salt thereof, wherein $R^1$ is H, $R^2$ is $NH_2$, and $R^3$ is selected from the group of methyl, ethyl, propyl, vinyl, propenyl, ethynyl, $CH_2SMe$, and $CH_2OMe$. A further embodiment comprises a compound of Formula (IX), or a pharmaceutically acceptable salt thereof, wherein $R^1$ is H, $R^2$ is $NH_2$, and $R^3$ is selected from the group of methyl, ethyl, and propyl. Another embodiment comprises a compound of Formula (IX), or a pharmaceutically acceptable salt thereof, wherein $R^1$ is H, $R^2$ is $NH_2$, and $R^3$ is selected from the group of vinyl, propenyl, and ethynyl. Another embodiment comprises a compound of Formula (IX), or a pharmaceutically acceptable salt thereof, wherein $R^1$ is H, $R^2$ is $NH_2$, and $R^3$ is selected from the group of $CH_2F$, $CHF_2$, and $CH_2Cl$.

Another embodiment comprises a compound of Formula (IX), or a pharmaceutically acceptable salt thereof, wherein $R^1$ is H, $R^2$ is $N_3$, and $R^3$ is selected from the group of CN and $N_3$. A further embodiment comprises a compound of Formula (IX), or a pharmaceutically acceptable salt thereof, wherein $R^1$ is H, $R^2$ is $N_3$, and $R^3$ is selected from the group of methyl, ethyl, propyl, vinyl, propenyl, ethynyl, $CH_2SMe$, and $CH_2OMe$. A further embodiment comprises a compound of Formula (IX), or a pharmaceutically acceptable salt thereof, wherein $R^1$ is H, $R^2$ is $N_3$, and $R^3$ is selected from the group of methyl, ethyl, and propyl. Another embodiment comprises a compound of Formula (IX), or a pharmaceutically acceptable salt thereof, wherein $R^1$ is H, $R^2$ is $N_3$, and $R^3$ is selected from the group of vinyl, propenyl, and ethynyl. Another embodiment comprises a compound of Formula (IX), or a pharmaceutically acceptable salt thereof, wherein $R^1$ is H, $R^2$ is $N_3$, and $R^3$ is selected from the group of $CH_2F$, $CHF_2$, and $CH_2Cl$.

Also provided are separate embodiments comprising a compound of Formula (Xa), Formula (Xb), or Formula (Xc), or a pharmaceutically acceptable salt thereof:

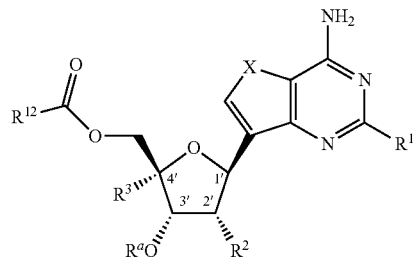

(Xa)

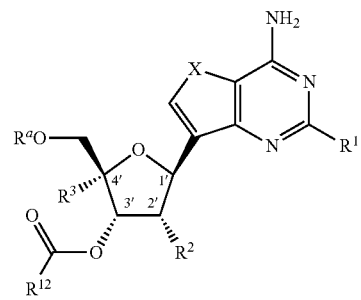

(Xb)

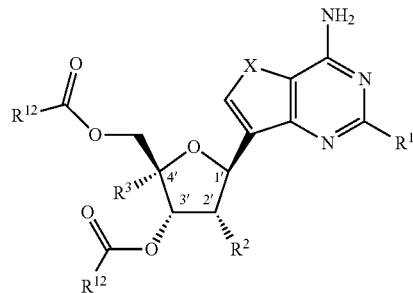

(Xc)

wherein X, $R^1$, $R^2$, $R^3$, and $R^a$ are as defined above for Formula (I), and $R^{12}$ is selected in each instance from the group of $C_1$-$C_6$ alkyl optionally substituted by one $NH_2$ group.

Within each of the embodiments above represented by Formula (Xa), Formula (Xb), or Formula (Xc) there is a further embodiment comprising the compound, or a pharmaceutically acceptable salt thereof, wherein X is S, $R^{12}$ is selected in each instance from the group of $C_1$-$C_6$ alkyl optionally substituted by one $NH_2$ group, and $R^1$, $R^2$, $R^3$, and $R^a$ are as defined above for Formula (I).

Within each of the embodiments above represented by Formula (Xa), Formula (Xb), or Formula (Xc) there is a further embodiment comprising the compound, or a pharmaceutically acceptable salt thereof, wherein X is S, $R^1$ is H, and $R^2$, $R^3$, and $R^a$ are as defined above for Formula (I).

Within each of the embodiments above represented by Formula (Xa), Formula (Xb), or Formula (Xc) there is a further embodiment comprising the compound, or a pharmaceutically acceptable salt thereof, wherein X is S, $R^1$ is H, $R^{12}$ is $C_2$-$C_4$ alkyl or —$C(NH_2)$—$C_2$-$C_4$ alkyl, and $R^2$, $R^3$, and $R^a$ are as defined above for Formula (I).

Within each of the embodiments above represented by Formula (Xa), Formula (Xb), or Formula (Xc) there is a further embodiment comprising the compound, or a pharmaceutically acceptable salt thereof, wherein X is S, $R^1$ is H, $R^{12}$ is selected from the group of ethyl, isopropyl, —$C(NH_2)$-ethyl, —$C(NH_2)$-isopropyl, and $R^2$, $R^3$, and $R^a$ are as defined above for Formula (I).

Additional separate embodiments comprise a compound of any of the formulas below, or a pharmaceutically acceptable salt thereof:

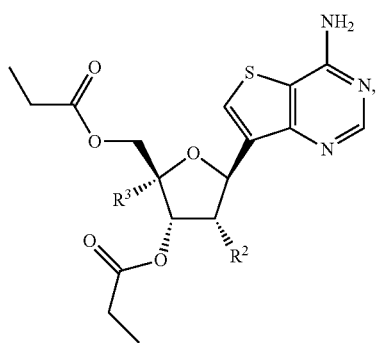
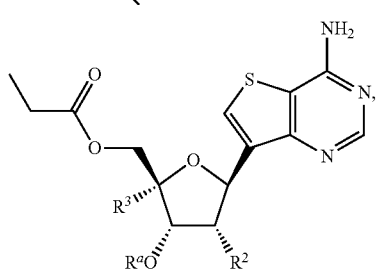
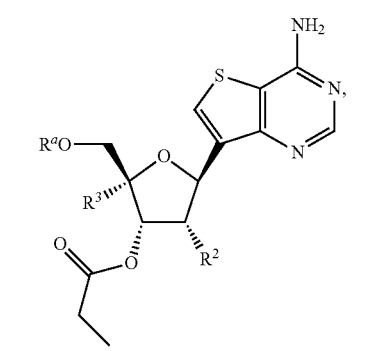
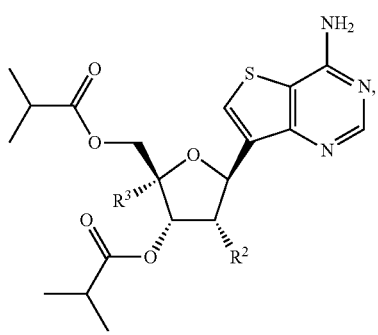
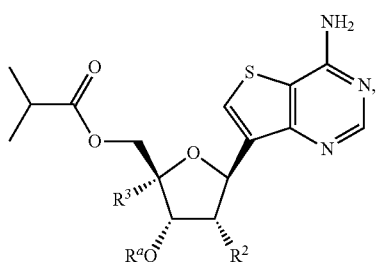
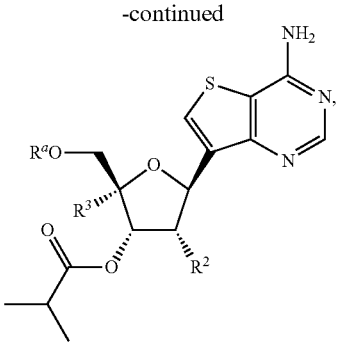
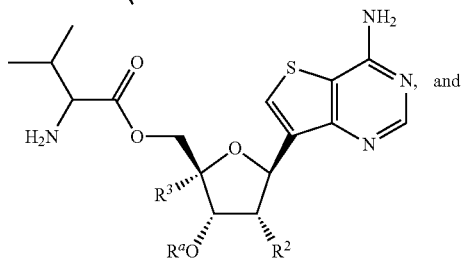
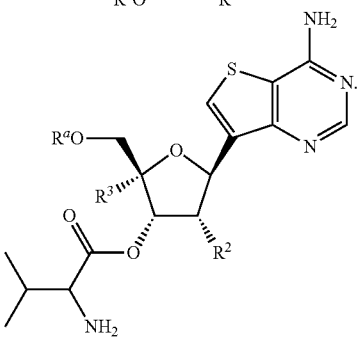

wherein, in each separate embodiment, $R^2$, $R^3$, $R^a$ are as defined above for Formula (I).

The terms halo and halogen refer to halogen atoms selected from F, Cl, Br, and I.

"Azido" refers to an azide group, i.e. the group —$N_3$. The term "n" as used herein refers to an integer selected from 2, 3, 4, 5, 6, 7, 8, 9, 10, 11, 12, 13, 14, 15, 16, 17, 18, 19, and 20.

The term "haloalkyl" as used herein refers to an alkyl as defined herein, wherein one or more hydrogen atoms are each replaced by a halo substituent. For example, a ($C_1$-$C_6$) haloalkyl is a ($C_1$-$C_6$)alkyl wherein one or more of the hydrogen atoms have been replaced by a halo substituent. Such a range includes one halo substituent on the alkyl group t to complete halogenation of the alkyl group.

The term "($C_{1-n}$)haloalkyl" as used herein, wherein n is an integer, either alone or in combination with another radical, is intended to mean an alkyl radical having 1 to n carbon atoms as defined above wherein one or more hydrogen atoms are each replaced by a halo substituent. Examples of ($C_{1-n}$)haloalkyl, wherein n is 2 include, but are not limited to, chloromethyl, chloroethyl, dichloroethyl, bromomethyl, bromoethyl, dibromoethyl, fluoromethyl, difluoromethyl, trifluoromethyl, fluoroethyl and difluoroethyl. Such groups may also be described based on the relevant halogen as "($C_{1-n}$)chloroalkyl", "($C_{1-n}$)bromoalkyl", or "($C_{1-n}$)fluoroalkyl groups".

The term "($C_{1-n}$)alkyl" as used herein, wherein n is an integer, either alone or in combination with another radical, is intended to mean acyclic, straight or branched chain alkyl radicals containing from 1 to n carbon atoms. "$(C_{1-8})$alkyl" includes, but is not limited to, methyl, ethyl, propyl (n-propyl), butyl (n-butyl), 1-methylethyl (iso-propyl), 1-methylpropyl (sec-butyl), 2-methylpropyl (iso-butyl), 1,1-dimethylethyl (tert-butyl), pentyl, hexyl, heptyl, and octyl. The abbreviation Me denotes a methyl group; Et denotes an ethyl group, Pr denotes a propyl group, iPr denotes a 1-methylethyl group, Bu denotes a butyl group and tBu denotes a 1,1-dimethylethyl group.

The term "alkyl" refers to a hydrocarbon containing normal, secondary, or tertiary atoms. For example, an alkyl group can have 1 to 20 carbon atoms (i.e, $(C_1-C_{20})$alkyl), 1 to 10 carbon atoms (i.e., $(C_1-C_{10})$alkyl), 1 to 8 carbon atoms (i.e., $(C_1-C_8)$alkyl) or 1 to 6 carbon atoms (i.e., $(C_1-C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl(—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$). "Alkyl" also refers to a saturated, branched or straight chain hydrocarbon radical having two monovalent radical centers derived by the removal of two hydrogen atoms from the same or two different carbon atoms of a parent alkane. For example, an alkyl group can have 1 to 10 carbon atoms (i.e., $(C_1-C_{10})$ alkyl), or 1 to 6 carbon atoms (i.e., $(C_1-C_6)$alkyl) or 1-3 carbon atoms (i.e., $(C_1-C_3)$alkyl). Typical alkyl radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

"Alkenyl" is a straight or branched hydrocarbon containing normal, secondary or tertiary carbon atoms with at least one site of unsaturation, i.e. a carbon-carbon, $sp^2$ double bond. For example, an alkenyl group can have 2 to 20 carbon atoms (i.e., $C_2-C_{20}$ alkenyl), 2 to 8 carbon atoms (i.e., $C_2-C_8$ alkenyl), or 2 to 6 carbon atoms (i.e., $C_2-C_6$ alkenyl). Examples of suitable alkenyl groups include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

The term "$(C_{2-n})$alkenyl", as used herein, wherein n is an integer, either alone or in combination with another radical, is intended to mean an unsaturated, acyclic straight or branched chain radical containing two to n carbon atoms, at least two of which are bonded to each other by a double bond. Examples of such radicals include, but are not limited to, ethenyl (vinyl), 1-propenyl, 2-propenyl, and 1-butenyl. Unless specified otherwise, the term "$(C_{2-n})$alkenyl" is understood to encompass individual stereoisomers where possible, including but not limited to (E) and (Z) isomers, and mixtures thereof. When a $(C_{2-n})$alkenyl group is substituted, it is understood to be substituted on any carbon atom thereof which would otherwise bear a hydrogen atom, unless specified otherwise, such that the substitution would give rise to a chemically stable compound, such as are recognized by those skilled in the art.

"Alkynyl" is a straight or branched hydrocarbon containing normal, secondary or tertiary carbon atoms with at least one site of unsaturation, i.e. a carbon-carbon, sp triple bond. For example, an alkynyl group can have 2 to 20 carbon atoms (i.e., $C_2-C_{20}$ alkynyl), 2 to 8 carbon atoms (i.e., $C_2-C_8$ alkyne,), or 2 to 6 carbon atoms (i.e., $C_2-C_6$ alkynyl). Examples of suitable alkynyl groups include, but are not limited to, acetylenic (—C≡CH), propargyl (—$CH_2$C≡CH), and the like.

The term "$(C_{2-n})$alkynyl", as used herein, wherein n is an integer, either alone or in combination with another radical, is intended to mean an unsaturated, acyclic straight or branched chain radical containing two to n carbon atoms, at least two of which are bonded to each other by a triple bond. Examples of such radicals in which n is 4 include, but are not limited to, ethynyl, 1-propynyl, 2-propynyl, and 1-butynyl. When a $(C_{2-n})$alkynyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "aryl" as used herein refers to a single aromatic ring or a bicyclic or multicyclic ring. For example, an aryl group can have 6 to 20 carbon atoms, 6 to 14 carbon atoms, or 6 to 12 carbon atoms. Aryl includes a phenyl radical or an ortho-fused bicyclic or multicyclic radical having about 9 to 14 atoms in which at least one ring is aromatic (e.g. an aryl fused to one or more aryl or carbocycle). Such bicyclic or multicyclic rings may be optionally substituted with one or more (e.g. 1, 2 or 3)oxo groups on any carbocycle portion of the bicyclic or multicyclic ring. It is to be understood that the point of attachment of a bicyclic or multicyclic radical, as defined above, can be at any position of the ring including an aryl or a carbocycle portion of the ring. Typical aryl groups include, but are not limited to, phenyl, indenyl, naphthyl, 1,2,3,4-tetrahydronaphthyl, anthracenyl, and the like.

"Aryl" includes an aromatic hydrocarbon monocyclic or bicyclic ring having from six to 10 ring carbon atoms, including phenyl and naphthyl rings. Substituted aryl groups include an aromatic hydrocarbon monocyclic or bicyclic ring having from six to 10 ring carbon atoms, including phenyl and naphthyl rings, including 1-naphthyl, 2-naphthyl rings, as well as a carbocyclic aromatic monocyclic group containing 6 carbon atoms which may be further fused to a second 5- or 6-membered carbocyclic group which may be aromatic, saturated or unsaturated, including indanyl, indenyl, tetrahydronaphthyl and dihydronaphthyl rings, with each of the aryl rings being substituted by 0, 1, 2, or 3 substituents independently selected from halogen, —OH, —CN, —$NO_2$, —$NH_2$, —NH($C_1-C_6$ alkyl), —N($C_1-C_6$ alkyl)$_2$, $C_1-C_6$ alkyl, $C_1-C_6$ alkoxy, and —$CF_3$ "Arylalkyl" refers to an alkyl radical as defined herein in which one of the hydrogen atoms bonded to a carbon atom is replaced with an aryl radical as described herein (i.e., an aryl-alkyl-moiety). The alkyl group of the "arylalkyl" is typically 1 to 6 carbon atoms (i.e. aryl($C_1-C_6$)alkyl). Arylalkyl groups include, but are not limited to, benzyl, 2-phenylethan-1-yl, 1-phenylpropan-1-yl, naphthylmethyl, 2-naphthylethan-1-yl and the like.

The term "aryl-($C_{1-n}$)alkyl-" as used herein, wherein n is an integer, either alone or in combination with another radical, is intended to mean an alkyl radical having 1 to n carbon atoms as defined above which is itself substituted with an aryl radical as defined above. Examples of aryl-($C_{1-n}$)alkyl- include, but are not limited to, phenylmethyl (benzyl), 1-phenylethyl, 2-phenylethyl and phenylpropyl. When an aryl-($C_{1-n}$)alkyl- group is substituted, it is understood that substituents may be attached to either the aryl or the alkyl portion thereof or both, unless specified otherwise, such that the substitution would give rise to a chemically stable compound, such as are recognized by those skilled in the art.

Examples of "arylalkyl" used herein refer to a moiety of the formula —$(CH_2)_q$—Y, wherein q is an integer selected independently in each instance from 1, 2, 3, 4, 5, or 6, and "Y" is a phenyl or naphthyl ring, each substituted by 0, 1, 2, or 3 substituents independently selected from halogen, —OH, —CN, —$NO_2$, —$NH_2$, —NH($C_1$-$C_6$ alkyl), —N($C_1$-$C_6$ alkyl)$_2$, $C_1$-$C_6$ alkyl, $C_1$-$C_6$ alkoxy, and —$CF_3$.

The term "heterocycle" are synonymous and refers to monocyclic and fused bicyclic, saturated or partially unsaturated rings having, unless otherwise indicated, 3, 4, 5, 6, 7, 8, 9, or 10 ring atoms wherein 1, 2, 3, or 4 ring atoms is/are a heteroatom independently selected from N, O and S and all remaining ring atoms are C. In one embodiment, the heterocyclic group has 5, 6, 9 or 10 rings atoms wherein 1, 2 or 3 ring atoms is/are a heteroatom independently selected from N, O and S. In all embodiments wherein the heterocyclic group includes 2 or more heteroatoms (N, O and S) the heteroatoms may be the same or different. In all embodiments wherein the compound of Formula I includes 2 or more heterocyclic groups, the heterocyclic groups may be the same or different. Examples of heterocyclic groups include but are not limited to oxiranyl, azetidinyl, oxetanyl, thietanyl, furanyl, tetrahydrofuranyl, thiophenyl, tetrahydrothiophenyl, sulfur oxidized tetrahydrothiophenyl, pyrrolyl, pyrrolinyl, pyrrolidinyl, dioxolanyl, oxazolidinyl, oxazolyl, isoxazolyl, thiazolyl, isothiazolyl, imidazolyl, imidazolinyl, imidazolidinyl, pyrazolyl, pyrazolinyl, pyrazolidinyl, triazolyl, tetrazolyl, pyranyl, dihydropyranyl, tetrahydropyranyl, pyridyl, dihydropyridyl, piperidyl, dioxanyl, morpholinyl, dithianyl, thiomorpholinyl, pyridazinyl, pyrimidinyl, pyrazinyl, piperazinyl, triazinyl, indolizinyl, indolyl, isoindolyl, oxindolyl, indolinyl, benzofuranyl, dihydrobenzofuranyl, isobenzofuranyl, benzothienyl, indazolyl, benzimidazolyl, benzoxazolinyl, benzoxazolyl, benzisoxazolyl, benzthiazolyl, benzotriazolyl, benzopyranyl, purinyl, quinolizinyl, quinolinyl, isoquinolinyl, tetrahydroquinolinyl, tetrahydroisoquinolinyl, decahydroquinolinyl, octahydroisoquinolinyl, cinnolinyl, phthalazinyl, quinazolinyl, quinoxalinyl, naphthyridinyl, pteridinyl, thianaphthalenyl and the like. Heterocyclic groups may be bound through any available ring carbon or ring heteroatom, such as N. Each "Heterocyclic group", "heterocyclic ring" or "heterocycle" may be substituted by 0, 1, 2, or 3 substituents independently selected from halogen, —OH, —CN, —$NO_2$, —$NH_2$, —NH($C_1$-$C_6$ alkyl), —N($C_1$-$C_6$ alkyl)$_2$, $C_1$-$C_6$ alkyl, $C_1$-$C_6$ alkoxy, and —$CF_3$.

The term cycloalkyl refers to a cyclic aliphatic group. The cycloalkyl groups herein may be referenced by the number of carbon atoms in their ring, such as "$C_3$-$C_4$ cycloalkyl" referring to a cycloalkyl ring with 3 or 4 carbon ring atoms or "$C_3$-$C_6$ cycloalkyl" indicating a cycloalkyl ring with 3, 4, 5, or 6 carbon ring atoms, i.e. a cyclopropyl, cyclobutyl, cyclopentyl, or cyclohexyl ring.

The term "carbocycle" or "carbocyclyl" refers to a saturated (i.e., cycloalkyl) or partially unsaturated (e.g., cycloalkenyl, cycloalkadienyl, etc.) ring having 3 to 8 carbon atoms as a monocycle or a multicyclic ring system. In one embodiment the carbocycle is a monocycle comprising 3-6 ring carbons (i.e. ($C_3$-$C_6$)carbocycle). Carbocycle includes multicyclic carbocycles having 7 to 12 carbon atoms as a bicycle, and up to about 20 carbon atoms as a polycycle provided that the largest single ring of a multicyclic carbocycle is 7 carbon atoms. The term "spiro-bicyclic carbocycle" refers to a carbocycle bicyclic ring system wherein the rings of the bicyclic ring system are connected to a single carbon atom (e.g. spiropentane, spiro[4,5]decane, spiro[4.5]decane, etc). The term "fused-bicyclic carbocycle" refers to a carbocycle bicyclic ring system wherein the rings of the bicyclic ring system are connected to two adjacent carbon atoms such as a bicyclo[4,5], [5,5], [5,6] or [6,6] system, or 9 or 10 ring atoms arranged as a bicyclo[5,6] or [6,6] system (e.g. decahydronaphthalene, norsabinane, norcarane). The term "bridged-bicyclic carbocycle" refers to a carbocycle bicyclic ring system wherein the rings of the bicyclic ring system are connected to two non-adjacent carbon (e.g. norbornane, bicyclo[2.2.2]octane, etc). The "carbocycle" or "carbocyclyl" may be optionally substituted with one or more (e.g. 1, 2 or 3)oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexa-1,3-dienyl, cycloheptanyl, cycloheptenyl, cyclohepta-1,3-dienyl, cyclohepta-1,4-dienyl, cyclooctyl, and cyclooctenyl rings.

Each carbocyclyl group may be substituted by 0, 1, 2, or 3 substituents independently selected from halogen, —OH, —CN, —$NO_2$, —$NH_2$, —NH($C_1$-$C_6$ alkyl), —N($C_1$-$C_6$ alkyl)$_2$, $C_1$-$C_6$ alkyl, $C_1$-$C_6$ alkoxy, and —$CF_3$.

The term "heteroaryl" as used herein refers to a single aromatic ring or a multiple condensed ring. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2 or 3 rings) wherein a heteroaryl group, as defined above, can be fused with one or more heteroaryls (e.g. naphthyridinyl), carbocycles (e.g. 5,6,7,8-tetrahydroquinolyl) or aryls (e.g. indazolyl) to form a multiple condensed ring. Such multiple condensed rings may be optionally substituted with one or more (e.g. 1, 2 or 3)oxo groups on the carbocycle portions of the condensed ring. It is to be understood that the point of attachment of a heteroaryl multiple condensed ring, as defined above, can be at any position of the ring including a heteroaryl, aryl or a carbocycle portion of the ring. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl and thionaphthenyl.

Each heteroaryl group may be substituted by 0, 1, 2, or 3 substituents independently selected from halogen, —OH, —CN, —$NO_2$, —$NH_2$, —NH($C_1$-$C_6$ alkyl), —N($C_1$-$C_6$ alkyl)$_2$, $C_1$-$C_6$ alkyl, $C_1$-$C_6$ alkoxy, and —$CF_3$.

"Heteroarylalkyl" refers to an alkyl radical as defined herein in which one of the hydrogen atoms bonded to a carbon atom is replaced with a heteroaryl radical as described herein (i.e., a heteroaryl-alkyl- moiety). The alkyl group of the "heteroarylalkyl" is typically 1 to 6 carbon atoms (i.e. heteroaryl($C_1$-$C_6$)alkyl). Heteroarylalkyl groups include, but are not limited to heteroaryl-$CH_2$—, heteroaryl-$CH(CH_3)$—, heteroaryl-$CH_2CH_2$—, 2-(heteroaryl)ethan-1-yl, and the like, wherein the "heteroaryl" portion includes any of the heteroaryl groups described above. One skilled in the art will also understand that the heteroaryl group can be attached to the alkyl portion of the heteroarylalkyl by means of a carbon-carbon bond or a carbon-heteroatom bond, with the proviso that the resulting group is chemically stable. Examples of heteroarylalkyls include by way of example and not limitation 5-membered sulfur, oxygen, and/or nitrogen containing heteroaryls such as thiazolylmethyl, 2-thiazolylethan-1-yl, imidazolylmethyl, oxazolylmethyl, thiadiazolylmethyl, etc., 6-membered sulfur, oxygen, and/or nitrogen containing heteroaryls such pyridinylmethyl, pyridizylmethyl, pyrimidylmethyl, pyrazinylmethyl, etc.

The heteroaryl ring of each of is the heteroarylalkyl group may be substituted by 0, 1, 2, or 3 substituents independently selected from halogen, —OH, —CN, —$NO_2$, —$NH_2$, —NH ($C_1$-$C_6$ alkyl), —N($C_1$-$C_6$ alkyl), $C_1$-$C_6$ alkyl, $C_1$-$C_6$ alkoxy, and —$CF_3$.

Any formula or structure given herein, including the compound of Formula I and pharmaceutically acceptable salts thereof, is also intended to represent unlabeled forms as well as isotopically labeled forms of the compounds, or salts thereof. Isotopically labeled compounds or salts thereof have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds or salts thereof of the present disclosure, for example those into which radioactive isotopes such as $^3H$, $^{13}C$ and $^{14}C$ are incorporated. Such isotopically labeled compounds or salts thereof may be useful in metabolic studies, reaction kinetic studies, detection or imaging techniques, such as positron emission tomography (PET) or single-photon emission computed tomography (SPECT) including drug or substrate tissue distribution assays or in radioactive treatment of subjects (e.g. humans).

The disclosure also includes the compound of Formula I and pharmaceutically acceptable salts thereof, in which from 1 to n hydrogens attached to a carbon atom is/are replaced by deuterium, in which n is the number of hydrogens in the molecule. Such compounds may exhibit increased resistance to metabolism and are thus useful for increasing the half-life of the compound of formula I, or pharmaceutically acceptable salts thereof when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index.

An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I and pharmaceutically acceptable salts thereof.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds or salts thereof of this disclosure any atom specifically designated as a deuterium (D) is meant to represent deuterium.

Pharmaceutical Formulations

Also provided herein is a pharmaceutical formulation comprising a pharmaceutically effective amount of a compound of Formula (I) or a pharmaceutically acceptable salt, solvate, and/or ester thereof, and a pharmaceutically acceptable carrier or excipient. Also provided are separate pharmaceutical formulations, each comprising a pharmaceutically effective amount of a compound of Formula (II), Formula (III), Formula (IV), Formula (V), Formula (VI), Formula (VII), Formula (VIII), and the specific compounds of the examples herein, or a pharmaceutically acceptable salt, solvate, and/or ester thereof, and a pharmaceutically acceptable carrier or excipient.

The compounds herein are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, comprise at least one active ingredient, as above defined, together with one or more acceptable carriers and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation include Tween® 60, Span® 80, cetostearyl alcohol, benzyl alcohol, myristyl alcohol, glyceryl monostearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations herein comprise a combination together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, solutions, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions may be in the form of a sterile injectable or intravenous preparations, such as a sterile injectable aqueous or oleaginous suspension. This suspension may be formulated according to the known art using those suitable dispersing or wetting agents and suspending agents which have been mentioned above. The sterile injectable or intravenous preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of Pneumovirinae infections as described below.

Another embodiment provides a novel, efficacious, safe, nonirritating and physiologically compatible inhalable composition comprising a compound of Formulas I-IX, or a pharmaceutically acceptable salt thereof, suitable for treating Pneumovirinae infections and potentially associated bronchiolitis. Preferred pharmaceutically acceptable salts are inorganic acid salts including hydrochloride, hydrobromide, sulfate or phosphate salts as they may cause less pulmonary irritation. Preferably, the inhalable formulation is delivered to the endobronchial space in an aerosol comprising particles with a mass median aerodynamic diameter (MMAD) between about 1 and about 5 μm. Preferably, the compound of Formulas I-IX is formulated for aerosol delivery using a nebulizer, pressurized metered dose inhaler (pMDI), or dry powder inhaler (DPI).

Non-limiting examples of nebulizers include atomizing, jet, ultrasonic, pressurized, vibrating porous plate, or equivalent nebulizers including those nebulizers utilizing adaptive aerosol delivery technology (Denyer, *J. Aerosol medicine Pulmonary Drug Delivery* 2010, 23 Supp 1, S1-S10). A jet nebulizer utilizes air pressure to break a liquid solution into aerosol droplets. An ultrasonic nebulizer works by a piezoelectric crystal that shears a liquid into small aerosol droplets. A pressurized nebulization system forces solution under pressure through small pores to generate aerosol droplets. A vibrating porous plate device utilizes rapid vibration to shear a stream of liquid into appropriate droplet sizes.

In a preferred embodiment, the formulation for nebulization is delivered to the endobronchial space in an aerosol comprising particles with a MMAD predominantly between about 1 μm and about 5 μm using a nebulizer able to aerosolize the formulation of the compound of Formulas I-IX into particles of the required MMAD. To be optimally therapeutically effective and to avoid upper respiratory and systemic side effects, the majority of aerosolized particles should not have a MMAD greater than about 5 μm. If an aerosol contains a large number of particles with a MMAD larger than 5 μm, the particles are deposited in the upper airways decreasing the amount of drug delivered to the site of inflammation and bronchoconstriction in the lower respiratory tract. If the MMAD of the aerosol is smaller than about 1 μm, then the particles have a tendency to remain suspended in the inhaled air and are subsequently exhaled during expiration.

When formulated and delivered according to the method herein, the aerosol formulation for nebulization delivers a therapeutically efficacious dose of the compound of Formulas I-IX to the site of Pneumovirinae infection sufficient to treat the Pneumovirinae infection. The amount of drug administered must be adjusted to reflect the efficiency of the delivery of a therapeutically efficacious dose of the compound of Formulas I-IX. In a preferred embodiment, a combination of the aqueous aerosol formulation with the atomizing, jet, pressurized, vibrating porous plate, or ultrasonic nebulizer permits, depending on the nebulizer, about, at least, 20, to about 90%, typically about 70% delivery of the administered dose of the compound of Formulas I-IX into the airways. In a preferred embodiment, at least about 30 to about 50% of the active compound is delivered. More preferably, about 70 to about 90% of the active compound is delivered.

In another embodiment, a compound of Formulas I-IX or a pharmaceutically acceptable salt thereof, is delivered as a dry inhalable powder. The compounds are administered endobronchially as a dry powder formulation to efficacious deliver fine particles of compound into the endobronchial space using dry powder or metered dose inhalers. For delivery by DPI, the compound of Formulas I-IX is processed into particles with, predominantly, MMAD between about 1 μm and about 5 μm by milling spray drying, critical fluid processing, or precipitation from solution. Media milling, jet milling and spray-drying devices and procedures capable of producing the particle sizes with a MMAD between about 1 μm and about 5 μm are well known in the art. In one embodiment, excipients are added to the compound of Formulas I-IX before processing into particles of the required sizes. In another embodiment, excipients are blended with the particles of the required size to aid in dispersion of the drug particles, for example by using lactose as an excipient.

Particle size determinations are made using devices well known in the art. For example a multi-stage Anderson cascade impactor or other suitable method such as those specifically cited within the US Pharmacopoeia Chapter 601 as characterizing devices for aerosols within metered-dose and dry powder inhalers.

In another preferred embodiment, a compound of Formulas I-IX is delivered as a dry powder using a device such as a dry powder inhaler or other dry powder dispersion devices. Non-limiting examples of dry powder inhalers and devices include those disclosed in U.S. Pat. No. 5,458,135; U.S. Pat. No. 5,740,794; U.S. Pat. No. 5,775,320; U.S. Pat. No. 5,785,049; U.S. Pat. No. 3,906,950; U.S. Pat. No. 4,013,075; U.S. Pat. No. 4,069,819; U.S. Pat. No. 4,995,385; U.S. Pat. No. 5,522,385; U.S. Pat. No. 4,668,218; U.S. Pat. No. 4,667,668; U.S. Pat. No. 4,805,811 and U.S. Pat. No. 5,388,572. There are two major designs of dry powder inhalers. One design is a metering device in which a reservoir for the drug is place within the device and the patient adds a dose of the drug into the inhalation chamber. The second design is a factory-metered device in which each individual dose has been manufactured in a separate container. Both systems depend on the formulation of the drug into small particles of MMAD from 1 μm and about 5 μm and often involve co-formulation with larger excipient particles such as, but not limited to, lactose. Drug powder is placed in the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs. In preferred embodiments, a compound of Formulas I-IX, or a pharmaceutically acceptable salt thereof, is delivered as a dry powder using either type of dry powder inhaler as described herein, wherein the MMAD of the dry powder, exclusive of any excipients, is predominantly in the range of 1 μm to about 5 μm.

In another embodiment, a compound of Formulas I-IX is delivered as a dry powder using a metered dose inhaler. Non-limiting examples of metered dose inhalers and devices include those disclosed in U.S. Pat. No. 5,261,538; U.S. Pat. No. 5,544,647; U.S. Pat. No. 5,622,163; U.S. Pat. No. 4,955,371; U.S. Pat. No. 3,565,070; U.S. Pat. No. 3,361,306 and U.S. Pat. No. 6,116,234. In preferred embodiments, a compound of Formulas I-IX, or a pharmaceutically acceptable salt thereof, is delivered as a dry powder using a metered dose inhaler wherein the MMAD of the dry powder, exclusive of any excipients, is predominantly in the range of about 1-5 μm.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations may include other agents conventional in the art having regard to the type of formulation in question, for example those suitable for oral administration may include flavoring agents.

Further provided are veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds herein are used to provide controlled release pharmaceutical formulations containing as active ingredient one or more of the compounds ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more of the compounds (herein referred to as the active ingredients) are administered by any route appropriate to the condition to be treated. Suitable routes include oral, rectal, nasal, pulmonary, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds herein is that they are orally bioavailable and can be dosed orally.

Combination Therapy

Compositions are also used in combination with other active ingredients. For the treatment of Pneumovirinae virus infections, preferably, the other active therapeutic agent is active against Pneumovirinae virus infections, particularly respiratory syncytial virus infections. Non-limiting examples of these other active therapeutic agents are ribavirin, palivizumab, motavizumab, RSV-IGIV (RespiGam), MEDI-557, A-60444 (also known as RSV604), MDT-637, BMS-433771, ALN-RSV0, ALX-0171 and mixtures thereof.

Many of the infections of the Pneumovirinae viruses are respiratory infections. Therefore, additional active therapeutics used to treat respiratory symptoms and sequelae of infection may be used in combination with the compounds of Formulas I-IX. The additional agents are preferably administered orally or by direct inhalation. For example, other preferred additional therapeutic agents in combination with the compounds of Formulas I-IX for the treatment of viral respiratory infections include, but are not limited to, bronchodilators and corticosteroids.

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compounds of Formulas I-IX are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone propionate, ciclesonide; or a pharmaceutically acceptable salts thereof.

Other anti-inflammatory agents working through anti-inflammatory cascade mechanisms are also useful as additional therapeutic agents in combination with the compounds of Formulas I-IX for the treatment of viral respiratory infections. Applying "anti-inflammatory signal transduction modulators" (referred to in this text as AISTM), like phosphodiesterase inhibitors (e.g. PDE-4, PDE-5, or PDE-7 specific), transcription factor inhibitors (e.g. blocking NFκB through IKK inhibition), or kinase inhibitors (e.g. blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluorophenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

Combinations comprising inhaled β2-adrenoreceptor agonist bronchodilators such as formoterol, albuterol or salmeterol with the compounds of Formulas I-IX are also suitable, but non-limiting, combinations useful for the treatment of respiratory viral infections.

Combinations of inhaled β2-adrenoreceptor agonist bronchodilators such as formoterol or salmeterol with ICS's are also used to treat both the bronchoconstriction and the inflammation (Symbicort® and Advair®, respectively). The combinations comprising these ICS and β2-adrenoreceptor agonist combinations along with the compounds of Formulas I-IX are also suitable, but non-limiting, combinations useful for the treatment of respiratory viral infections.

For the treatment or prophylaxis of pulmonary bronchoconstriction, anticholinergics are of potential use and, therefore, useful as an additional therapeutic agents in combination with the compounds of Formulas I-IX for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo [3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester.

The compounds of Formulas I-IX may also be combined with mucolytic agents to treat both the infection and symptoms of respiratory infections. A non-limiting example of a mucolytic agent is ambroxol. Similarly, the compounds of Formulas I-IX may be combined with expectorants to treat both the infection and symptoms of respiratory infections. A non-limiting example of an expectorant is guaifenesin.

Nebulized hypertonic saline is used to improve immediate and long-term clearance of small airways in patients with lung diseases (Kuzik, *J. Pediatrics* 2007, 266). The compounds of Formulas I-IX may also be combined with nebulized hypertonic saline particularly when the Pneumovirinae virus infection is complicated with bronchiolitis. The combination of the compounds of Formulas I-IX with hypertonic saline may also comprise any of the additional agents discussed above. In one embodiment, nebulized about 3% hypertonic saline is used.

It is also possible to combine any compound with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound herein with one or more other active therapeutic agents generally refers to simultaneous or sequential administration of a compound and one or more other active therapeutic agents, such that therapeutically effective amounts of the compound and one or more other active therapeutic agents are both present in the body of the patient.

Co-administration includes administration of unit dosages of the compounds before or after administration of unit dosages of one or more other active therapeutic agents, for example, administration of the compounds within seconds, minutes, or hours of the administration of one or more other active therapeutic agents. For example, a unit dose of a compound can be administered first, followed within seconds or minutes by administration of a unit dose of one or more other active therapeutic agents. Alternatively, a unit dose of one or more other therapeutic agents can be administered first, followed by administration of a unit dose of a compound within seconds or minutes. In some cases, it may be desirable to administer a unit dose of a compound first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound herein.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-viral effect denotes an antiviral effect which is greater than the predicted purely additive effects of the individual compounds of the combination.

In still yet another embodiment, the present application provides a method of treating Pneumovirinae virus infection in a human, the method comprising administering to the human a therapeutically effective amount of a compound of Formula (I), or a pharmaceutically acceptable salt, solvate, and/or ester thereof. Also provided are separate methods of treating Pneumovirinae virus infection in a human, each comprising administering to the human a therapeutically effective a pharmaceutically effective amount of a compound of Formula (II), Formula (III), Formula (IV), Formula (V), Formula (VI), Formula (VII), Formula (VIII), Formula (IX), or one of the specific compounds of the examples herein, or a pharmaceutically acceptable salt, solvate, and/or ester thereof, and a pharmaceutically acceptable carrier or excipient.

In another embodiment, provided is a method of treating a Pneumovirinae infection in a human by administering to the human a therapeutically effective amount of a racemate, enantiomer, diastereomer, tautomer, polymorph, pseudopolymorph, amorphous form, hydrate or solvate of a compound of a compound of Formula (I), or a pharmaceutically acceptable salt or ester thereof.

Further provided are separate methods of treating a Pneumovirinae infection in a human in need thereof, each method comprising administering to the human a therapeutically effective amount of a racemate, enantiomer, diastereomer, tautomer, polymorph, pseudopolymorph, amorphous form, hydrate or solvate of a compound of Formula (II), Formula (III), Formula (IV), Formula (V), Formula (VI), Formula (VII), Formula (VIII), Formula (IX), or one of the specific compounds of the examples herein, or a pharmaceutically acceptable salt, solvate, and/or ester thereof.

In still yet another embodiment, the present application provides for a method of treating human respiratory syncytial virus infection in a human, the method comprising administering to the human a therapeutically effective amount of a compound of Formula (I), or a pharmaceutically acceptable salt, solvate, and/or ester thereof.

In still yet another embodiment, the present application provides for a method of treating human respiratory syncytial virus infection in a human, the method comprising administering to the human a therapeutically effective amount of a compound of Formula (I), or a pharmaceutically acceptable salt, solvate, and/or ester thereof, and at least one additional active therapeutic agent.

Further provided are separate methods of treating a human respiratory syncytial virus infection in a human in need thereof, each method comprising administering to the human a therapeutically effective amount of a compound of Formula (II), Formula (III), Formula (IV), Formula (V), Formula (VI), Formula (VII), Formula (VIII), Formula (IX), or one of the specific compounds of the examples herein, or a pharmaceutically acceptable salt, solvate, and/or ester thereof.

Also provided are separate methods of treating a human respiratory syncytial virus infection in a human in need thereof, each method comprising administering to the human a therapeutically effective amount of a compound of Formula (II), Formula (III), Formula (IV), Formula (V), Formula (VI), Formula (VII), Formula (VIII), Formula (IX), or one of the specific compounds of the examples herein, or a pharmaceutically acceptable salt, solvate, and/or ester thereof, and at least one additional active therapeutic agent.

Also provided are separate methods of treating a human respiratory syncytial virus infection in a human in need thereof, wherein the human is also experiencing bronchiolitis, each method comprising administering to the human a therapeutically effective amount of a compound of Formula (I), Formula (II), Formula (III), Formula (IV), Formula (V), Formula (VI), Formula (VII), Formula (VIII), Formula (IX), or one of the specific compounds of the examples herein, or a pharmaceutically acceptable salt, solvate, and/or ester thereof.

Also provided are separate methods of treating a human respiratory syncytial virus infection in a human in need thereof, wherein the human is also experiencing pneumonia, each method comprising administering to the human a therapeutically effective amount of a compound of Formula (I), Formula (II), Formula (III), Formula (IV), Formula (V), Formula (VI), Formula (VII), Formula (VIII), Formula (IX), or one of the specific compounds of the examples herein, or a pharmaceutically acceptable salt, solvate, and/or ester thereof.

Also provided are separate methods of improving respiratory symptoms in a human experiencing a human respiratory syncytial virus infection, each method comprising administering to the human a therapeutically effective amount of a compound of Formula (I), Formula (II), Formula (III), Formula (IV), Formula (V), Formula (VI), Formula (VII), Formula (VIII), Formula (IX), or one of the specific compounds of the examples herein, or a pharmaceutically acceptable salt, solvate, and/or ester thereof.

Respiratory symptoms in a human experiencing a respiratory syncytial virus infection may include congested or runny nose, coughing, wheezing, sneezing, rapid breathing or difficulty breathing, apnea, bronchiolitis, and pneumonia.

Also provided is an embodiment comprising the use of a compound of Formula (I), or a pharmaceutically acceptable salt, solvate, and/or ester thereof, for the manufacture of a medicament for the treatment of a Pneumovirinae virus infection or a respiratory syncytial virus infection in a human.

Also provided is an embodiment comprising the use of a compound of Formula (II), Formula (III), Formula (IV), Formula (V), Formula (VI), Formula (VII), Formula (VIII), Formula (IX), or one of the specific compounds of the examples herein, or a pharmaceutically acceptable salt, solvate, and/or ester thereof, for the manufacture of a medicament for the treatment of a Pneumovirinae virus infection or a respiratory syncytial virus infection in a human.

Also provided is a pharmaceutical formulation comprising a pharmaceutically effective amount of a compound of Formula (I), or a pharmaceutically acceptable salt, solvate, and/or ester thereof, and a pharmaceutically acceptable carrier or excipient. Further provided is a pharmaceutical formulation comprising a pharmaceutically effective amount of a compound of Formula (II), Formula (III), Formula (IV), Formula (V), Formula (VI), Formula (VII), Formula (VIII), Formula (IX), or one of the specific compounds of the examples herein, or a pharmaceutically acceptable salt, solvate, and/or ester thereof, and a pharmaceutically acceptable carrier or excipient.

Also provided is a pharmaceutical formulation comprising a pharmaceutically effective amount of a compound of Formula (I), or a pharmaceutically acceptable salt, solvate, and/or ester thereof, and a pharmaceutically acceptable carrier or excipient and a pharmaceutically effective amount of at least one additional active therapeutic agent. Further provided is a pharmaceutical formulation comprising a pharmaceutically effective amount of a compound of Formula (II), Formula (III), Formula (IV), Formula (V), Formula (VI), Formula (VII), Formula (VIII), Formula (IX), or one of the specific compounds of the examples herein, or a pharmaceutically acceptable salt, solvate, and/or ester thereof, and a pharmaceutically acceptable carrier or excipient and a pharmaceutically effective amount of at least one additional active therapeutic agent.

Also provided are separate embodiments comprising a compound of Formula (I), Formula (II), Formula (III), Formula (IV), Formula (V), Formula (VI), Formula (VII), Formula (VIII), Formula (IX), or one of the specific compounds of the examples herein, or a pharmaceutically acceptable salt, solvate, and/or ester thereof, for use in the treatment of a Pneumovirinae virus infection or a respiratory syncytial virus infection in a human.

Also provided are separate embodiments comprising a compound of Formula (I), Formula (II), Formula (III), Formula (IV), Formula (V), Formula (VI), Formula (VII), Formula (VIII), Formula (IX), or one of the specific compounds of the examples herein, or a pharmaceutically acceptable salt, solvate, and/or ester thereof, for use as a medicament.

Also provided are separate embodiments comprising a method for manufacturing a medicament intended for treatment of a Pneumovirinae virus infection or a respiratory syncytial virus infection in a human, characterised in that a compound of Formula (I), Formula (II), Formula (III), Formula (IV), Formula (V), Formula (VI), Formula (VII), Formula (VIII), Formula (IX), or one of the specific compounds of the examples herein, or a pharmaceutically acceptable salt, solvate, and/or ester thereof, is used.

Also provided is a compound of Formula (I), or a pharmaceutically acceptable salt, solvate, and/or ester thereof, for the treatment of a Pneumovirinae virus infection or a respiratory syncytial virus infection in a human.

Also provided are separate embodiments comprising that a compound of Formula (II), Formula (III), Formula (IV), Formula (V), Formula (VI), Formula (VII), Formula (VIII), Formula (IX), or one of the specific compounds of the examples herein, or a pharmaceutically acceptable salt, solvate, and/or ester thereof, for the treatment of a Pneumovirinae virus infection or a respiratory syncytial virus infection in a human.

Further provided is a compound as described in this specification. Also provided is a pharmaceutical composition as described in this specification. Also provided is a method of using a compound of Formula (I), as described in this specification. Further provided is a method of making a compound of Formula (I), as described in this specification.

Metabolites of the Compounds

Also falling within the scope herein are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, included are novel and unobvious compounds produced by a process comprising contacting a compound with a mammal for a period of time sufficient to yield a metabolic product thereof. Such products typically are identified by preparing a radiolabelled (e.g. $^{14}$C or $^3$H) compound, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds even if they possess no HSV antiviral activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs typically will be stable in the digestive system but may be substantially hydrolyzed to the parental drug in the digestive lumen, liver, lung or other metabolic organ, or within cells in general. As used herein, a prodrug is understood to be a compound that is chemically designed to efficiently liberate the parent drug after overcoming biological barriers to oral delivery.

Useful oxygen protecting groups include a silyl ether protecting group or a benzyl-type protecting group, including methoxybenzyl groups.

Useful silyl ether protecting groups include Trimethylsilyl (TMS), Triethylsilyl (TES), Dimethylisopropylsilyl (IP-DMS), Diethylisopropylsilyl (DEIPS), Dimethylthexylsilyl (TDS), t-Butyldimethylsilyl (TBS or TBDMS), t-Butyldiphenylsilyl (TBDPS), Tribenzylsilyl, Tri-p-xylylxilyl, Triisopropylsilyl (TIPS), Diphenylmethylsilyl (DPMS), Di-t-butylmethylsilyl (DTBMS), Triphenylsilyl (TPS), Methyldiphenylsilyl (MDPS), t-butylmethoxyphenylsilyl, Tris(trimethylsilyl)silyl (sisyl), (2-Hydroxystyryl)dimethylsilyl (HSDMS), (2-Hydroxystyryl)diisopropylsilyl (HSDIS). t-Butylmethoxyphenylsilyl (TBMPS), and t-Butoxydiphenylsilyl (DPTBOS) protecting groups.

Useful benzyl-type protecting groups include benzyl, halogenated benzyl, p-methoxybenzyl, benzyloxymethyl, 2,4-dimethoxybenzyl, 3,4-dimethoxybenzyl, 2,6-dimethoxybenzyl, p-CF$_3$-benzyl, p-methylbenzyl, p-methoxylbenzyl, 3,5-dimethylbenzyl, p-tert-butylbenzyl, o-nitrobenzyl, p-nitrobenzyl, p-halobenzyl, including p-Br-benzyl, 2,6-dichlorobenzyl, p-cyanobenzyl, p-phenylbenzyl, 2,6-difluorobenzyl, p-acylaminobenzyl (PAB), p-azidobenzyl (Azb), 4-azido-3-chlorobenzyl, 2-trifluoromethylbenzyl, p-(methylsulfinyl)benzyl, 2-picolyl, 4-picolyl, 3-methyl-2-picolyl N-oxido, 2-quinolinylmethyl, diphenylmethyl (DPM), p,p'-dinitrobenzhydryl, triphenylmethyl, alpha-naphthyldiphenylmethyl, p-methoxyphenyldiphenylmethyl, di(p-methoxyphenyl)phenylmethyl, tri(p-methoxyphenyl)methyl, 4,4',4"-tris(benzoyloxyphenyl)methyl, and 2-naphthylmethyl protecting groups.

Useful amine protecting groups include p-methoxybenzyl carbonyl (Moz or MeOZ), acetyl (Ac), benzoyl (Bz), p-methoxybenzyl (PMB), 3,4-dimethoxybenzyl (DMPM), p-methoxyphenyl (PMP), tosyl (Ts or Tos), trifluoroacetamide, and trityl protecting groups.

Useful amine protecting groups also include carbamate and amide protecting groups. Examples of carbamate protecting groups include methyl and ethyl carbamates such as 9-fluorenylmethyloxycarbonyl (FMOC), 9-(2-sulfo)fluorenylmethyl, 9-(2,7-dibromo)fluorenylmethyl, 17-tetrabenzo[a,c,g,i]fluorenylmethyl (Tbfmoc), 2-chloro-3-indenylmethyl (Climoc), benz Minden-3-ylmethyl (Bimoc), 2,7-di-t-butyl[9-(10,10-dioxo-10,10,10,10-tetrahydrothioxanyl)]methyl (DBD-Tmoc), [2-(1,3-dithianyl)methyl (Dmoc), and 1,1-dioxobenzo[b]thiophene-2-ylmethyl (Bsmoc) carbamates.

Examples of useful substituted ethyl carbamates include 1,1-dimethyl-2-cyanoethyl, 2-phosphonioethyl (Peoc), 2-methylthioethyl, 2-(p-toluenesulfonyl)ethyl, 2,2,2,-trichloroethyl (Troc), 2-(trimethylsilyl)ethyl (Teoc), 2-phenylethyl (hZ), 1-(1-adamantyl)-1-methylethyl (Adpoc), 1,1-dimethyl-2-bromoethyl, 1,1-dimethyl-2-chloroethyl, 1,1-dimethyl-2,2-dibromoethyl (DB-t-BOC), 1,1-dimethyl-2,2,2-trichloroethyl (TCBOC), 1-methyl-1-(4-biphenylyl)ethyl (Bpoc), 1-(3,5-di-t-butylphenyl)-1-methylethyl (t-Bumeoc), 2-(2'pyridyl)ethyl, 2-(4'pyridyl)ethyl, 2,2-bis(4'-nitrophenyl)ethyl (Bnpeoc), N-(2-pivaloylamino)-1,1,dimethylethyl, 2-[(2-nitrophenyl)dithio]-1-phenylethyl (NpSSPeoc), 2-(N,N-dicyclohexylcarboxamido)ethyl, t-butyl (Boc or BOC), 1-adamantyl (1-Adoc), 2-adamantyl (2-Adoc), vinyl (Voc), allyl (Aloc or alloc), 1-isopropylallyl (Ipaoc), cinnamyl (Coc), 4-nitrocinnamyl (Noc), 3-(3'-pyridyl)prop-2-enyl (Paloc), 8-quinolyl, and N-hydroxypiperidinyl, carbamates, as well as alkyldithio carbamates, including methyldithio, ethyldithio, isopropyldithio, t-butyldithio, and phenyldithio carbamates.

Also useful are aryl-containing and substituted aryl-containing carbamates such as benzyl, p-methoxybenzyl, p-nitrobenzyl, p-bromobenzyl, p-chlorobenzyl, 2,4-dichlorobenzyl, 4-methylsulfinylbenzyl (Msz), 9-anthrylmethyl, 4-methylthiophenyl (Mtpc), 1-methyl-1-(triphenylphosphonio)ethyl (2-triphenylphosphonioisopropyl) (Ppoc), 2-dansylethyl (Dnseoc), 2-(4-nitrophenyl)ethyl (Npeoc), 4-phenylacetoxybenzyl (PhAcOZ), 4-azidobenzyl (ACBZ), 4-azidomethoxybenzyl, m-chloro-p-acyloxybenzyl, p-(dihydroxyboryl)benzyl, carbobenzyloxy (Cbz), 4-benzisoxazolylmethyl (Bic), 2-(trifluoromethyl)-6-chromonylmethyl (Tcroc), phenyl, and diphenylmethyl carbamates. Additional carbamates include butynyl, cyclopentyl, cyclohexyl, cyclopropylmethyl, 1-methylcyclobutyl, 1-methylcyclohexyl, 1,1-dimethylpropynyl, and 1-methyl-1-cyclopropylmethyl carbamates.

Useful amide protecting groups for amines include N-formyl, N-acetyl, N-chloroacetyl, N-trichloroacetyl, N-trifluoroacetyl (TFA), N-phenylacetyl, N-3-phenylpropionyl, N-4-pentenoyl, N-picolinoyl, N-3-pyridylcarboxamido, N-benzoylphenylalanyl, N-benzoyl, and N-p-phenylbenzoyl amides.

TABLE 1

List of abbreviations and acronyms.

| Abbreviation | Meaning |
|---|---|
| Ac | acetate |
| ACN | acetonitrile |
| AIBN | azobisisobutyronitrile |
| Bn | benzyl |
| Bu | butyl |
| Bz | benzoyl |
| BzCl | benzoyl chloride |
| CDI | 1,1'-carbonyldiimidazole |
| DAST | diethylaminosulfur trifluoride |
| DBU | 1,8-diazabicycloundec-7-ene |
| DCE | 1,2-dichloroethane |
| DCM | dichloromethane |
| DMAP | 4-dimethylaminopyridine |
| DMDO | dimethydioxirane |
| DMSO | dimethylsulfoxide |
| DMF | dimethylformamide |
| DMTrCl | 4,4'-dimethoxytritylchloride |
| DMTr | 4,4'-dimethoxytrityl |
| EDCI | N-(3-dimethylaminopropyl)-N'-ethylcarbodiimide hydrochloride |
| Et | ethyl |
| Imid | imidazole |
| KOtBu | potassium tert-butoxide |
| LC | liquid chromatography |
| MCBA | meta-chlorobenzoic acid |
| MCPBA | meta-chloroperbenzoic acid |
| Me | methyl |
| m/z | mass to charge ratio |
| MS or ms | mass spectrometry |
| NIS | N-iodosuccinimide |
| NMP | N-methyl-2-pyrrolidone |
| PDC | pyridinium chlorochromate |
| Ph | phenyl |
| Ph$_3$P | triphenylphosphine |
| PMB | para-methoxybenzyl |
| PMBCl | para-methoxybenzyl chloride |
| PhOC(S)Cl | phenylchlorothionoformate |
| (PhO)$_3$PMeI | methyltriphenoxyphosphonium iodide |
| PTSA | para-toluenesulfonic acid |
| Py | pyridine |
| RT | room temperature |
| TBAF | tetrabutylammonium flouride |
| TBS | tert-butyldimethylsilyl |
| TBSCl | tert-Butyldimethylsilyl chloride |
| TMSN$_3$ | trimethylsilyl azide |
| TEA | triethylamine |
| TES | triethysilane |
| TFA | trifluoroacetic acid |
| THF | tetrahydrofuran |
| TMS | trimethylsilyl |
| TMSCl | trimethylsilyl chloride |
| Ts | 4-toluenesulfonyl |
| TsOH | tosylic acid |
| δ | parts per million referenced to residual non-deuterated solvent peak |

General Schemes

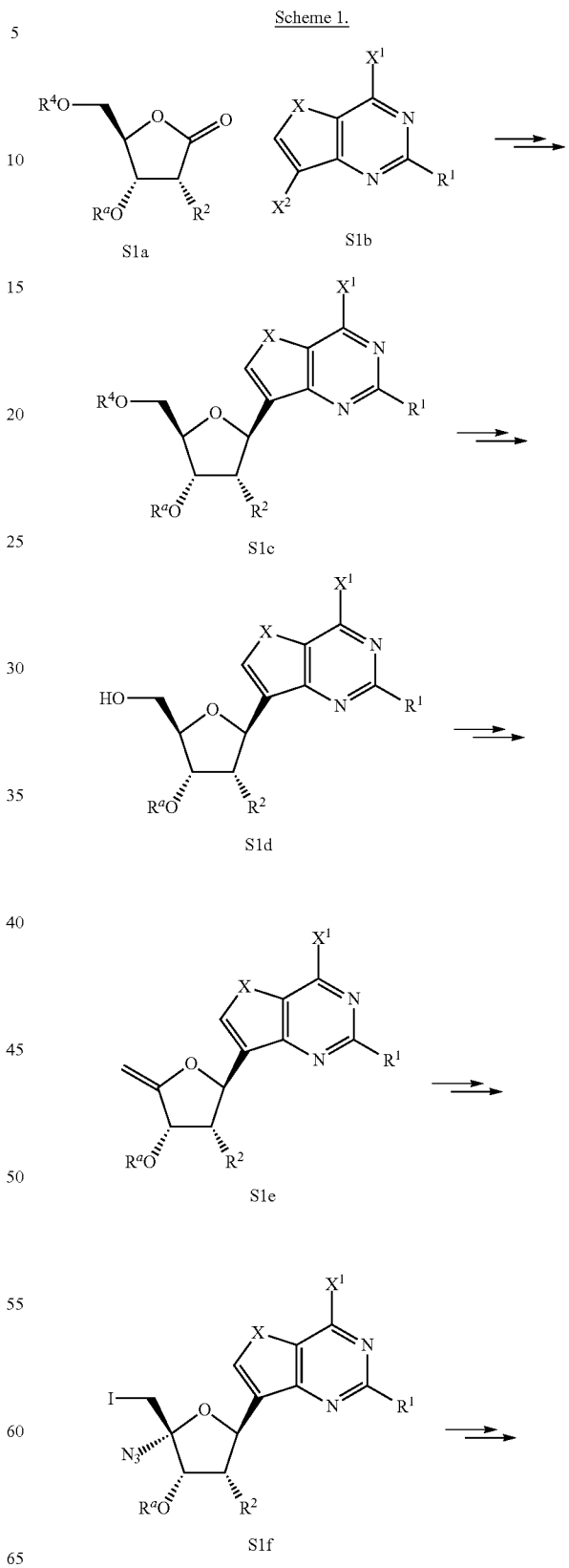

Scheme 1.

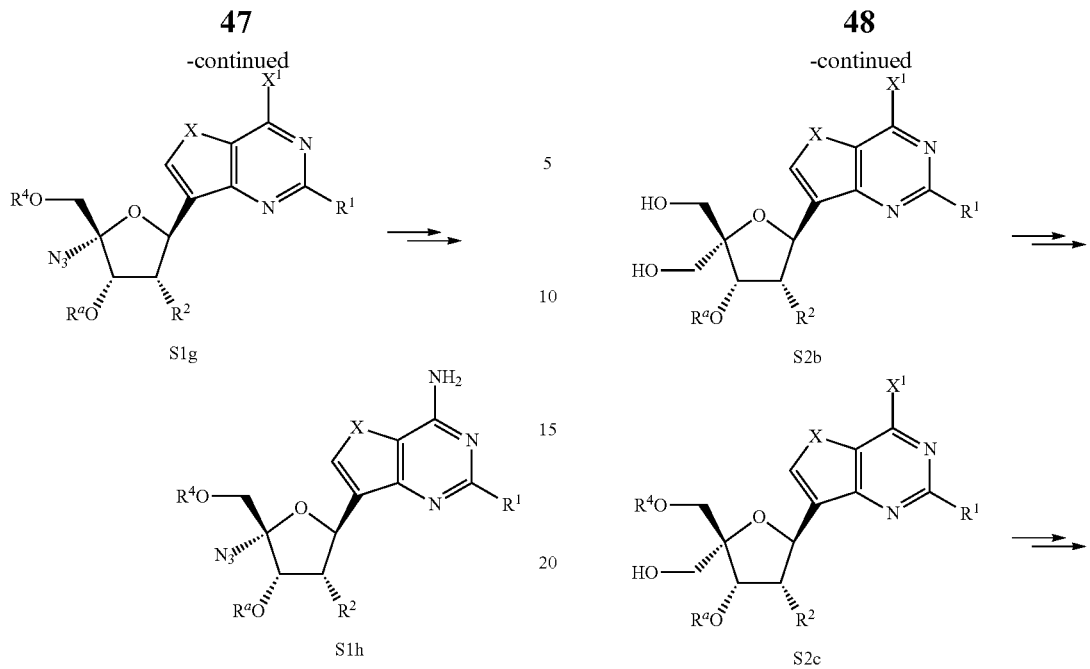

Scheme 1 shows a general synthesis of compounds of the invention beginning with a lithium-halogen exchange (e.g. n-BuLi) reaction with an appropriate nucleobase S1b ($X^1$=halogen, —O—alkyl, —O-Aryl, —S-Alkyl, —S-Aryl, $NH_2$, $NHR^a$, $NR^a_2$; $X^2$=Br, I) followed by addition to the lactone S1a. Reduction of the pendant 1' hydroxyl group under Lewis acidic conditions (e.g. $BF_3.Et_2O$, $Et_3SiH$) generates intermediate S1c. Standard alterations of the hydroxyl protecting groups afford the appropriately protected intermediate S1d. The 5' hydroxyl group of S1d is then converted to the corresponding iodide (e.g. $I_2$, $PPh_3$), which is then treated with basic conditions (e.g. DBU) to effect an elimination reaction generating intermediate S1e. Oxidation of the olefin S1e and azide addition (e.g. ICl, $NaN_3$) affords intermediate S1f. Displacement of the iodide S1f with an oxygen nucleophile (e.g. MCPBA, MCBA) generates S1g, and conversion of the $X^1$ group to an —$NH_2$ (e.g. $NH_4OH$) yields the final compounds of the type S1h.

Scheme 2.

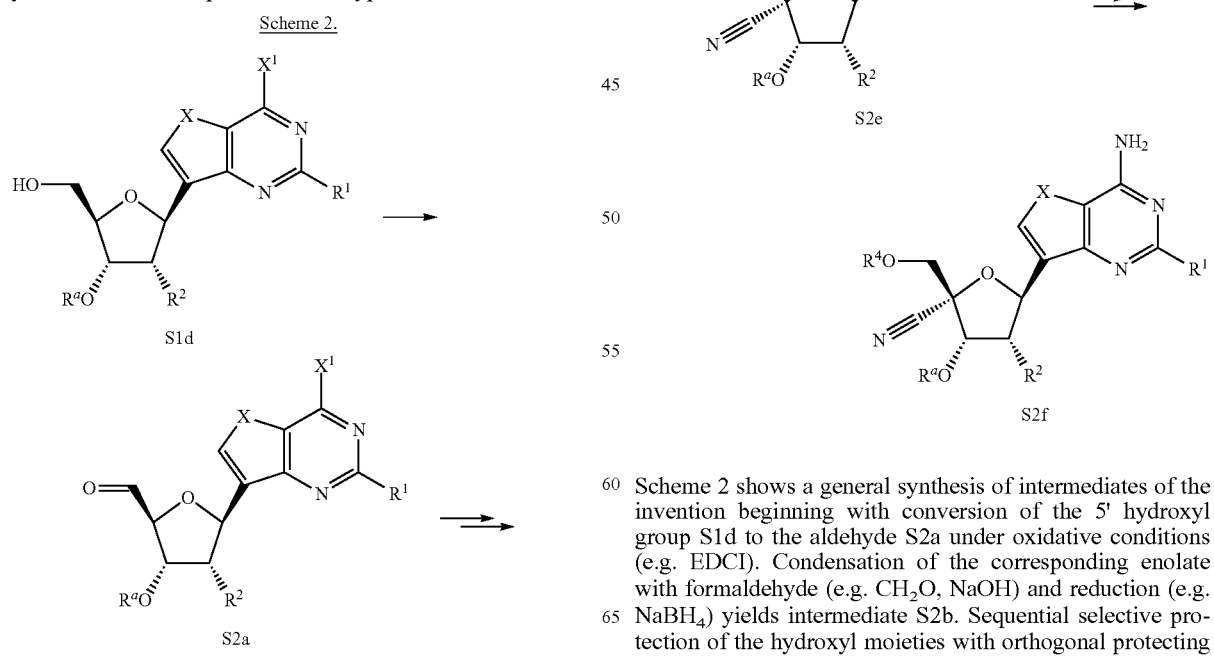

Scheme 2 shows a general synthesis of intermediates of the invention beginning with conversion of the 5' hydroxyl group S1d to the aldehyde S2a under oxidative conditions (e.g. EDCI). Condensation of the corresponding enolate with formaldehyde (e.g. $CH_2O$, NaOH) and reduction (e.g. $NaBH_4$) yields intermediate S2b. Sequential selective protection of the hydroxyl moieties with orthogonal protecting groups affords intermediate S2c. Conversion of the hydroxyl group S2c to the aldehyde under oxidative conditions (e.g. EDCI) generates intermediate S2d. Elaboration of the aldehyde S2d to the nitrile S2e can be effected through oxime formation (e.g. NH$_2$OH), and elimination of the oxime alcohol (e.g. CDI). Conversion of the X$^1$ group to an —NH$_2$ (e.g. NH$_4$OH) yields the final compounds of the type S2f.

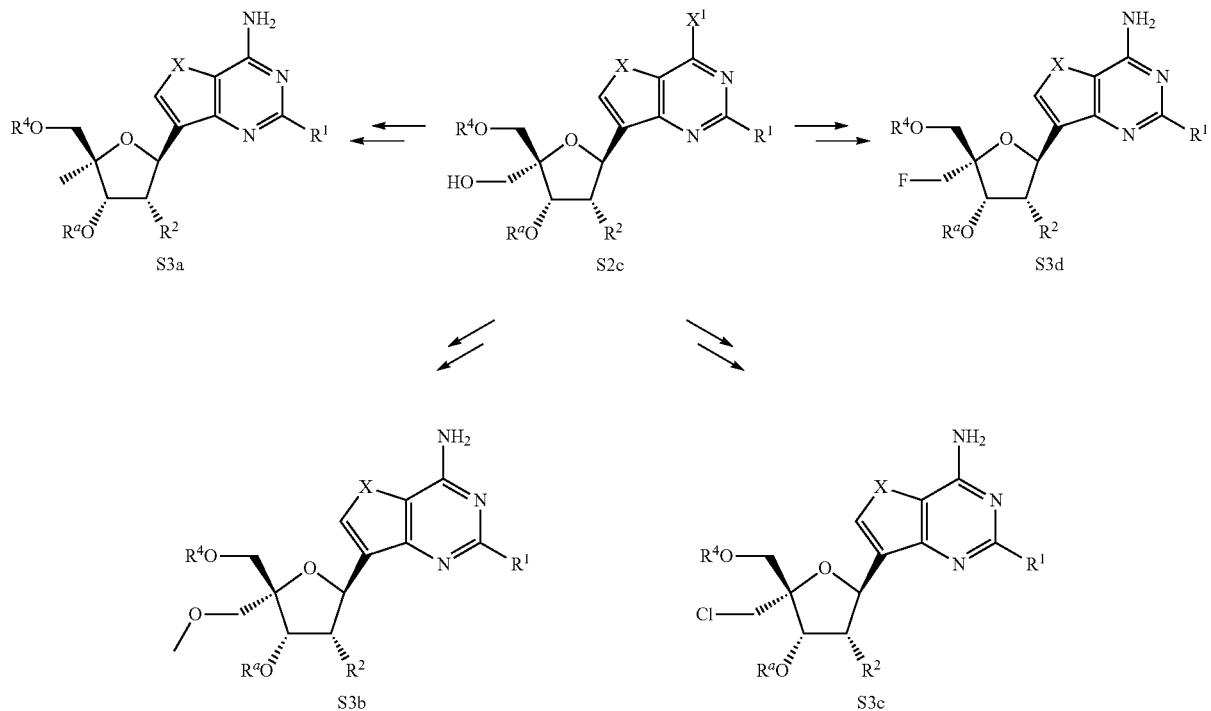

Scheme 3.

Scheme 3 shows a general synthesis of intermediates of the invention through elaboration of the alcohol S2c. Deoxygenatrion of the alcohol S2c (e.g. PPh$_3$, I$_2$, then Bu$_3$SnH, AIBN), and conversion of the X$^1$ group to an —NH$_2$ (e.g. NH$_4$OH) yields the final compounds of the type S3a. Methylation of the alcohol S2c (e.g. MeI), and conversion of the X$^1$ group to an —NH$_2$ (e.g. NH$_4$OH) yields the final compounds of the type S3b. Chlorination of the alcohol S2c (e.g. POCl$_3$), and conversion of the X$^1$ group to an —NH$_2$ (e.g. NH$_4$OH) yields the final compounds of the type S3c. Fluorination of the alcohol S2c (e.g. DAST), and conversion of the X$^1$ group to an —NH$_2$ (e.g. NH$_4$OH) yields the final compounds of the type S3d.

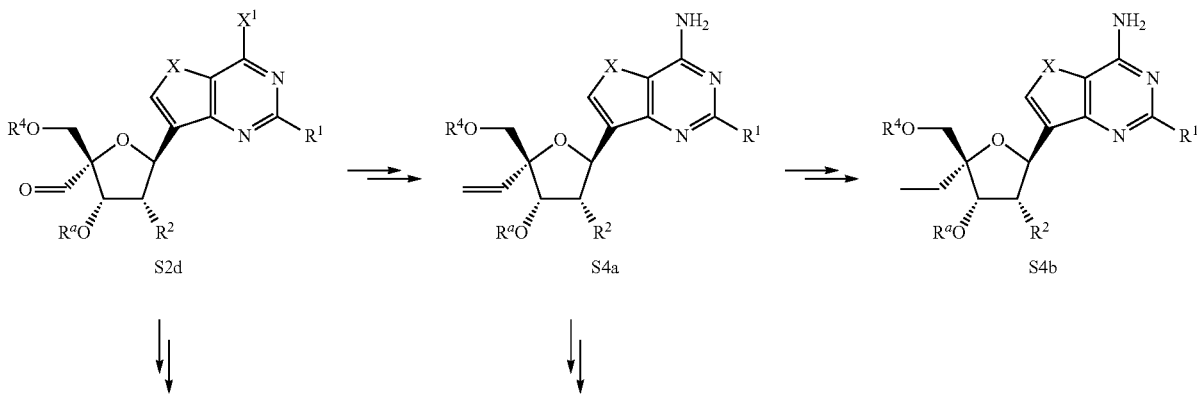

Scheme 4.

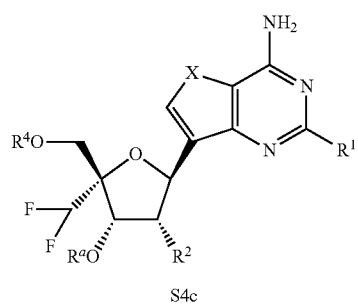
S4c

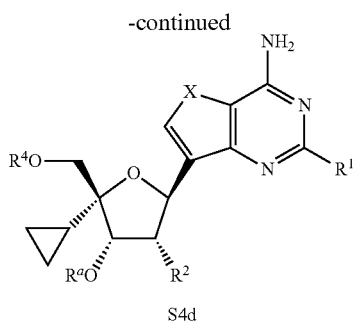
S4d

Scheme 4 shows a general synthesis of intermediates of the invention through elaboration of the aldehyde S2d. Olefination of the aldehyde S2d (e.g. Ph₃PCH₂), and conversion of the $X^1$ group to an —NH₂ (e.g. NH₄OH) yields the final compounds of the type S4a. Reduction of the olefin (e.g. H₂, Pd/C) yields the final compounds of the type S4b. Difluorination of the aldehyde S2d (e.g. DAST), and conversion of the $X^1$ group to an —NH₂ (e.g. NH₄OH) yields the final compounds of the type S4c. Cyclopropination of the olefin S4a (e.g. CH₂N₂), and conversion of the $X^1$ group to an —NH₂ (e.g. NH₄OH) yields the final compounds of the type S4d.

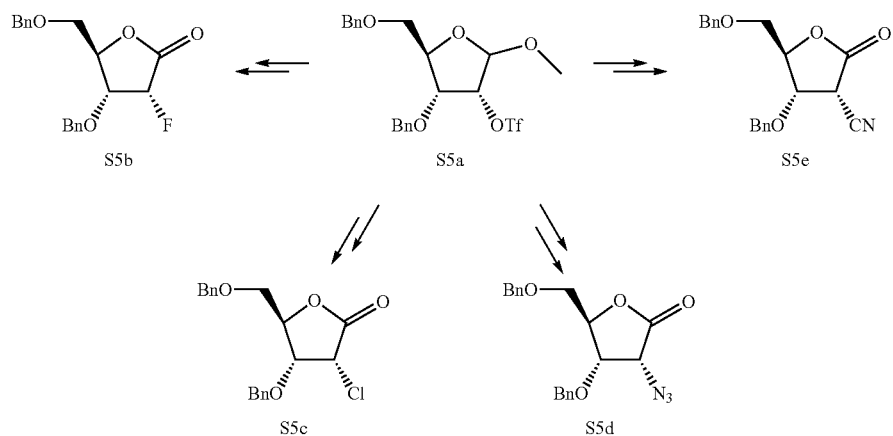
Scheme 5.

Scheme 5 shows a general synthesis of intermediates of the invention through elaboration of the triflate S5a (prepared according to WO2013138236A1, WO2012037038A1, WO2012012776A1). Substitution of the triflate S5a with a fluorine nucleophile (e.g. CsF), hydrolysis of the methoxy acetal (e.g. TFA, H₂O), and oxidation (e.g. PDC) yields the compound of the type S5b suitable for coupling with the nucleobase. Substitution of the triflate S5a with a chlorine nucleophile (e.g. LiCl), hydrolysis of the methoxy acetal (e.g. TFA, H₂O), and oxidation (e.g. PDC) yields the compound of the type S5c suitable for coupling with the nucleobase. Substitution of the triflate S5a with an azide nucleophile (e.g. NaN₃), hydrolysis of the methoxy acetal (e.g. TFA, H₂O), and oxidation (e.g. PDC) yields the compound of the type S5d suitable for coupling with the nucleobase. Substitution of the triflate S5a with a cyanide nucleophile (e.g. NaCN), hydrolysis of the methoxy acetal (e.g. TFA, H₂O), and oxidation (e.g. PDC) yields the compound of the type S5e, suitable for coupling with the nucleobase.

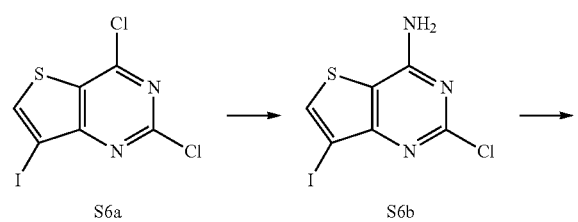
Scheme 6.

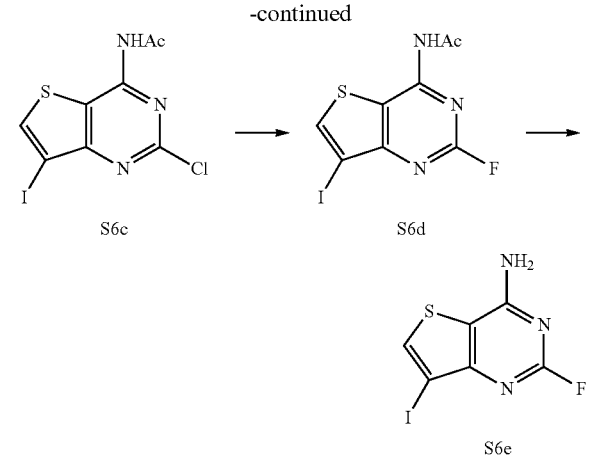

Scheme 6 shows a general synthesis of intermediates of the invention through elaboration of the base S6a (prepared according to WO2008073785A2). Amination (e.g. NH$_3$) of the S6a base yields S6b, which is acylated (e.g. Ac$_2$O) to generate S6c. Addition of a nucleophilic fluorine (e.g. CsF) affords S6d, and removal of the acyl group (e.g. NH$_3$) yield the final compound of the type S6e, suitable for coupling to the lactone.

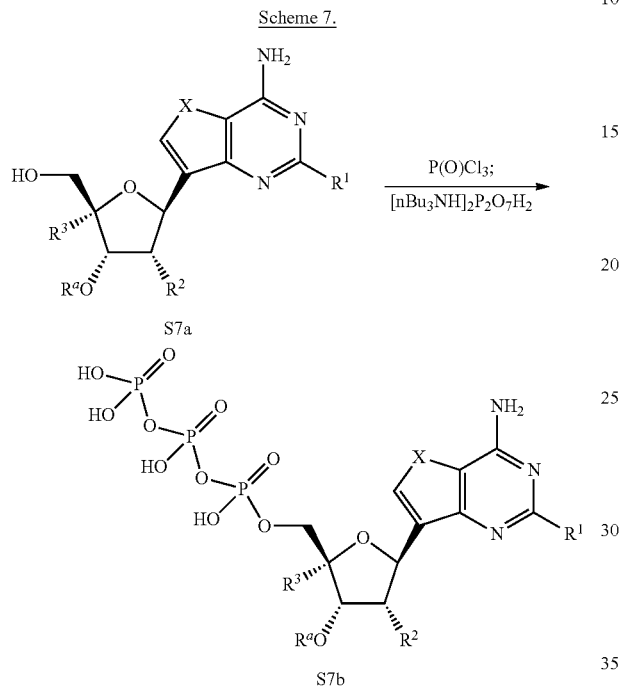

Scheme 7 shows a general synthesis of compounds of the invention involving synthesis of phosphorylated analogs of the type S7b.

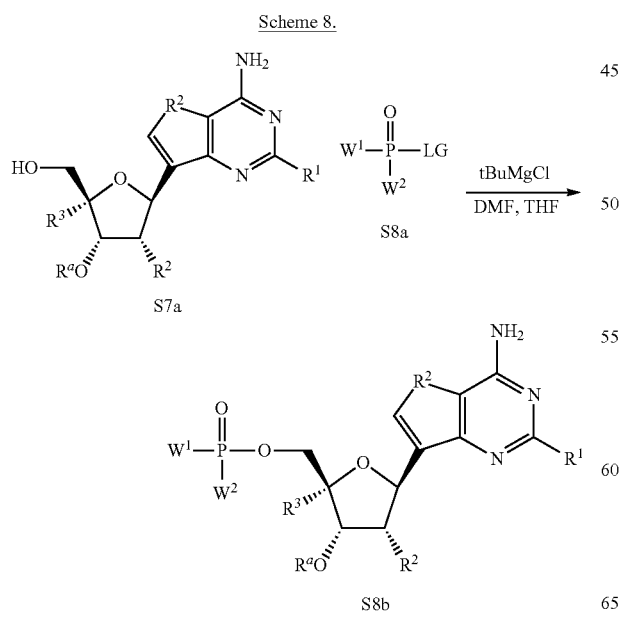

Scheme 8 shows a general synthesis of compounds of the invention involving synthesis of phosphorylated analogs of the type S7b.

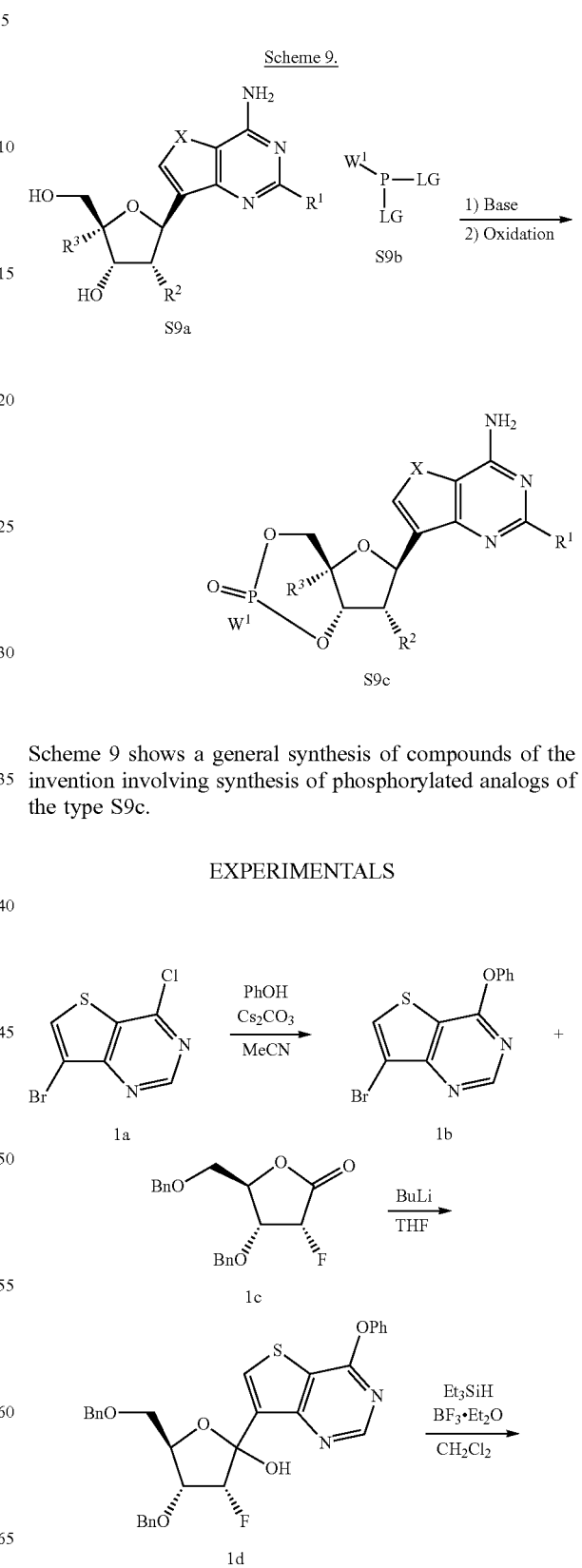

Scheme 9 shows a general synthesis of compounds of the invention involving synthesis of phosphorylated analogs of the type S9c.

EXPERIMENTALS

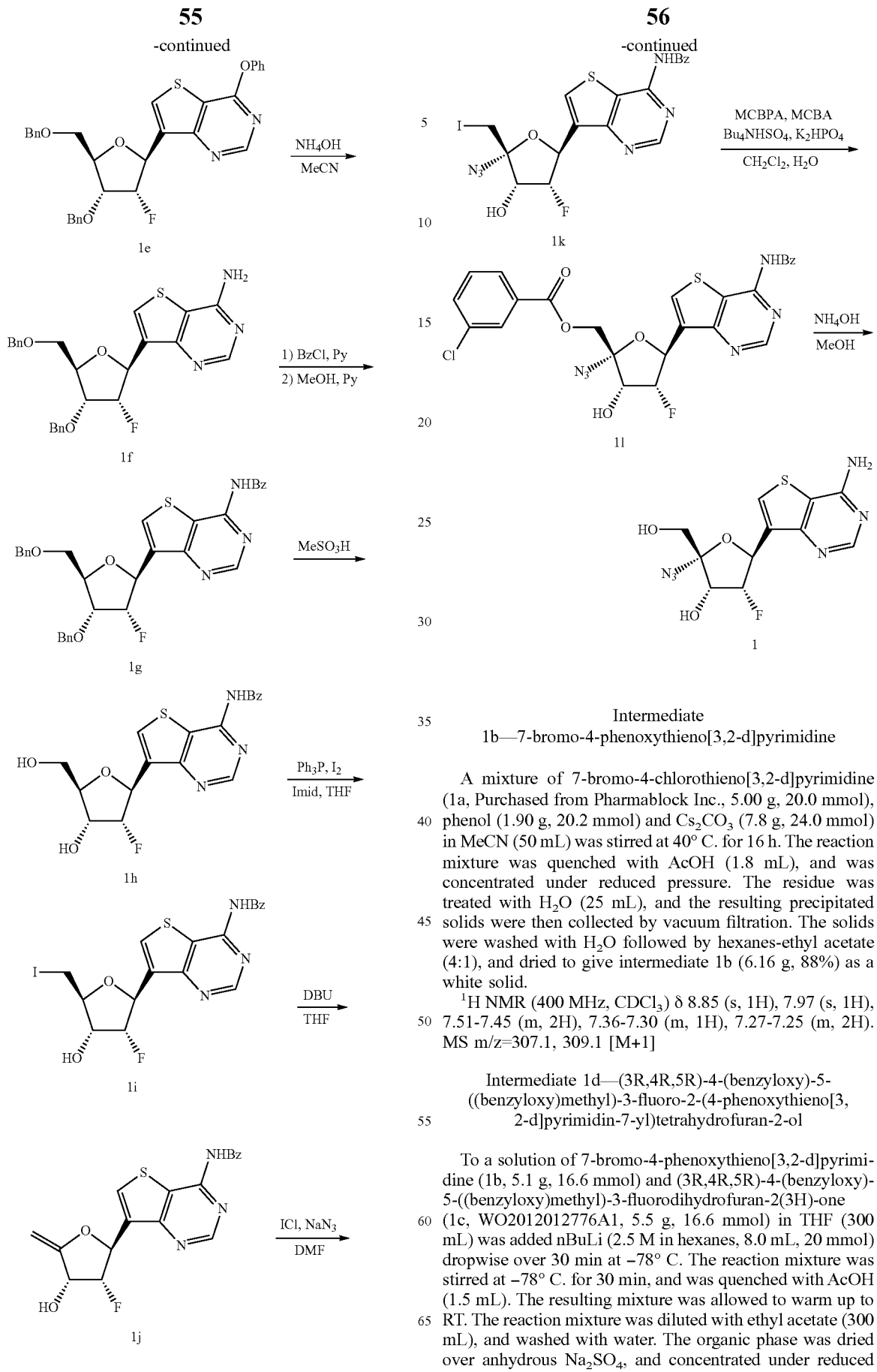

Intermediate 1b—7-bromo-4-phenoxythieno[3,2-d]pyrimidine

A mixture of 7-bromo-4-chlorothieno[3,2-d]pyrimidine (1a, Purchased from Pharmablock Inc., 5.00 g, 20.0 mmol), phenol (1.90 g, 20.2 mmol) and $Cs_2CO_3$ (7.8 g, 24.0 mmol) in MeCN (50 mL) was stirred at 40° C. for 16 h. The reaction mixture was quenched with AcOH (1.8 mL), and was concentrated under reduced pressure. The residue was treated with $H_2O$ (25 mL), and the resulting precipitated solids were then collected by vacuum filtration. The solids were washed with $H_2O$ followed by hexanes-ethyl acetate (4:1), and dried to give intermediate 1b (6.16 g, 88%) as a white solid.

$^1$H NMR (400 MHz, $CDCl_3$) δ 8.85 (s, 1H), 7.97 (s, 1H), 7.51-7.45 (m, 2H), 7.36-7.30 (m, 1H), 7.27-7.25 (m, 2H). MS m/z=307.1, 309.1 [M+1]

Intermediate 1d—(3R,4R,5R)-4-(benzyloxy)-5-((benzyloxy)methyl)-3-fluoro-2-(4-phenoxythieno[3,2-d]pyrimidin-7-yl)tetrahydrofuran-2-ol To a solution of 7-bromo-4-phenoxythieno[3,2-d]pyrimidine (1b, 5.1 g, 16.6 mmol) and (3R,4R,5R)-4-(benzyloxy)-5-((benzyloxy)methyl)-3-fluorodihydrofuran-2(3H)-one (1c, WO2012012776A1, 5.5 g, 16.6 mmol) in THF (300 mL) was added nBuLi (2.5 M in hexanes, 8.0 mL, 20 mmol) dropwise over 30 min at −78° C. The reaction mixture was stirred at −78° C. for 30 min, and was quenched with AcOH (1.5 mL). The resulting mixture was allowed to warm up to RT. The reaction mixture was diluted with ethyl acetate (300 mL), and washed with water. The organic phase was dried over anhydrous $Na_2SO_4$, and concentrated under reduced pressure. The residue was purified by silica gel chromatography, eluting with hexanes-ethyl acetate (6:1 to 3:1), to give an isomer mixture 1d (5.5 g, 59%) as a light yellow oil.
MS m/z=558.9 [M+1].

Intermediate 1e—7-((2S,3S,4R,5R)-4-(benzyloxy)-5-((benzyloxy)methyl)-3-fluorotetrahydrofuran-2-yl)-4-phenoxythieno[3,2-d]pyrimidine To a solution of intermediate 1d (5.5 g, 10 mmol) in CH$_2$Cl$_2$ (50 mL) was added Et$_3$SiH (4.6 g, 39 mmol), then BF$_3$.Et$_2$O (4.2 g, 30 mmol) at RT. The mixture was stirred at RT for 7 days. The reaction mixture was cooled with ice-water bath, and slowly quenched with a solution of NaHCO$_3$ (20 g) in H$_2$O (100 ml). The organic phase was separated, dried over Na$_2$SO$_4$, and purified by silica gel chromatography, eluting with hexane-ethyl acetate (6:1 to 4:1) to give intermediate 1e (3 g, 56%).
$^1$H NMR (400 MHz, CDCl$_3$) δ 8.73 (s, 1H), 8.15 (s, 1H), 7.5-7.45 (m, 2H), 7.4-7.2 (m, 13H), 5.71 (d, J=24.8 Hz, 1H), 5.28 (dd, J=55, 3.6 Hz, 1H), 4.75-4.45 (m, 4H), 4.38-4.25 (m, 2H), 3.98 (dd, J=10.8, 2 Hz, 1H), 3.72 (dd, J=10.8, 2 Hz, 1H). $^{19}$F NMR (376 MHz, CDCl3) δ −195.25 to −195.51 (m). MS m/z=543.1 [M+1].

Intermediate 1f—7-((2S,3S,4R,5R)-4-(benzyloxy)-5-((benzyloxy)methyl)-3-fluorotetrahydrofuran-2-yl)thieno[3,2-d]pyrimidin-4-amine The mixture of intermediate 1e (3 g, 5.53 mmol), NH$_4$OH (28%, 50 mL) and MeCN (50 mL) was stirred in a sealed flask at 65° C. for 64 h. HPLC analysis showed about 40% conversion. Additional NH$_4$OH (28%, 50 mL) and MeCN (50 mL) were then added. The reaction mixture was stirred at 70° C. for another 36 h. HPLC analysis showed about 75% conversion. The reaction mixture was then concentrated, and purified by silica gel chromatography, eluting with ethyl acetate (25-100%)-hexanes to afford intermediate 1f (1.3 g). Residual starting material (intermediate 1e, 0.82 g) was recovered and retreated with NH$_4$OH (28%, 50 mL) in 2Me-THF (25 mL) and EtOH (25 mL) at 70° C. After 64 h, resulting mixture was concentrated under reduced pressure and was purified by silica gel column, eluting with ethyl acetate (25-100%)-hexanes to give an additional 0.75 g of intermediate 1f. In total, 2.05 g (80%) of intermediate 1f was obtained.
$^1$H NMR (400 MHz, CDCl$_3$) δ 8.51 (s, 1H), 7.99 (d, J=1.2 Hz, 1H), 7.38-7.25 (m, 10H), 5.75 (br s, 2H), 5.65 (d, J=24.8 Hz, 1H), 5.25 (dd, J=55, 3.6 Hz, 1H), 4.75-4.45 (m, 4H), 4.38-4.2 (m, 2H), 3.98 (dd, J=10.8, 2 Hz, 1H), 3.72 (dd, J=10.8, 2 Hz, 1H). $^{19}$F NMR (376 MHz, CDCl$_3$) δ −195.12 to −195.39 (m). MS m/z=466.1 [M+1].

Intermediate 1g—N-(7-((2S,3S,4R,5R)-4-(benzyloxy)-5-((benzyloxy)methyl)-3-fluorotetrahydrofuran-2-yl)thieno[3,2-d]pyrimidin-4-yl)benzamide To a solution of intermediate 1f (2.05 g, 4.4 mmol) in pyridine (15 mL) was added benzoyl chloride (1.86 g, 13.2 mmol) at 0° C. The reaction mixture was stirred at RT for 1 h. The reaction mixture was cooled with an ice water bath and was quenched with MeOH (5 mL). The resulted reaction mixture was stirred at 45° C. for 16 h. HPLC and LC-MS showed the 6-NBz$_2$ was converted into 6-NHBz. The reaction mixture was concentrated under reduced pressure. The residue was treated with ethyl acetate and water. The organic phase was separated, dried over Na$_2$SO$_4$, and purified by silica gel chromatography, eluting with ethyl acetate (20-50%)/hexane, to give intermediate 1g (2.1 g, 85%).
$^1$H NMR (400 MHz, CDCl$_3$) δ 8.81 (s, 1H), 8.24 (s, 1H), 8.06 (d, J=7.2 Hz, 2H), 7.66 (t, J=7.2 Hz, 1H), 7.56 (app-t, J=7.6 Hz, 2H), 7.37-7.25 (m, 10H), 5.73 (d, J=24.8 Hz, 1H), 5.22 (dd, J=54.8, 3.6 Hz, 1H), 4.71-4.45 (m, 4H), 4.4-4.20 (m, 2H), 3.98 (dd, J=10.8, 2 Hz, 1H), 3.72 (dd, J=10.8, 3.2 Hz, 1H). $^{19}$F NMR (376 MHz, CDCl$_3$) δ −189.77 to −190.04 (m). MS m/z=570.1 [M+1].

Intermediate 1h—N-(7-((2S,3R,4R,5R)-3-fluoro-4-hydroxy-5-(hydroxymethyl)tetrahydrofuran-2-yl)thieno[3,2-d]pyrimidin-4-yl)benzamide The intermediate 1g (2.1 g, 3.69 mmol) was co-evaporated with toluene (2×6 mL). The residue was dissolved in ethyl acetate (2 mL) and methanesulfonic acid (4 mL) was added at 0° C. After 3 h, additional methanesulfonic acid (1 mL) was added. The reaction mixture was stirred at RT for an additional 4 h at which point the reaction mixture was diluted with ethyl acetate (50 mL). The resulting mixture was cooled to 0° C., and solid NaHCO$_3$ (12.0 g) was added in 4 portions. The resulted mixture was stirred at 0° C. for 1 h, then at RT for 16 h. To the reaction mixture was slowly added water (25 mL). The mixture was stirred for 0.5 h, then filtered to remove the remaining solids. The organic phase was washed with brine, dried over Na$_2$SO$_4$, and concentrated under reduced pressure. The residue was purified by silica gel column, eluting with methanol (0-10%)/dicholomethane, to afford intermediate 1h (0.79 g, 55%).
$^1$H NMR (400 MHz, CD$_3$OD) δ 8.87 (s, 1H), 8.37 (d, J=0.8 Hz, 1H), 8.05 (d, J=7.2 Hz, 2H), 7.66 (t, J=7.6 Hz, 1H), 7.56 (app-t, J=7.6 Hz, 2H), 5.57 (app dd, J=24, 1.6 Hz, 1H), 5.12 (ddd, J=54.8, 4, 1.6 Hz, 1H), 4.31 (ddd, J=19.6, 8, 4 Hz, 1H), 4.07-4.02 (m, 1H), 4.0 (dd, J=12.4, 2.4 Hz, 1H), 3.79 (dd, J=12.4, 4 Hz, 1H). $^{19}$F NMR (376 MHz, CD$_3$OD) δ −202.76 to −203.03 (m). MS m/z=390.1 [M+1].

Intermediate 1i—N-(7-((2S,3R,4R,5S)-3-fluoro-4-hydroxy-5-(iodomethyl)tetrahydrofuran-2-yl)thieno[3,2-d]pyrimidin-4-yl)benzamide To a solution of intermediate 1h (0.79 g, 2.03 mmol), Ph$_3$P (1.20 g, 4.58 mmol) and imidazole (0.277 g, 4.07 mmol) in THF (15 mL) was added iodine (0.96 g, 3.78 mmol) at RT. After 4 h, NaHCO$_3$ (solid, 500 mg) was added to the reaction mixture followed by water (200 µL) to quench the reaction. The reaction mixture was concentrated, and the residue was purified by silica gel column, eluting with ethyl acetate-hexane (1:1), to afford intermediate 1i (0.85 g, 84%) as a solid.
$^1$H NMR (400 MHz, CDCl$_3$) δ 9.05 (br s, 1H), 8.84 (s, 1H), 8.29 (d, J=1.2 Hz, 1H), 8.03 (d, J=7.6 Hz, 2H), 7.68-7.63 (m, 1H), 7.56 (app-t, J=7.6 Hz, 2H), 5.67 (app d, J=27.2 Hz, 1H), 5.27 (ddd, J=55.2, 4.4, 0.8 Hz, 1H), 4.17 (ddd, J=20.8, 8.4, 4.4 Hz, 1H), 3.79-3.75 (m, 1H), 3.72 (dd, J=10.8, 3.6 Hz, 1H), 3.53 (dd, J=10.8, 4.8 Hz, 1H). $^{19}$F NMR 376 MHz, CDCl$_3$) δ −193.33 to −193.61 (m). MS m/z=500.0 [M+1].

Intermediate 1j—N-(7-((2S,3R,4R)-3-fluoro-4-hydroxy-5-methylenetetrahydrofuran-2-yl)thieno[3,2-d]pyrimidin-4-yl)benzamide To a solution of intermediate 1i (0.84 g, 1.68 mmol) in THF (5 mL) was added DBU (0.68 g, 4.47 mmol). The reaction mixture was stirred at RT for 16 h, and was then heated to 45° C. After 8 h, the reaction mixture was allowed to cool to RT, and the reaction mixture was concentrated under reduced pressure. The residue was dissolved in $CH_2Cl_2$ and loaded on to silica gel column, eluting with ethyl acetate (50-100%)-hexane, give intermediate 1j (0.45 g, 72%) as a solid.

$^1$H NMR (400 MHz, DMSO-$d_6$) δ 11.65 (br s, 1H), 8.98 (s, 1H), 8.22 (d, J=1.2 Hz, 1H), 8.08 (d, J=7.6 Hz, 2H), 7.66 (t, J=7.6 Hz, 1H), 7.55 (t, J=7.6 Hz, 2H), 5.82 (d, J=21.6 Hz, 1H), 5.81 (d, J=8 Hz, 1H), 5.24 (dd, J=54.4, 4 Hz, 1H), 4.85-4.72 (m, 1H), 4.43 (br s, 1H), 4.17 (t, J=1.6 Hz, 1H). $^{19}$F NMR (376 MHz, DMSO-$d_6$) δ −201.19 to −201.46 (m). MS m/z=371.9 [M+1].

Intermediate 1k—N-(7-((2S,3R,4R)-5-azido-3-fluoro-4-hydroxy-5-(iodomethyl)tetrahydrofuran-2-yl)thieno[3,2-d]pyrimidin-4-yl)benzamide To suspension of $NaN_3$ (400 mg, 6.15 mmol) in DMF (10 mL) at 0° C. (ice-water bath) was added ICl (400 mg, 2.46 mmol). The resulting mixture was stirred at 0° C. for 10 min, and was allowed to warm to RT over 20 min. The reaction mixture was cooled with an ice-acetone bath, and a solution of the intermediate 1j (400 mg, 1.08 mmol) in DMF (2 mL) was added. The resulting reaction mixture was stirred at 0° C. for 1 h, at which point the reaction was quenched with aqueous $Na_2S_2O_3$ solution (1M, 3 mL). The reaction mixture was concentrated under reduced pressure, and was co-evaporated with $CH_3CN$. The residue was treated with $CH_2Cl_2$ and was filtered. The filtrate was loaded onto a silica gel column, eluting with hexane-ethyl acetate (1:1), to afford intermediate 1k (410 mg, 70%) as a solid. NMR analysis showed it was a 45:55 anomeric mixture at the 4'-position.

$^1$H NMR (400 MHz, DMSO-$d_6$) δ 11.64 (br s, 1H), 8.98 (s, 1H), 8.56 (s, 0.45H), 8.43 (s, 0.55H), 8.08 (d, J=8 Hz, 2H), 7.66 (t, J=8 Hz, 1H), 7.55 (t, J=8 Hz, 2H), 6.47 (d, J=6 Hz, 0.45H), 6.26 (d, J=7.2 Hz, 0.55H), 5.9-5.25 (m, 2H), 4.75-4.45 (m, 1H), 3.74 (s, 1H), 3.62-3.52 (m, 1H). $^{19}$F NMR (376 MHz, DMSO-$d_6$) δ −197.24 to −197.51 (m) (major isomer), −208.52 to −208.73 (m) (minor isomer). MS m/z=540.9 [M+1].

Intermediate 1l—((2R,3R,4R,5S)-2-azido-5-(4-benzamidothieno[3,2-d]pyrimidin-7-yl)-4-fluoro-3-hydroxytetrahydrofuran-2-yl)methyl 3-chlorobenzoate To a solution of intermediate 1k (400 mg, 0.74 mmol), 3-chlorobenzoic acid (300 mg, 1.92 mmol), tetrabutylammonium hydrogensulfate (275 mg, 0.81 mmol) and potassium phosphate dibase (3.$H_2O$, 830 mg, 3.64 mmol) in $CH_2Cl_2$ (50 mL) and $H_2O$ (10 mL) was added 3-chlorobenzoperoxoic acid (77%, 750 mg, 3.35 mmol). The resulted reaction mixture was stirred at room temperature for 4 h. The reaction mixture was cooled with ice-water bath and quenched with aqueous $Na_2S_2O_3$ solution (1M, 5 mL). The resulting mixture was concentrated under reduced pressure, and the residue was taken up into ethyl acetate. The organic phase was washed with saturated aqueous $NaHCO_3$ solution, was dried over anhydrous sodium sulfate, and was concentrated under reduced pressure. The residue was purified by silica gel column, eluting with hexane/ethyl acetate (2:1), to give two isomers: the first eluting desired isomer intermediate 1l (135 mg, 32%, eluted faster than isomer B both on silica gel and C-18 HPLC), and the second eluting undesired isomer (70 mg, 17%, eluted slower than isomer A both on silica gel and C-18 HPLC).

First eluting desired isomer 1l: $^1$H NMR (400 MHz, CDCl$_3$) δ 8.95 (br s, 1H), 8.74 (br s, 1H), 8.08 (s, 1H), 8.02 (d, J=8 Hz, 2H), 7.97 (t, J=1.6 Hz, 1H), 7.91-7.87 (m, 1H), 7.66 (t, J=8 Hz, 1H), 7.59-7.52 (m, 3H), 7.38 (t, J=8 Hz, 1H), 5.80 (d, J=26.8 Hz, 1H), 5.40 (dd, J=54.8, 4.8 Hz, 1H), 4.89 (dd, J=21.6, 5.2 Hz, 1H), 4.80 (d, J=12 Hz, 1H), 4.67 (d, J=12 Hz, 1H). $^{19}$F NMR (400 MHz, CDCl$_3$) δ −192.61 to −192.88 (m). MS m/z=569.0 [M+1].

Second eluting undesired isomer: $^1$H NMR (400 MHz, CDCl$_3$) δ 9.1 (br s, 1H), 8.87 (br s, 1H), 8.16 (s, 1H), 8.08-7.98 (m, 4H), 7.66 (t, J=7.6 Hz, 1H), 7.59-7.55 (m, 3H), 7.41 (t, J=7.6 Hz, 1H), 5.86 (dd, J=18.4, 4.4 Hz, 1H), 5.74 (ddd, J=53.2, 4.8, 4.8 Hz, 1H), 4.83 (d, J=12 Hz, 1H), 4.78 (d, J=12 Hz, 1H), 4.48 (dd, J=10, 4.8 Hz, 1H). $^{19}$F NMR (400 MHz, CDCl$_3$) δ −205.15 to −205.53 (m). MS m/z=568.9 [M+1].

Example 1—(2R,3R,4R,5S)-5-(4-aminothieno[3,2-d]pyrimidin-7-yl)-2-azido-4-fluoro-2-(hydroxymethyl)-tetrahydrofuran-3-ol A solution of intermediate 1l (135 mg, 0.237 mmol) and $NH_4OH$ (28%, 3 mL) in MeOH (3 mL) was stirred at 45° C. for 16 h. The reaction mixture was concentrated under reduced pressure. The residue was purified by prep-HPLC to afford example 1 (54 mg, 70%).

$^1$H NMR (400 MHz, DMSO-$d_6$) δ 8.40 (s, 1H), 8.24 (s, 1H), 7.67 (br s, 2H), 5.85 (br s, 1H), 5.62 (d, J=23.6 Hz, 1H), 5.14 (ddd, J=55.2, 4.8, 2 Hz, 1H), 4.46 (dd, J=24.0, 4.8 Hz, 1H), 3.70 (d, J=12 Hz, 1H), 3.56 (d, J=12 Hz, 1H). $^{19}$F NMR (376 MHz, DMSO-$d_6$) δ −197.67 to −197.94 (m). MS m/z=327.0 [M+1].

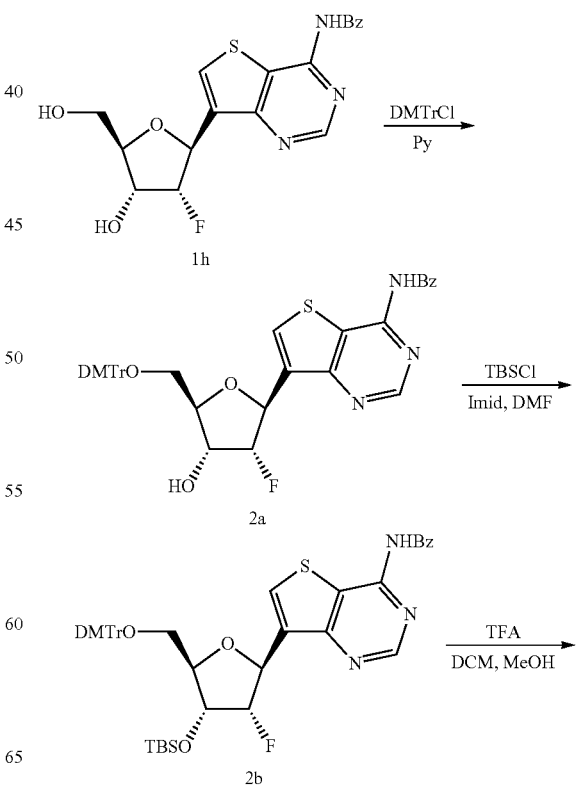

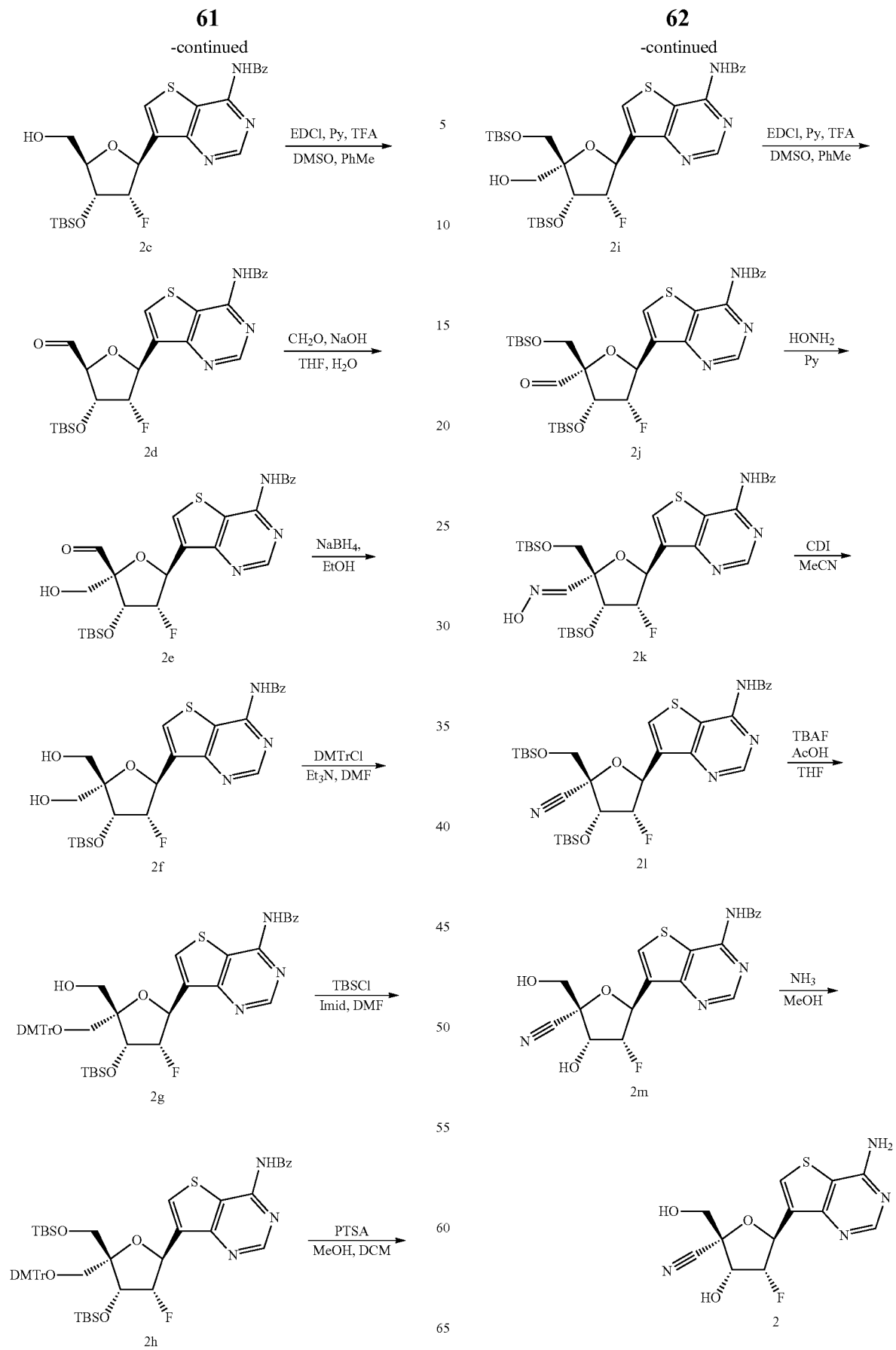

Intermediate 2a—N-(7-((2S,3R,4R,5R)-5-((bis(4-methoxyphenyl)(phenyl)methoxy)methyl)-3-fluoro-4-hydroxytetrahydrofuran-2-yl)thieno[3,2-d]pyrimidin-4-yl)benzamide To a solution of intermediate 1h (2.0 g, 5.14 mmol) in pyridine (20 mL) was added DMTrCl (2.52 g, 7.45 mmol) at RT in one portion. The resulting mixture was stirred at RT for 40 min at which point methanol (5 mL) was added. The mixture was concentrated in vacuo and purified by silica gel column chromatography (0 to 70% ethyl acetate in hexanes) to give intermediate 2a (2.5 g, 70%) as a white foam. MS m/z=692 [M+1]

Intermediate 2b—N-(7-((2S,3S,4R,5R)-5-((bis(4-methoxyphenyl)(phenyl)methoxy)methyl)-4-((tert-butyldimethylsilyl)oxy)-3-fluorotetrahydrofuran-2-yl)thieno[3,2-d]pyrimidin-4-yl)benzamide To a solution of the intermediate 2a (2.5 g, 3.61 mmol) in DMF (20 mL) were added imidazole (738 mg, 10.8 mmol) and TBSCl (817 mg, 5.42 mmol) at RT. The mixture was stirred for 7 h and MeOH (5 mL) was added. After 5 min stirring, the mixture was diluted with EtOAc and was washed with water and with sodium bicarbonate solution. The organic layer was dried with sodium sulfate, and was concentrated in vacuo. The residue was purified by silica gel column chromatography (0 to 70% ethyl acetate in hexanes) to give intermediate 2b (3.0 g, 86%, 84% purity) as a white solid. MS m/z=806 [M+1]

Intermediate 2c—N-(7-((2S,3S,4R,5R)-4-((tert-butyldimethylsilyl)oxy)-3-fluoro-5-(hydroxymethyl)tetrahydrofuran-2-yl)thieno[3,2-d]pyrimidin-4-yl)benzamide To a solution of the intermediate 2b (3.0 g, 3.7 mmol) in DCM (20 mL) and MeOH (10 mL) was added TFA (1.50 mL, 19.6 mmol) dropwise at RT. The mixture was stirred for 1 h at which point it was treated with sodium bicarbonate solution (5 mL) and diluted with dichloromethane. The phases were separated and the organic phase was washed with sodium bicarbonate solution, dried with sodium sulfate, and concentrated under reduced pressure. The residue was purified by silica gel column chromatography (0 to 90% ethyl acetate in hexanes) to afford intermediate 2c (1.6 g, 85%) as a white solid. MS m/z=504 [M+1]

Intermediate 2d—N-(7-((2S,3S,4R,5S)-4-((tert-butyldimethylsilyl)oxy)-3-fluoro-5-formyltetrahydrofuran-2-yl)thieno[3,2-d]pyrimidin-4-yl)benzamide To a solution of intermediate 2c (1.6 g, 3.18 mmol) in DMSO-toluene (10:5 mL) were added 1-ethyl-3-(3-dimethylaminopropyl)carbodiimide HCl (1.83 g, 9.53 mmol), pyridine (0.26 mL, 3.12 mmol), and TFA (0.15 mL, 1.91 mL). The resulting mixture was stirred at RT for 2 h and methanol (5 mL) was added. The resulting mixture was diluted with dichloromethane, washed with water and brine, dried with sodium sulfate, and concentrated in vacuo to afford crude intermediate 2d (1.4 g) which was used directly in the next reaction.

Intermediate 2e—N-(7-((2S,3S,4R,5S)-4-((tert-butyldimethylsilyl)oxy)-3-fluoro-5-formyl-5-(hydroxymethyl)tetrahydrofuran-2-yl)thieno[3,2-d]pyrimidin-4-yl)benzamide Crude intermediate 2d (1.4 g, 2.79 mmol) was dissolved in THF (20 mL) and 37% wt formaldehyde (1.70 mL, 22.8 mmol) and 2N aqueous NaOH solution (2.80 mL, 5.58 mmol) were both added. The resulting mixture was stirred at RT for 2 h. Additional formaldehyde (2 mL) and 2N aqueous NaOH solution (2 mL) were then added. After 30 min, the mixture was neutralized with AcOH, diluted with EtOAc, washed with sodium bicarbonate solution and brine, dried with sodium sulfate, and concentrated in vacuo to give intermediate 2e (1.4 g) as a yellow foam, which was used directly in the next step.

Intermediate 2f—N-(7-((2S,3S,4R)-4-((tert-butyldimethylsilyl)oxy)-3-fluoro-5,5-bis(hydroxymethyl)tetrahydrofuran-2-yl)thieno[3,2-d]pyrimidin-4-yl)benzamide Intermediate 2e (1.4 g, 2.63 mmol) was then dissolved in ethanol (15 mL) and sodium borohydride (110 mg, 2.90 mmol) was added in portion wise over 5 min at 0° C. After stirring 15 min in the ice water bath, the reaction mixture was neutralized with AcOH, diluted with EtOAc, washed with sat. NaHCO$_3$ and brine, and dried over sodium sulfate. The residue was purified by silica gel column chromatography (0 to 100% ethyl acetate in hexanes) to give intermediate 2f (1.0 g, 59% over three steps) as a white solid.

$^1$H NMR (400 MHz, CDCl$_3$) δ 9.40 (s, 1H), 8.84 (s, 1H), 8.13-7.97 (m, 3H), 7.73-7.61 (m, 1H), 7.6-7.47 (m, 2H), 5.55 (dd, J=7.9, 5.5 Hz, 0.5H), 5.49-5.30 (m, 1.5H), 4.76 (dd, J=5.4, 2.6 Hz, 1H), 3.94 (d, J=12.1 Hz, 1H), 3.85 (d, J=12.0 Hz, 1H), 3.70 (d, J=7.6 Hz, 1H), 3.67 (d, J=7.6 Hz, 1H), 0.96 (s, 9H), 0.19-0.14 (m, 6H). $^{19}$F NMR (376 MHz, CDCl$_3$) δ −202.47 (dd, J=53.2, 14.9 Hz). MS m/z=534 [M+1].

Intermediate 2g—N-(7-((2S,3S,4R,5S)-5-((bis(4-methoxyphenyl)(phenyl)methoxy)methyl)-4-((tert-butyldimethylsilyl)oxy)-3-fluoro-5-(hydroxymethyl)tetrahydrofuran-2-yl)thieno[3,2-d]pyrimidin-4-yl)benzamide To a solution of intermediate 2f (1.0 g, 1.94 mmol) and triethylamine (0.7 mL) in dichloromethane (40 mL) was added DMTrCl (984 mg, 2.90 mmol) at 0° C. slowly over 1 h using a syringe pump. Upon completion of addition, the reaction was quenched by adding methanol (2 mL), and the mixture was diluted with dichloromethane, washed with water and saturated aqueous sodium bicarbonate solution, dried with sodium sulfate, and concentrated under reduced pressure. The residue was purified by silica gel column chromatography (0 to 70% ethyl acetate in hexanes) to give provide intermediate 2g (660 mg) and recovered starting material intermediate 2f (340 mg). The recovered starting intermediate 2f (340 mg) was re-subjected to the same reaction conditions and additional intermediate 2g was isolated (total 1.0 g, 64%) as a white solid.

MS m/z=836 [M+1].

Intermediate 2h—N-(7-((2S,3S,4R,5R)-5-((bis(4-methoxyphenyl)(phenyl)methoxy)methyl)-4-((tert-butyldimethylsilyl)oxy)-5-(((tert-butyldimethylsilyl)oxy)methyl)-3-fluorotetrahydrofuran-2-yl)thieno[3,2-d]pyrimidin-4-yl)benzamide Intermediate 2g (1.0 g, 1.20 mmol) was dissolved in DMF (10 mL). Imidazole (244 mg, 3.59 mmol) and TBSCl (270 mg, 1.79 mmol) were added. The resulting mixture was stirred at room temperature for 2 h and methanol (2 mL) was added. The resulting mixture was diluted with EtOAc, washed with water and sodium bicarbonate solution, dried with sodium sulfate, and concentrated in vacuo. The resulting residue was purified by silica gel column chromatography (0 to 70% ethyl acetate in hexanes) to give the fully protected intermediate 2h (1.0 g, 88%) as a white solid.

MS m/z=950 [M+1].

Intermediate 2i—N-(7-((2S,3S,4R,5R)-4-((tert-butyldimethylsilyl)oxy)-5-(((tert-butyldimethylsilyl)oxy)methyl)-3-fluoro-5-(hydroxymethyl)tetrahydrofuran-2-yl)thieno[3,2-d]pyrimidin-4-yl)benzamide Intermediate 2h (1.0 g, 1.05 mmol) was dissolved in dichloromethane (15 mL) and cooled to 0° C. A solution of PTSA (200 mg, 1.05 mmol) in MeOH (5 mL) was slowly added over 5 min and sodium bicarbonate solution (5 mL) was then added stirring vigorously. After diluting with dichloromethane, the mixture was washed with brine, dried with sodium sulfate, and concentrated in vacuo. The resulting residue was purified by silica gel column chromatography (0 to 60% ethyl acetate in hexanes) to give intermediate 2i as a white solid (570 mg, 84%).

MS m/z=648 [M+1].

Intermediate 2j—N-(7-((2S,3S,4R,5R)-4-((tert-butyldimethylsilyl)oxy)-5-(((tert-butyldimethylsilyl)oxy)methyl)-3-fluoro-5-formyltetrahydrofuran-2-yl)thieno[3,2-d]pyrimidin-4-yl)benzamide To a suspension of intermediate 2i (570 mg, 0.88 mmol) and EDCI (506 mg, 2.64 mmol) in toluene-DMSO (2:4 mL) were added pyridine (0.1 mL, 1.24 mmol) and TFA (0.05 mL, 0.65 mmol) in sequence at room temperature. The resulting mixture was stirred at room temperature for 1 h, diluted with ethyl acetate, washed with aqueous sodium bicarbonate solution and brine, dried over sodium sulfate, and concentrated in vacuo to afford intermediate 2j (570 mg), which was used directly in the next step.

MS m/z=646 [M+1].

Intermediate 2k—N-(7-((2S,3S,4R,5R)-4-((tert-butyldimethylsilyl)oxy)-5-(((tert-butyldimethylsilyl)oxy)methyl)-3-fluoro-5-((E)-(hydroxyimino)methyl)tetrahydrofuran-2-yl)thieno[3,2-d]pyrimidin-4-yl)benzamide To a solution of intermediate 2j (570 mg, crude) in pyridine (5 mL) was added hydroxylamine hydrochloride (92 mg, 1.32 mmol) at room temperature. The resulting mixture was stirred at room temperature for 1 h, diluted with ethyl acetate, washed with brine, dried with sodium sulfate, and concentrated in vacuo. The resulting residue was purified by silica gel column chromatography (0 to 80% ethyl acetate in hexanes) to give intermediate 2k (500 mg, 85%) as a white solid.

MS m/z=661 [M+1].

Intermediate 2l—N-(7-((2S,3S,4R,5R)-4-((tert-butyldimethylsilyl)oxy)-5-(((tert-butyldimethylsilyl)oxy)methyl)-5-cyano-3-fluorotetrahydrofuran-2-yl)thieno[3,2-d]pyrimidin-4-yl)benzamide To a solution of intermediate 2k (500 mg, 0.76 mmol) in MeCN-THF (10:5 mL) was added CDI (430 mg, 2.65 mmol) at room temperature. The resulting mixture was stirred at room temperature for 4h, diluted with ethyl acetate, washed with brine, dried with sodium sulfate, and concentrated in vacuo. The resulting residue was purified by silica gel column chromatography (0 to 80% ethyl acetate in hexanes) to give intermediate 2l (480 mg, 99%) as a glassy solid.

$^1$H NMR (400 MHz, CDCl$_3$) δ 9.40 (s, 1H), 8.81 (s, 1H), 8.22 (d, J=1.0 Hz, 1H), 8.09-8.03 (m, 2H), 7.71-7.63 (m, 1H), 7.57 (dd, J=8.5, 7.0 Hz, 2H), 5.80 (dt, J=24.4, 1.4 Hz, 1H), 5.20 (ddd, J=54.4, 4.4, 1.8 Hz, 1H), 4.72 (dd, J=20.4, 4.4 Hz, 1H), 4.16 (d, J=11.3 Hz, 1H), 3.93 (d, J=11.2 Hz, 1H), 0.96 (s, 9H), 0.90 (s, 9H), 0.12 (m, 12H). $^{19}$F NMR (376 MHz, CDCl$_3$) δ −191.15-−191.55 (m). MS m/z=643 [M+1].

Intermediate 2m—N-(7-((2S,3R,4R,5R)-5-cyano-3-fluoro-4-hydroxy-5-(hydroxymethyl)tetrahydrofuran-2-yl)thieno[3,2-d]pyrimidin-4-yl)benzamide To a solution of intermediate 2l (480 mg, 0.75 mmol) in THF (10 mL) were added acetic acid (0.047 mL, 0.82 mL), and then 1M TBAF in THF (0.82 mL, 0.82 mmol) at room temperature. The resulting mixture was stirred at room temperature for 15 h, and concentrated in vacuo. The resulting residue was purified by silica gel column chromatography (0 to 7% MeOH in DCM) to give intermediate 2m (300 mg, 97%) as a syrup.

MS m/z=415 [M+1].

Example 2—(2R,3R,4R,5S)-5-(4-aminothieno[3,2-d]pyrimidin-7-yl)-4-fluoro-3-hydroxy-2-(hydroxymethyl)tetrahydrofuran-2-carbonitrile Intermediate 2m (300 mg, 0.72 mmol) was dissolved in 7M methanolic ammonia (30 mL), and was stirred at room temperature. After 24 h, the reaction mixture was concentrated in vacuo, and the resulting residue was purified by silica gel column chromatography (0 to 50% MeOH in DCM) to afford example 2 (90 mg, 40%) as a white solid. Starting intermediate 2m (120 mg) was also recovered.

$^1$H NMR (400 MHz, CD$_3$OD) δ 8.37 (s, 1H), 8.14 (d, J=0.9 Hz, 1H), 5.67 (ddd, J=23.6, 2.5, 1.0 Hz, 1H), 5.23 (ddd, J=54.4, 4.5, 2.5 Hz, 1H), 4.65 (dd, J=19.8, 4.5 Hz, 1H), 4.04 (d, J=12.2 Hz, 1H), 3.89 (d, J=12.2 Hz, 1H). $^{19}$F NMR (376 MHz, CD$_3$OD) δ −195.68 (ddd, J=54.4, 23.7, 19.8 Hz). MS m/z=311 [M+1].

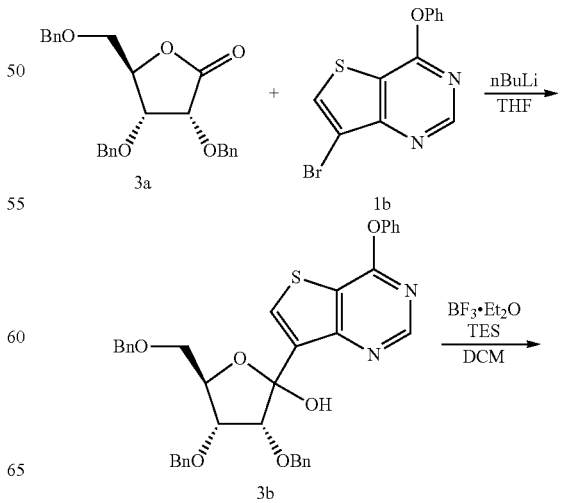

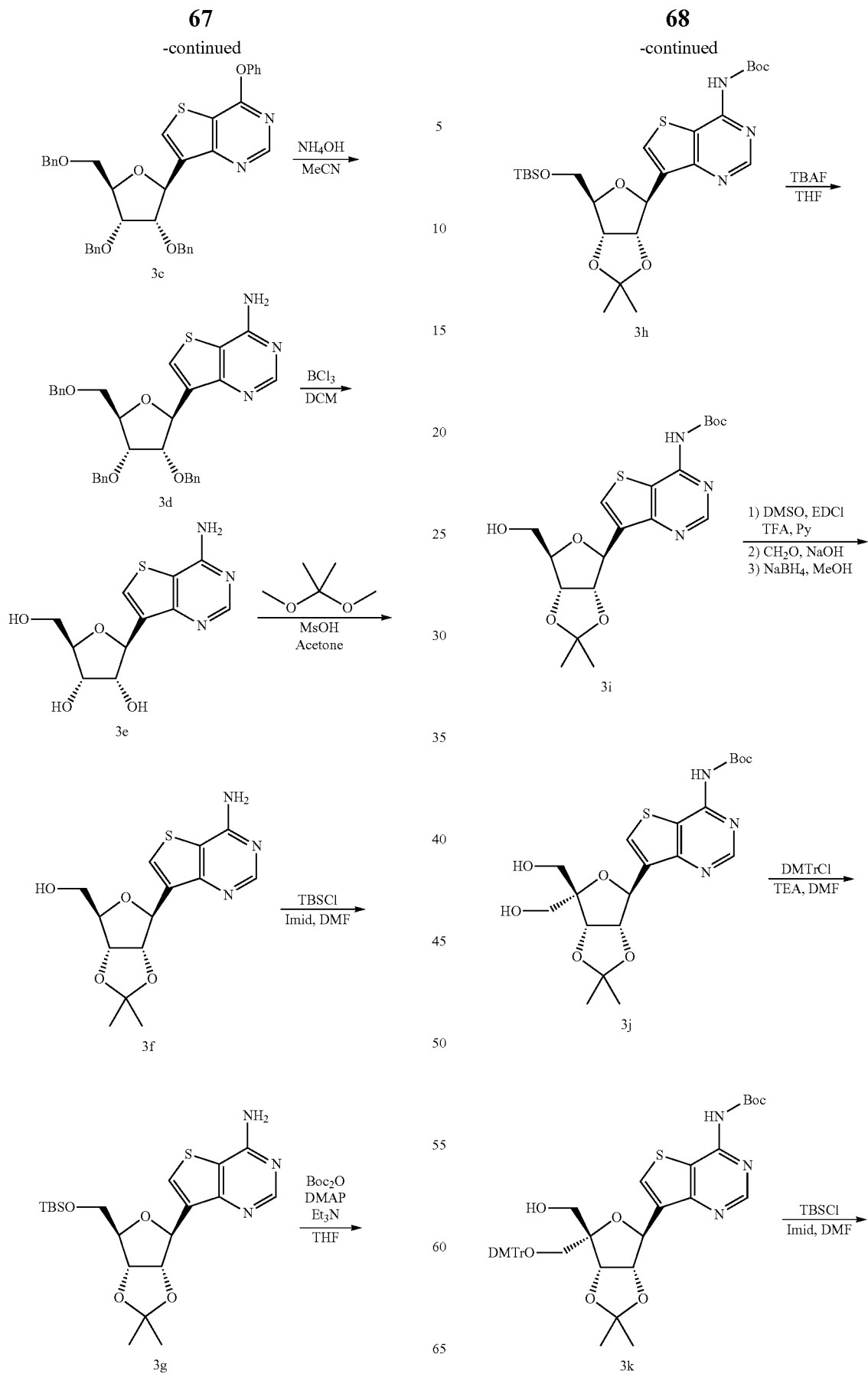

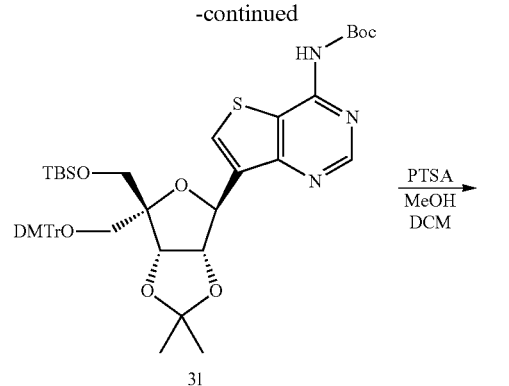

Intermediate 3b—(3R,4R,5R)-3,4-bis(benzyloxy)-5-((benzyloxy)methyl)-2-(4-phenoxythieno[3,2-d]pyrimidin-7-yl)tetrahydrofuran-2-ol To a solution of intermediate 3a (Purchased from Carbosynth, 6.8 g, 16.27 mmol) and intermediate 1b (5 g, 16.3 mmol) in THF (100 mL) was added 2.5M n-butyllithium in hexanes (7.2 mL, 17.9 mmol) dropwise to the reaction mixture while maintaining internal temperature below −60° C. After 2 h, additional 2.5M n-butyllithium in hexanes (1 mL) was added dropwise. After an additional 2 h acetic acid (2 mL, 35.8 mmol) was added dropwise to give pH=3. Removed cold bath and stirred for 10 minutes. Diluted with ethyl acetate (100 mL) and washed with saturated NaHCO$_3$ (aq) (50 mL) and then saturated NaCl(aq) (50 mL). Dried organic over anhydrous Na$_2$SO$_4$ and concentrated under reduced pressure. Purified with silica gel column (0-40% ethyl acetate in hexanes) to give crude intermediate 3b (9g, 85%).

MS m/z=647.0 [M+1].

Intermediate 3c—7-((2S,3S,4R,5R)-3,4-bis(benzyloxy)-5-((benzyloxy)methyl)tetrahydrofuran-2-yl)-4-phenoxythieno[3,2-d]pyrimidine Crude intermediate 3b (9 g, 13.9 mmol) was dissolved in 90 mL anhydrous DCM and the reaction mixture was stirred under Argon at 0° C. in an ice bath. Triethylsilane (5.6 mL, 34.8 mmol) was added dropwise followed by boron trifluoride diethyl etherate (2.6 mL, 20.9 mmol) dropwise. The reaction mixture was stirred at 0° C. for 60 minutes and the reaction mixture was allowed to warm to RT. After 16 h, additional triethylsilane (1.2 mL) and boron trifluoride diethyl etherate (870 uL) were added. After 20 h, the reaction mixture was cooled to 0° C. in an ice bath and TEA (6.8 mL, 48.7 mmol) was added dropwise. The reaction mixture was then concentrated under reduced pressure. The residue was dissolved into ethyl acetate (200 mL) and was washed with saturated NaHCO$_3$(aq) (50 mL) and then saturated NaCl(aq) (50 mL). The organic phase was dried over anhydrous Na$_2$SO$_4$ and concentrated under reduced pressure. The crude residue was purified with silica gel chromatography (0-20-30% ethyl acetate in hexanes) to afford intermediate 3c (2.98 g, 34%).

$^1$H NMR (400 MHz, CDCl$_3$) δ 8.73 (s, 1H), 8.11 (s, 1H), 7.55-7.41 (m, 4H), 7.41-7.19 (m, 16H), 5.70 (s, 1H), 4.95 (s, 2H), 4.67-4.51 (m, 3H), 4.50-4.41 (m, 2H), 4.28 (m, 1H), 4.23 (m, 1H), 3.98 (dd, J=10.8, 2.8 Hz, 1H), 3.73 (dd, J=10.8, 3.2 Hz, 1H). MS m/z=631.2 [M+1].

Intermediate 3d—7-((2S,3S,4R,5R)-3,4-bis(benzyloxy)-5-((benzyloxy)methyl)tetrahydrofuran-2-yl)thieno[3,2-d]pyrimidin-4-amine Intermediate 3c (2.98 g, 4.7 mmol) was dissolved in 25 mL acetonitrile and mixed with 25 mL 30% ammonium hydroxide solution in a sealed vessel and the reaction mixture was heated to 80° C. After 16 h, 30% ammonium hydroxide solution (15 mL) was added and the resulting mixture was stirred at 90° C. for 24 h. Additional acetonitrile (15 mL) was added and the resulting mixture was stirred at 90° C. for 4 days. The reaction mixture was cooled to RT, diluted with EtOAc, and washed with saturated aqueous NaCl solution (3×). The organic layer was dried over anhydrous sodium sulfate and concentrated under reduced pressure. The crude residue was purified with silica gel column (0-50% ethyl acetate in hexanes) to afford intermediate 3d (1.4g, 56%)

$^1$H NMR (400 MHz, CDCl$_3$) δ 7.95 (s, 1H), 7.50-7.16 (m, 16H), 5.62 (s, 1H), 4.93 (s, 2H), 4.66-4.51 (m, 2H), 4.47 (m, 1H), 4.41 (m, 1H), 4.27 (m, 1H), 4.17 (s, 1H), 4.14-4.08 (m, 1H), 3.97 (dd, J=10.8, 2.7 Hz, 1H), 3.71 (dd, J=10.7, 3.0 Hz, 1H). MS m/z=554.2 [M+1].

Intermediate 3e—(2S,3R,4S,5R)-2-(4-aminothieno[3,2-d]pyrimidin-7-yl)-5-(hydroxymethyl)tetrahydrofuran-3,4-diol Intermediate 3d (1.4 g, 2.5 mmol) was dissolved in 3 mL anhydrous DCM and stirred at −78° C. under an argon atmosphere. 1M boron trichloride in DCM (8.8 mL, 8.8 mmol) was added dropwise. The reaction mixture was stirred for 2 h and additional 1M boron trichloride in DCM (1.25 mL) was added. After 1 h, 1M triethylammonium bicarbonate solution (40 mL) was added to the reaction mixture in one portion, and the resulting mixture was diluted with acetonitrile (50 mL). The reaction mixture was allowed to slowly warm to RT, and was concentrated under reduced pressure to give a crude solid. The solids were suspended in ethyl acetate and the resulting mixture was stirred for 30 min. The solvent was decanted and solids were dried under vacuum to afford intermediate 3e (714 mg), which was used directly in the next reaction without further purification.

MS m/z=284.1 [M+1].

Intermediate 3f—((3aR,4R,6S,6aS)-6-(4-aminothieno[3,2-d]pyrimidin-7-yl)-2,2-dimethyltetrahydrofuro[3,4-d][1,3]dioxol-4-yl)methanol Intermediate 3e (714 mg, 2.52 mmol) was dissolved into 50 mL acetone and stirred at RT. 2,2-dimethoxypropane (619 uL, 5.04 mmol) was added followed by the dropwise addition of methanesulfonic acid (245 uL, 3.78 mmol). After 2 h, additional 2,2-dimethoxypropane (620 uL) and methanesulfonic acid (163 uL) were added. After 20 h, additional 2,2-dimethoxypropane (1.2 mL) and methanesulfonic acid (163 uL) were added. After 24 h, additional 2,2-dimethoxypropane (1.2 mL) and methanesulfonic acid (163 uL) were added. After 24 h, additional 2,2-dimethoxypropane (1.2 mL) was added. After 24 h, the reaction mixture was diluted with ethyl acetate (100 mL) and saturated aqueous sodium bicarbonate solution was added to give pH=8. The organic extract was washed with brine, dried over anhydrous sodium sulfate and concentrated under reduced pressure. The resulting gel residue was suspended in hexanes and stirred for 2 h. The solids were collected and were washed with hexanes to afford intermediate 3f (720 mg, 88%).

$^1$H NMR (400 MHz, CD$_3$OD) δ 8.52 (s, 1H), 8.30 (s, 1H), 5.17 (d, J=5.9 Hz, 1H), 4.95-4.91 (m, 1H), 4.80 (t, J=6.1 Hz, 1H), 4.36 (q, J=2.5 Hz, 1H), 3.88 (dd, J=2.6, 1.0 Hz, 2H), 1.62 (s, 3H), 1.37 (s, 3H). MS m/z=324.1 [M+1].

Intermediate 3g—7-((3aS,4S,6R,6aR)-6-(((tert-butyldimethylsilyl)oxy)methyl)-2,2-dimethyltetrahydrofuro[3,4-d][1,3]dioxol-4-yl)thieno[3,2-d]pyrimidin-4-amine Intermediate 3f (720 mg, 2.23 mmol) was dissolved in 10 mL anhydrous DMF. Imidazole (395 mg, 5.8 mmol) and t-butyldimethylsilyl chloride (436 mg, 2.89 mmol) were added. After 3 h, additional imidazole (395 mg) and t-butyldimethylsilyl chloride (436 mg) were added. After 16 h, the reaction mixture was diluted with ethyl acetate (75 mL) and washed with saturated NaHCO$_3$ (aq) and then brine. The organic layer was dried over anhydrous Na$_2$SO$_4$ and concentrated under reduced pressure. The crude residue was purified with silica gel chromatography (0-50% ethyl acetate in hexanes) to afford intermediate 3g (1g, 99%) $^1$H NMR (400 MHz, CDCl$_3$) δ 8.05 (s, 1H), 7.91 (s, 1H), 5.57-5.44 (m, 3H), 4.97 (m, 1H), 4.80 (m, 1H), 4.26 (m, 1H), 3.98-3.74 (m, 2H), 1.67 (s, 3H), 1.41 (s, 3H), 0.92 (s, 9H), 0.10 (s, 6H). MS m/z=438.1 [M+1].

Intermediate 3h—tert-butyl(7-((3aS,4S,6R,6aR)-6-(((tert-butyldimethylsilyl)oxy)methyl)-2,2-dimethyltetrahydrofuro[3,4-d][1,3]dioxol-4-yl)thieno[3,2-d]pyrimidin-4-yl)carbamate Intermediate 3g (976 mg, 2.23 mmol) was dissolved in 12 mL THF. TEA (311 uL, 2.23 mmol) and di-tert-butyl dicarbonate (583 mg, 2.68 mmol) were then added followed by DMAP (136 mg, 1.12 mmol). After 1 h, additional di-tert-butyl dicarbonate (583 mg) and DMAP (136 mg) were added. After an additional 2h, the reaction mixture was diluted with ethyl acetate (75 mL) and washed with 5% aqueous citric acid and then brine. The organic layer was dried over anhydrous Na$_2$SO$_4$ and concentrated under reduced pressure. The crude residue was dissolved in MeOH and 1N NaOH (aq) was added to achieve a pH=12. After 16 h, additional 1N NaOH (aq) to achieve a pH=13. After an additional 14 h, the reaction mixture was diluted with ethyl acetate (75 mL) and washed with brine (3×). The organic layer was dried over anhydrous Na$_2$SO$_4$ and concentrated under reduced pressure. The crude intermediate 3h (1 g, 83%) was used directly in the next reaction without further purification.

MS m/z=538.0 [M+1], 536.3 [M−1].

Intermediate 3i—tert-butyl (7-((3aS,4S,6R,6aR)-6-(hydroxymethyl)-2,2-dimethyltetrahydrofuro[3,4-d][1,3]dioxol-4-yl)thieno[3,2-d]pyrimidin-4-yl)carbamate Intermediate 3h (1 g, 1.86 mmol) was dissolved in 15 mL THF. Tetrabutylammonium fluoride trihydrate (880 mg, 2.79 mmol) was then added in one portion. After 2 h, additional tetrabutylammonium fluoride trihydrate (293 mg, 0.5 eq) was added. After 16 h, the reaction mixture was diluted with ethyl acetate (75 mL) and washed with saturated NaHCO$_3$ (aq) and then brine. The organic layer was dried over anhydrous Na$_2$SO$_4$ and concentrated under reduced pressure. The crude residue was purified with silica gel column (0-50% ethyl acetate in hexanes) to afford intermediate 3i (648 mg, 82%).

$^1$H NMR (400 MHz, CDCl$_3$) δ 8.81 (s, 1H), 8.17 (s, 1H), 8.01 (s, 1H), 5.10 (m, 3H), 4.50 (s, 1H), 3.99 (dt, J=12.3, 1.7 Hz, 1H), 3.83 (dt, J=12.3, 1.8 Hz, 1H), 1.68 (s, 3H), 1.65 (s, 9H), 1.40 (s, 3H). MS m/z=424.0 [M+1], 422.2 [M−1].

Intermediate 3j—tert-butyl (7-((3aS,4S,6aS)-6,6-bis(hydroxymethyl)-2,2-dimethyltetrahydrofuro[3,4-d][1,3]dioxol-4-yl)thieno[3,2-d]pyrimidin-4-yl)carbamate Intermediate 3i (551 mg, 1.3 mmol) was dissolved in 7 mL of anhydrous DMSO under a Nitrogen atmosphere. EDCI (374 mg, 1.95 mmol) was then added in one portion followed by pyridine trifluoroacetate (126 mg, 0.65 mmol). After 1 h, additional EDCI (374 mg, 1.95 mmol) was added. After 1 h, additional EDCI (374 mg, 1.95 mmol) was added. After an additional 1 h, the reaction mixture was diluted with ethyl acetate (75 mL) and was washed with saturated NaHCO$_3$(aq) and then brine. The organic layer was dried organic over anhydrous Na$_2$SO$_4$ and concentrated under reduced pressure. The crude residue was dissolved in 10 mL of dioxane and 1 mL of water. A 37% aqueous formaldehyde solution (774 uL, 10.4 mmol) was added followed by a NaOH (aq) solution (62 mg, 1.56 mmol in 500 uL of water). After 1 h, the reaction mixture was diluted with ethyl acetate (75 mL) and washed with brine (3×). The organic layer was dried over anhydrous Na$_2$SO$_4$ and concentrated under reduced pressure. The crude residue was then dissolved in MeOH (50 mL) and was stirred in an ice bath. Sodium borohydride (98 mg, 2.6 mmol) was then added in one portion. After 30 min, additional sodium borohydride ((98 mg, 2.6 mmol) was added. After an additional 30 min, the reaction mixture was diluted with ethyl acetate (75 mL) and was washed with saturated NaHCO$_3$ (aq) and brine. The organic layer was dried organic over anhydrous Na$_2$SO$_4$ and concentrated under reduced pressure. The crude residue was purified with silica gel chromatography (0-50% ethyl acetate in hexanes) to afford intermediate 3j (360 mg, 61%)

$^1$H NMR (400 MHz, CDCl$_3$) δ 8.80 (s, 1H), 8.07 (s, 1H), 7.99 (d, J=3.0 Hz, 1H), 5.21 (m, 2H), 5.15 (m, 1H), 3.93 (d, J=11.9 Hz, 2H), 3.81 (m, 2H), 1.69 (s, 3H), 1.61 (s, 9H), 1.41 (s, 3H). MS m/z=454.0 [M+1], 452.2 [M−1].

Intermediate 3k—tert-butyl (7-((3aS,4S,6S,6aS)-6-((bis(4-methoxyphenyl)(phenyl)methoxy)methyl)-6-(hydroxymethyl)-2,2-dimethyltetrahydrofuro[3,4-d][1,3]dioxol-4-yl)thieno[3,2-d]pyrimidin-4-yl)carbamate Intermediate 3j (360 mg, 0.79 mmol) was dissolved in 10 mL anhydrous DCM and stirred under a nitrogen atmosphere in an ice bath. TEA (220 uL, 1.58 mmol) was added followed by DMTrCl (401 mg, 1.19 mmol). After 90 min, additional TEA (110 uL) and DMTrCl (134 mg) were added. After 2 h, the reaction mixture was diluted with ethyl acetate (50 mL) and was washed with saturated NaHCO$_3$(aq) and brine. The organic layer was dried over anhydrous Na$_2$SO$_4$ and was concentrated under reduced pressure. The crude residue was purified with silica gel chromatography (0-30% ethyl acetate in hexanes) to afford intermediate 3k (453 mg, 76%).

$^1$H NMR (400 MHz, CDCl$_3$) δ 8.77 (d, J=3.6 Hz, 1H), 7.97 (s, 1H), 7.78 (s, 1H), 7.58-7.49 (m, 1H), 7.41 (m, 2H), 7.37-7.26 (m, 3H), 7.26-7.14 (m, 2H), 6.91-6.77 (m, 4H), 5.25-5.19 (m, 1H), 5.19-5.12 (m, 2H), 4.96-4.85 (m, 1H), 4.07-3.88 (m, 2H), 3.88-3.72 (m, 6H), 3.66-3.56 (m, 1H), 3.19 (d, J=9.4 Hz, 1H), 1.60 (m, 12H), 1.40 (d, J=3.3 Hz, 3H). MS m/z=778.1 [M+Na], 754.2 [M−1].

Intermediate 3l—tert-butyl (7-((3aS,4S,6R,6aS)-6-((bis(4-methoxyphenyl)(phenyl)methoxy)methyl)-6-(((tert-butyldimethylsilyl)oxy)methyl)-2,2-dimethyltetrahydrofuro[3,4-d][1,3]dioxol-4-yl)thieno[3,2-d]pyrimidin-4-yl)carbamate Intermediate 3k (453 mg, 0.6 mmol) was dissolved in 5 mL anhydrous DMF. Imidazole (123 mg, 1.8 mmol) and TBSCl (136 mg, 0.9 mmol) were then added. After 2 h, additional imidazole (123 mg, 1.8 mmol) and TBSCl (136 mg, 0.9 mmol) were added. After 2 h, the reaction mixture was diluted with ethyl acetate (50 mL) and was washed with saturated NaHCO$_3$(aq) and brine. The organic layer was dried over anhydrous Na$_2$SO$_4$ and concentrated under reduced pressure. The crude residue was purified with silica gel chromatography (0-20% ethyl acetate in hexanes) to afford intermediate 3l (519 mg, 99%)

MS m/z=892.1 [M+Na], 868.3 [M−1].

Intermediate 3m—tert-butyl (7-((3aS,4S,6R,6aS)-6-(((tert-butyldimethylsilyl)oxy)methyl)-6-(hydroxymethyl)-2,2-dimethyltetrahydrofuro[3,4-d][1,3]dioxol-4-yl)thieno[3,2-d]pyrimidin-4-yl)carbamate Intermediate 3l (519 mg, 0.60 mmol) was dissolved in 6 mL DCM and stirred in an ice bath at 0° C. under a nitrogen atmosphere. A solution of PTSA (125 mg, 0.66 mmol) in 6 mL MeOH was added to the reaction dropwise. After 1 h, the reaction mixture was diluted with ethyl acetate (50 mL) and was washed with saturated NaHCO$_3$(aq) and brine. The organic layer was dried over anhydrous Na$_2$SO$_4$ and was concentrated under reduced pressure. The crude residue was purified with silica gel chromatography (0-50% ethyl acetate in hexanes) to afford intermediate 3m (254 mg, 75%).

$^1$H NMR (400 MHz, CDCl$_3$) δ 8.86 (dd, J=4.7, 1.6 Hz, 1H), 8.16-8.08 (m, 1H), 8.01 (s, 1H), 5.57 (d, J=4.4 Hz, 1H), 5.07 (dd, J=6.4, 4.1 Hz, 1H), 4.87 (t, J=6.2 Hz, 1H), 4.00-3.78 (m, 4H), 1.71 (d, J=5.4 Hz, 3H), 1.61 (d, J=5.8 Hz, 9H), 1.42 (d, J=5.4 Hz, 3H), 0.98-0.87 (m, 9H), 0.10 (m, 6H). MS m/z=568.0 [M+1], 566.2 [M−1].

Intermediate 3n—tert-butyl (7-((3aS,4S,6R,6aS)-6-(((tert-butyldimethylsilyl)oxy)methyl)-6-cyano-2,2-dimethyltetrahydrofuro[3,4-d][1,3]dioxol-4-yl)thieno[3,2-d]pyrimidin-4-yl)carbamate Intermediate 3m (100 mg, 0.176 mmol) was dissolved in 3 mL anhydrous DMSO and stirred under a nitrogen atmosphere. EDCI (51 mg, 0.26 mmol) was added in one portion followed by pyridine trifluoroacetate (17 mg, 0.088 mmol). After 45 min, additional EDCI (51 mg, 0.26 mmol) was added. After 30 min, additional EDCI (75 mg) was added. After 30 min, additional EDCI (75 mg) was added. After 30 min, the reaction was diluted with ethyl acetate (50 mL) and was washed with saturated NaHCO$_3$(aq) and brine. The organic layer was dried over anhydrous Na$_2$SO$_4$ and concentrated under reduced pressure. The crude residue was dissolved in 5 mL anhydrous pyridine. Hydroxylamine hydrochloride (18 mg, 0.264 mmol) was then added. After 90 min, the reaction mixture was concentrated under reduced pressure. The residue was dissolved in ethyl acetate (50 mL) and the resulting mixture was washed with saturated NaHCO$_3$(aq) and brine. The organic layer was dried over anhydrous Na$_2$SO$_4$ and concentrated under reduced pressure. The crude residue was then dissolved in 5 mL of acetonitrile. CDI (43 mg, 0.264 mmol) was then added and the reaction was stirred for 30 min. Additional CDI (45 mg) was then added and the reaction mixture was stirred for 30 mins. Additional CDI (45 mg) was then added and the reaction mixture was stirred for 30 mins. The reaction mixture was then diluted with ethyl acetate (50 mL) and washed with saturated NaHCO$_3$(aq) brine. The organic layer was then dried over anhydrous Na$_2$SO$_4$ and was concentrated under reduced pressure. The crude residue was purified with silica gel chromatography (0-30% ethyl acetate in hexanes) to afford intermediate 3n (88 mg, 89%).

$^1$H NMR (400 MHz, CDCl$_3$) δ 8.81 (dd, J=4.1, 1.6 Hz, 1H), 8.14-7.93 (m, 1H), 5.68 (dt, J=3.4, 2.1 Hz, 1H), 5.16 (m, 1H), 5.09-4.99 (m, 1H), 4.09-3.96 (m, 2H), 1.87-1.77 (m, 3H), 1.67-1.54 (m, 9H), 1.47-1.36 (m, 3H), 1.01-0.88 (m, 9H), 0.20-0.07 (m, 6H). MS m/z=563.0 [M+1], 561.2 [M−1].

Example 3—(2R,3S,4R,5S)-5-(4-aminothieno[3,2-d]pyrimidin-7-yl)-3,4-dihydroxy-2-(hydroxymethyl)tetrahydrofuran-2-carbonitrile Intermediate 3n (88 mg, 0.156 mmol) was dissolved in 5 mL of a solution of TFA/H$_2$O (1:1). After 20 h, the reaction mixture was concentrated under reduced pressure. The crude residue was dissolved in a 20 mM triethylammonium bicarbonate solution and was purified with prep-HPLC (2-70% acetonitrile in water) to afford example 3 (39 mg, 81%).

$^1$H NMR (400 MHz, CD$_3$OD) δ 8.41 (s, 1H), 8.14 (s, 1H), 5.27 (d, J=7.2 Hz, 1H), 4.47 (dd, J=7.2, 5.4 Hz, 1H), 4.37 (d, J=5.4 Hz, 1H), 4.04-3.85 (m, 2H). MS m/z=309.1 [M+1], 307.1 [M−1].

Example 4—(2R,3R,4R,5S)-5-(4-Aminothieno[3,2-d]pyrimidin-7-yl)-2-azido-4-chloro-2-(hydroxymethyl)tetrahydrofuran-3-ol

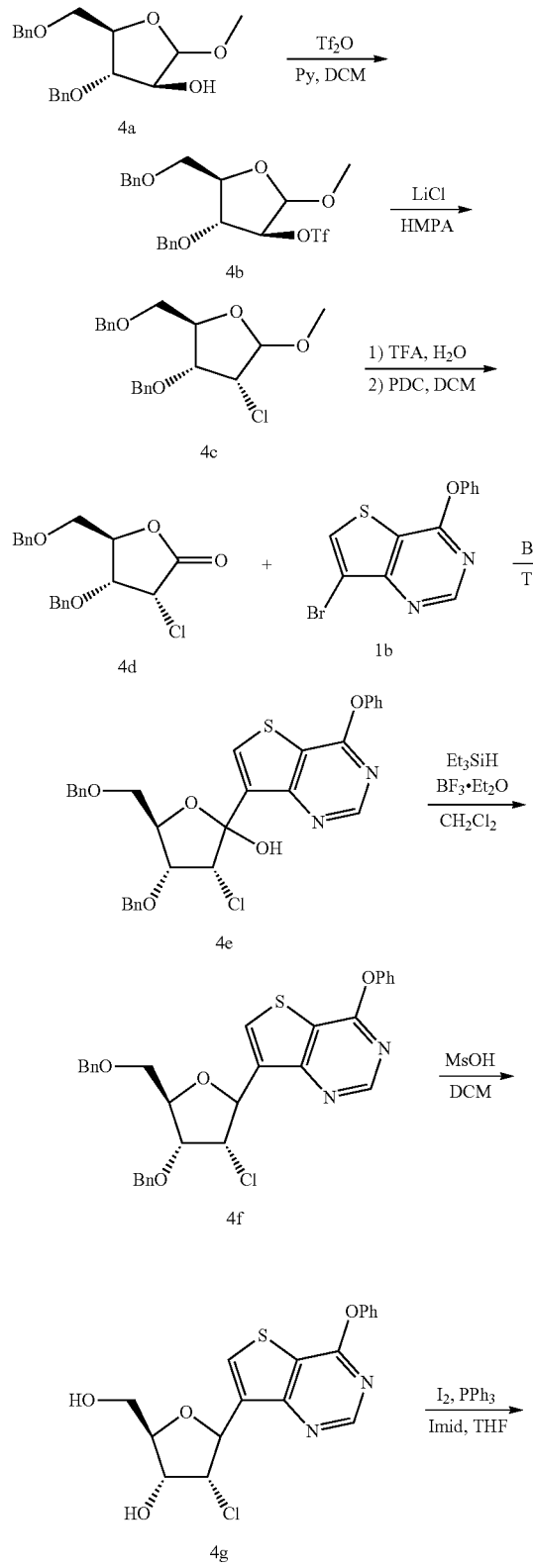

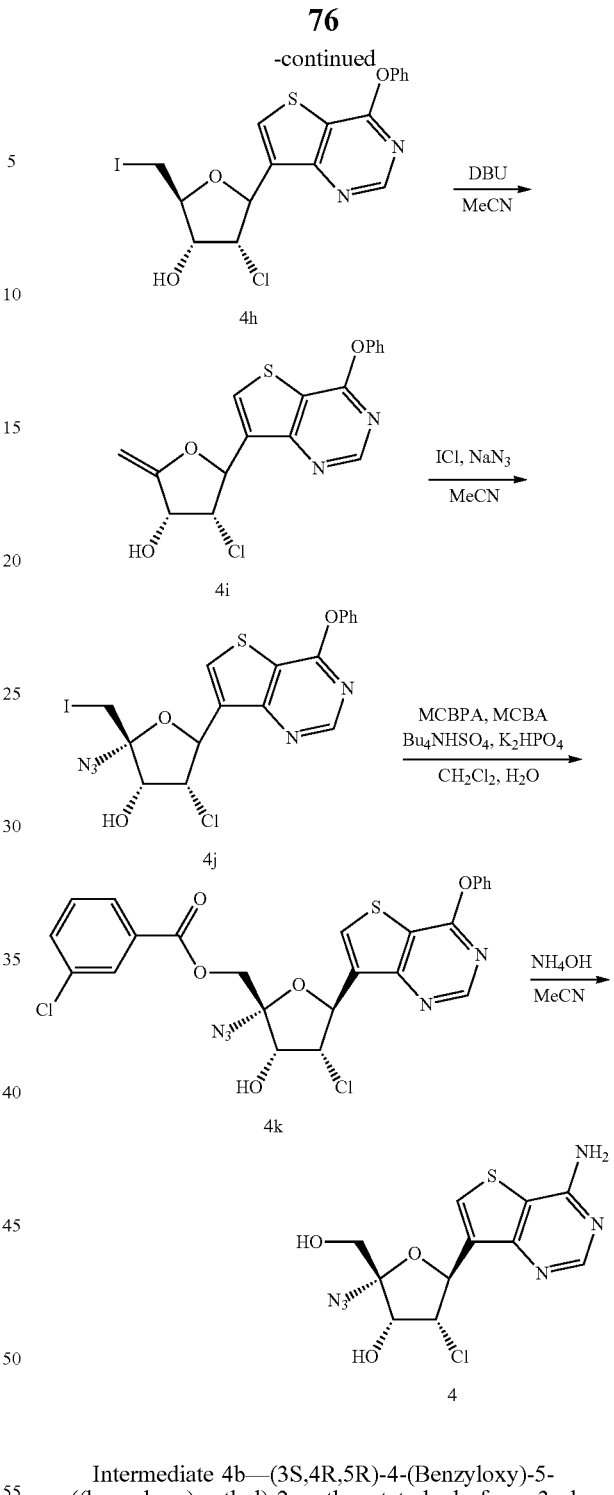

Intermediate 4b—(3S,4R,5R)-4-(Benzyloxy)-5-((benzyloxy)methyl)-2-methoxytetrahydrofuran-3-yl trifluoromethanesulfonate To a solution of intermediate 4a (Purchased from Combi-Blocks, 1.4 g, 0.07 mmol) in methylene chloride (30 mL) and pyridine (15 mL) was added 1M triflic anhydride in DCM (12.2 mL) over 15 min in an ice-bath. The mixture was stirred under ice bath for 30 min, diluted with methylene chloride, washed with aqueous $NaHCO_3$ solution, dried over sodium sulfate, and co-evaporated with toluene. The crude residue purified by silica gel column chromatography (EtOAc 0 to 40% in hexanes) to give compound 4b (1.2 g, 62%) as a syrup.

Intermediate 4c—(2R,3R,4R)-3-(Benzyloxy)-2-((benzyloxy)methyl)-4-chloro-5-methoxytetrahydrofuran A mixture of compound 4b (1.9 g, 4.00 mmol) and LiCl (845 mg, 20.00 mmol) in HMPA (12 mL) was stirred at room temperature for 1 h, diluted with EtOAc, washed with brine (4×), dried with sodium sulfate, concentrated in vacuo, and then the residue purified by silica gel column chromatography (EtOAc 0 to 30% in hexanes) to give compound 4c as an anomeric mixture (800 mg of the faster moving isomer, 300 mg of the slower moving one) as syrup (76%): For slower moving anomer.
$^1$H NMR (400 MHz, CDCl$_3$) δ 7.47-7.07 (m, 10H), 5.02 (d, J=4.3 Hz, 1H), 4.80 (d, J=12.6 Hz, 1H), 4.57 (d, J=12.6 Hz, 1H), 4.50 (d, J=12.1 Hz, 1H), 4.42 (d, J=12.1 Hz, 1H), 4.24 (q, J=3.7 Hz, 1H), 4.18 (dd, J=6.7, 4.3 Hz, 1H), 3.96 (dd, J=6.7, 3.9 Hz, 1H), 3.51 (s, 4H), 3.36 (dd, J=10.7, 3.7 Hz, 1H).

Intermediate 4d—(3R,4R,5R)-4-(Benzyloxy)-5-((benzyloxy)methyl)-3-chlorodihydrofuran-2(3H)-one Compound 4c (3.0 g, 8.27 mmol) was dissolved in TFA (10 mL)-water (10 mL). The resulting mixture was stirred at room temperature for 16 h, heated at 50° C. for 4 h, and concentrated in vacuo. The resulting residue was purified by a silica gel column chromatography (EtOAc 0 to 50% in hexanes) to give a lactol intermediate (2.1 g, 72%) as a syrup. The lactol intermediate (2.1 g, 6.02 mmol) was then dissolved in methylene chloride (40 mL) and treated with 4 A MS (5 g) and pyridinium dichromate (6.80 g, 18.06 mmol). The resultant mixture was stirred at room temperature for 4 h, then filtered through a pad of celite, and concentrated under reduced pressure. The residue was subjected to silica gel chromatography (EtOAc 0 to 30% in hexanes) to give compound 4d (1.7 g, 81%) as a syrup.
$^1$H NMR (400 MHz, CDCl$_3$) δ 7.42-7.23 (m, 10H), 4.76 (d, J=11.7 Hz, 1H), 4.70 (dd, J=5.9, 1.1 Hz, 1H), 4.63-4.51 (m, 3H), 4.48 (d, J=11.9 Hz, 1H), 4.32 (dd, J=5.8, 3.7 Hz, 1H), 3.76 (dd, J=11.3, 2.4 Hz, 1H), 3.62 (dd, J=11.3, 2.6 Hz, 1H).

Intermediate 4e—(3R,4R,5R)-4-(Benzyloxy)-5-((benzyloxy)methyl)-3-chloro-2-(4-phenoxythieno[3,2-d]pyrimidin-7-yl)tetrahydrofuran-2-ol To solution of compound 4d (1.7 g, 4.90 mmol) and compound 1b (2.08 g, 5.88 mmol) in THF (40 mL) at −78° C. was added 1M BuLi (2.35 mL, 5.88 mmol) dropwise for 30 min. The resulting mixture was stirred at −78° C. for 30 min. Then AcOH (2 mL) was added. The reaction mixture was then diluted with EtOAc, washed with brine, and concentrated in vacuo. The residue was purified by silica gel column chromatography (EtOAc 0 to 60% in hexanes) to give compound 4e (2.82 g, 35%).
MS m/z 575 [M+1].

Intermediate 4f—7-((2S,3S,4R,5R)-4-(Benzyloxy)-5-((benzyloxy)methyl)-3-chlorotetrahydrofuran-2-yl)-4-phenoxythieno[3,2-d]pyrimidine Compound 4e (2.0 g, 1.74 mmol) was suspended in DCM (20 mL) and TES (5.56 mL, 34.78 mmol), and then BF3 etherate (1.12 mL, 8.70 mmol) were added under ice bath. The resulting mixture was stirred at room temperature for 6 h and the reaction mixture was neutralized with sodium bicarbonate solution under ice water. Then the mixture was diluted with DCM, washed with water, dried in sodium sulfate, and concentrated in vacuo. The resulting residue was purified by silica gel column chromatography (EtOAc 0 to 50% in hexanes) to give compound 4f (460 mg, 22%) as a white foam.
MS m/z 559 [M+1].

Intermediate 4g—(2R,3R,4R,5S)-4-Chloro-2-(hydroxymethyl)-5-(4-phenoxythieno[3,2-d]pyrimidin-7-yl)tetrahydrofuran-3-ol To solution of compound 4f (460 mg, 0.53 mmol, 64% purity) in DCM (5 mL) was added methanesulfonic acid (0.9 mL, 13.16 mmol) dropwise in ice bath. The resulting mixture was stirred for 15 h at room temperature, neutralized with TEA, concentrated in vacuo, and the residue was purified by silica gel column chromatography (MeOH 0 to 5% in DCM) to give compound 4g (77 mg, 39%) as a gray solid.
$^1$H NMR (400 MHz, DMSO-d6) δ 8.72 (s, 1H), 7.99 (s, 1H), 7.48 (t, J=7.9 Hz, 2H), 7.39-7.30 (m, 1H), 7.25 (dd, J=8.7, 1.3 Hz, 2H), 5.23 (d, J=10.0 Hz, 1H), 4.97 (dd, J=10.0, 4.4 Hz, 1H), 4.52 (d, J=4.4 Hz, 1H), 4.38 (s, 1H), 3.99 (dd, J=12.7, 1.9 Hz, 1H), 3.79 (dd, J=12.7, 1.4 Hz, 1H).
MS m/z 379 [M+1].

Intermediate 4h—(2S,3R,4R,5S)-4-Chloro-2-(iodomethyl)-5-(4-phenoxythieno[3,2-d]pyrimidin-7-yl)tetrahydrofuran-3-ol To the mixture of compound 4g (100 mg, 0.264 mmol), Ph$_3$P (104 mg, 0.396 mmol), and imidazole (27 mg, 0.396 mmol) in THF (4 mL) was added iodine (101 mg, 0.396 mmol) at room temperature. The reaction mixture was stirred at room temperature for 5 h and aq NaHCO3 solution (2 mL) was added. The mixture was then concentrated in vacuo and purified by silica gel column chromatography (EtOAc 0 to 60% in hexanes) to give compound 4h (97 mg, 75%) as a white solid.
MS m/z 489 [M+1].

Intermediate 4j—(2S,3R,4R,5S)-2-Azido-4-chloro-2-(iodomethyl)-5-(4-phenoxythieno[3,2-d]pyrimidin-7-yl)tetrahydrofuran-3-ol Compound 4h (90 mg, 0.184 mmol) and DBU (0.165 mL, 1.11 mmol) was stirred at room temperature for 15 h. The reaction mixture was then diluted with EtOAc, washed with water, dried under sodium sulfate, and concentrated in vacuo to afford the crude residue 4i, which was dried under high vacuum and used directly in next reaction.
To suspension of sodium azide (127 mg, 1.954 mmol) in MeCN at 0° C. was added ICl (0.021 mL, 0.421 mmol). The resulting mixture was stirred for 30 min at room temperature and crude residue of 4i (66 mg, 0.184 mmol) in acetonitrile (1 mL) was added dropwise at 0° C. The resulting mixture was stirred for 30 min at 0° C. and sodium thiosulfate (0.2 mL) was added. The mixture was then stirred for 10 min, diluted with EtOAc, washed with brine, dried with sodium sulfate, and concentrated in vacuo. The resulting residue was purified by silica gel column chromatography (EtOAc 0 to 50% in hexanes) to give compound 4j (30 mg, 31%, as 1.3:1 isomeric mixture) as a white solid.
MS m/z 530 [M+1].

Intermediate 4k—((2R,3R,4R,5S)-2-Azido-4-chloro-3-hydroxy-5-(4-phenoxythieno[3,2-d]pyrimidin-7-yl)tetrahydrofuran-2-yl)methyl 3-chlorobenzoate A mixture of compound 4j (30 mg, 0.057 mmol), mCBA (22 mg, 0.142 mmol), tetrabutylammonium hydrogen sulfate (20 mg, 0.057 mmol), and potassium phosphate dibasic (52 mg, 0.227 mmol) was cooled in ice bath and then mCPBA (51 mg, 0.227 mmol) was added vigorously stirring. The resulting mixture was stirred for 3 h in and ice water and 1 h at room temperature. Then sodium thiosulfate solution (0.5 mL) added under ice bath. After 5 min, the mixture was diluted with EtOAc, washed with brine, dried with sodium sulfate, and concentrated in vacuo. The resulting residue was purified by silica gel column chromatography (EtOAc 0 to 30% in hexanes) to give compound 4k (7 mg, 22%) as a white solid.

$^1$H NMR (400 MHz, CDCl$_3$) δ 8.65 (s, 1H), 8.04 (d, J=0.8 Hz, 1H), 7.97 (t, J=1.8 Hz, 1H), 7.90 (dt, J=7.9, 1.3 Hz, 1H), 7.54 (ddd, J=8.0, 2.1, 1.1 Hz, 1H), 7.52-7.44 (m, 2H), 7.41-7.30 (m, 2H), 7.28-7.20 (m, 2H), 5.80 (d, J=3.4 Hz, 1H), 5.16 (dd, J=6.7, 3.4 Hz, 1H), 5.00 (dd, J=11.1, 6.8 Hz, 1H), 4.77 (d, J=11.9 Hz, 1H), 4.67 (d, J=11.9 Hz, 1H). MS m/z 558 [M+1].

Example 4—(2R,3R,4R,5S)-5-(4-Aminothieno[3,2-d]pyrimidin-7-yl)-2-azido-4-chloro-2-(hydroxymethyl)tetrahydrofuran-3-ol A mixture of compound 4k (7 mg, 0.013 mmol), concentrated aqueous ammonium hydroxide (0.5 mL), and acetonitrile (0.5 mL) was heated at 70° C. in a sealed flask for 48 h. The resulting mixture was then concentrated in vacuo, dissolved in methanol (1 mL), and purified with HPLC (acetonitrile 0 to 30% in water in 20 min) to give compound 4 (2.7 mg, 63%) as an off-white solid.

$^1$H NMR (400 MHz, Methanol-d4) δ 8.38 (s, 1H), 8.21 (s, 1H), 5.49 (d, J=9.4 Hz, 1H), 4.95 (dd, J=9.4, 4.8 Hz, 1H), 4.45 (d, J=4.8 Hz, 1H), 3.73 (d, J=12.1 Hz, 1H), 3.54 (d, J=12.1 Hz, 1H). MS m/z=343 (M+1).

Triphosphate (TP) Examples

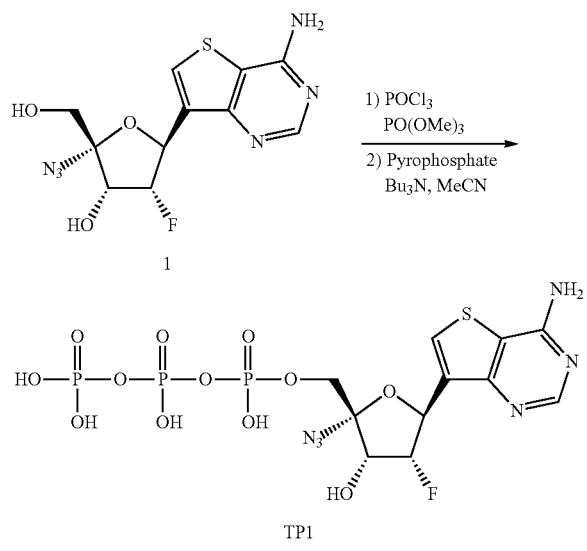

TP1

Example TP1—((2R,3R,4R,5S)-5-(4-aminothieno[3,2-d]pyrimidin-7-yl)-2-azido-4-fluoro-3-hydroxytetrahydrofuran-2-yl)methyl tetrahydrogen triphosphate To a solution of example 1 (15 mg, 0.046 mmol) and NaHCO$_3$ (10 mg, 0.119 mmol) in trimethyl phosphate (0.6 mL) at 0° C. was added POCl$_3$ (50 mg, 0.326 mmol). The reaction mixture was stirred at 0° C. for 6 h. Ion-exchange HPLC showed about 65% conversion. A solution of pyrophosphate tributylamine salts (250 mg, 0.688 mmol) in MeCN (0.6 mL) was added, followed by tributylamine (121 mg, 0.65 mmol). The reaction mixture was stirred at 0° C. for 0.5 h. The reaction was quenched with aqueous triethylammonium bicarbonate buffer solution (1M, 6 mL). The reaction mixture was stirred at RT for 0.5 h, then concentrated and co-evaporated with water twice. The residue was dissolved in H$_2$O (5 mL) and loaded to a ion-exchange column, eluted with H$_2$O, then 10-35% triethylammonium bicarbonate buffer (1M)-H$_2$O. The product fractions were combined, concentrated and co-evaporated with H$_2$O to give about 20 mg of material. The material was dissolved in H$_2$O (1 mL), and treated with aqueous NaOH solution (1N, 0.12 mL), concentrated to about 0.5 mL, and purified with C-18 column, eluting with H$_2$O. The product fractions were combined and concentrated to give the desired triphosphate TP1 as the tetrasodium salt (14 mg, 47%).

$^1$H NMR (400 MHz, D$_2$O) δ 8.19 (s, 1H), 8.06 (s, 1H), 5.73 (d, J=24 Hz, 1H), 5.06 (dd, J=55.6, 4.4 Hz, 1H), 4.63 (dd, J=28.0, 4.4 Hz, 1H), 4.19 (br s, 2H). $^{19}$F NMR (376 MHz, D$_2$O) δ −195.32 to −195.60 (m). $^{31}$P NMR (162 MHz, D$_2$O) δ −8.16 (d, J=48 Hz, 1P), −14.10 (d, J=48 Hz, 1P), −23.9 (t, J=48 Hz, 1P). MS m/z=566.97 [M+1].

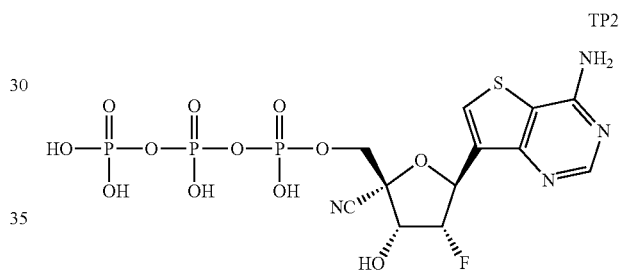

TP2

Example TP2—((2R,3R,4R,5S)-5-(4-aminothieno[3,2-d]pyrimidin-7-yl)-2-cyano-4-fluoro-3-hydroxytetrahydrofuran-2-yl)methyl tetrahydrogen triphosphate Example TP2 (6 mg, 53%) was prepared as the tetrasodium salt in a similar manner as example TP1 using example 2 as a starting material.

$^1$H NMR (400 MHz, D$_2$O) δ 8.26 (s, 1H), 8.07 (s, 1H), 5.77 (d, J=24.8 Hz, 1H), 5.16 (dd, J=54, 4 Hz, 1H), 4.75 (dd, J=26.0, 4.0 Hz, 1H), 4.4 (d, J=4.8 Hz, 2H). $^{19}$F NMR (376 MHz, D$_2$O) δ −193.49 to −193.77 (m). $^{31}$P NMR (162 MHz, D$_2$O) δ −8.22 (d, J=48 Hz, 1P), −14.45 (d, J=48 Hz, 1P), −24.0 (t, J=48 Hz, 1P). MS m/z=550.89 [M+1].

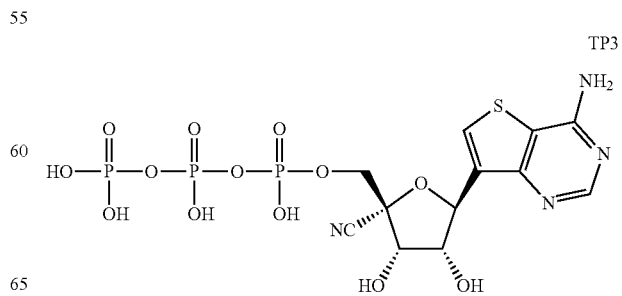

TP3

Example TP3—((2R,3S,4R,5S)-5-(4-aminothieno[3, 2-d]pyrimidin-7-yl)-2-cyano-3,4-dihydroxytetrahydrofuran-2-yl)methyl tetrahydrogen triphosphate Example TP3 (3 mg, 26%) was prepared as the tetrasodium salt in a similar manner as example TP1 using example 3 as a starting material.

$^1$H NMR (400 MHz, D$_2$O) δ 8.22 (s, 1H), 8.08 (s, 1H), 5.4 (d, J=4.4 Hz, 1H), 4.55 (d, J=4.4 Hz, 1H), 4.37 (dd, J=4.4, 4.4 Hz, 1H), 4.18-4.3 (m, 2H). $^{31}$P NMR (162 MHz, D$_2$O) δ −4.27 (d, J=48 Hz, 1P), −10.44 (d, J=48 Hz, 1P), −20.1 (t, J=48 Hz, 1P). MS m/z=548.95 [M+1].

Example TP4—((2R,3R,4R,5S)-5-(4-aminothieno[3, 2-d]pyrimidin-7-yl)-2-azido-4-chloro-3-hydroxytetrahydrofuran-2-yl)methyl tetrahydrogen triphosphate

TP4

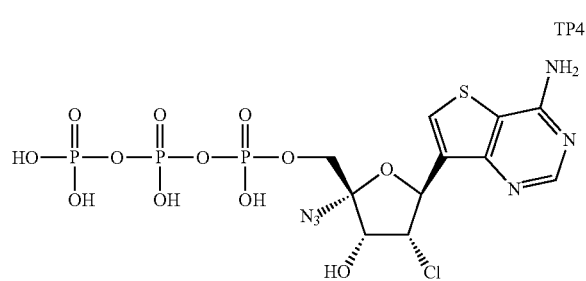 [SMILES: [N-]=[N+]=N[C@]1(COP(=O)(O)OP(=O)(O)OP(=O)(O)O)O[C@@H](c2csc3c(N)ncnc23)[C@H](Cl)[C@@H]1O]

Example TP4 was prepared as the tetrasodium salt in a similar manner as example TP1 using example 4 as a starting material.

$^1$H NMR (400 MHz, D$_2$O) δ 8.28 (s, 1H), 8.24 (s, 1H), 5.76 (d, J=4.4 Hz, 1H), 4.77 (d, J=4.4 Hz, 1H), 4.70 (dd, J=4.8, 4.8 Hz, 1H), 4.20-4.10 (m, 2H). $^{31}$P NMR (162 MHz, D$_2$O) δ −4.85 (d, J=48.4 Hz, 1P), −10.32 (d, J=48.4 Hz, 1P), −20.44 (t, J=48.4 Hz, 1P). MS m/z=582.88 [M+1].

Example PD1 (2S)-ethyl 2-(((((2R,3R,4R,5S)-5-(4-aminothieno[3,2-d]pyrimidin-7-yl)-2-azido-4-fluoro-3-hydroxytetrahydrofuran-2-yl)methoxy)(phenoxy)phosphoryl)amino)propanoate Example 1 (5.00 mg, 15.3 μmol) was dissolved in NMP (0.2 mL). THF (0.1 mL) was added followed by tert-butyl magnesium chloride (1.0M solution in THF, 0.024 mL, 23 μmol) at RT under an argon atmosphere. After 20 min, a solution of intermediate PD1a (prepared according to US20120009147A1, 12.1 mg, 30.7 μmol) in THF (0.1 mL) was added and the reaction mixture was warmed to 50° C. After 23 h, additional intermediate PD1a (12.1 mg, 30.7 μmol) and tert-butyl magnesium chloride (1.0M solution in THF, 0.024 mL, 23 μmol) were added. After 5 h, the resulting mixture was purified directly by preparatory HPLC (Phenominex Synergi 4u Hydro-RR 80 Å 150×30 mm column, 40-100% acetonitrile/water gradient). The major diastereomer was isolated to afford example PD1 (1.0 mg, 20%), as light yellow solid.

$^1$H NMR (400 MHz, CDCl$_3$) δ 8.57 (s, 1H), 7.94 (s, 1H), 7.38-7.12 (m, 5H), 5.81 (d, J=25.1 Hz, 1H), 5.76 (br s, 1H), 5.25 (dd, J=54.9, 4.8 Hz, 1H), 4.59 (br d, J=24.4 Hz, 1H), 4.45 (dd, J=11.2, 7.2 Hz, 1H), 4.34 (dd, J=11.2, 7.1 Hz, 1H), 4.21-4.08 (m, 2H), 4.02 (td, J=8.9, 6.8 Hz, 1H), 3.83-3.72 (m, 1H), 1.36 (d, J=7.1 Hz, 3H), 1.23 (t, J=7.1 Hz, 3H). $^{19}$F NMR (376 MHz, D$_2$O) δ −193.64 (dt, J=54.4, 24.4 Hz). $^{31}$P NMR (162 MHz, CDCl$_3$) δ 2.57 (s). MS m/z=581.90 [M+1].

Also provided are the following compounds, or a pharmaceutically acceptable salt thereof, which may be prepared using methods disclosed herein:

a) (2R,3R,4R,5S)-5-(4-amino-2-fluorothieno[3,2-d]pyrimidin-7-yl)-2-azido-4-fluoro-2-(hydroxymethyl)tetrahydrofuran-3-ol:

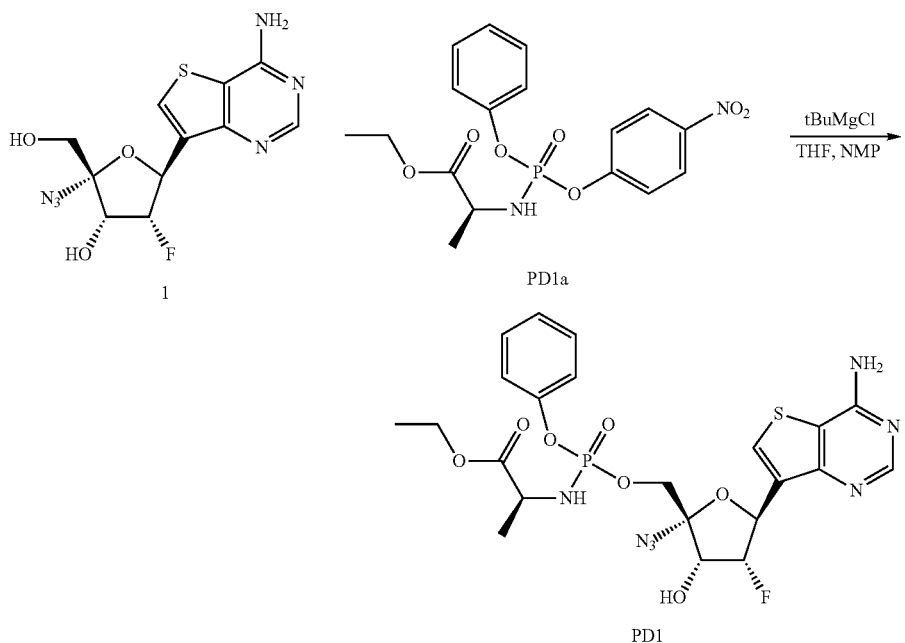

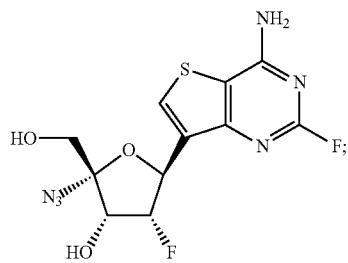 [SMILES: [N-]=[N+]=N[C@]1(CO)O[C@@H](c2csc3c(N)nc(F)nc23)[C@H](F)[C@@H]1O]

b) (2R,3R,4R,5S)-5-(4-aminothieno[3,2-d]pyrimidin-7-yl)-2-azido-4-chloro-2-(hydroxymethyl)tetrahydrofuran-3-ol:

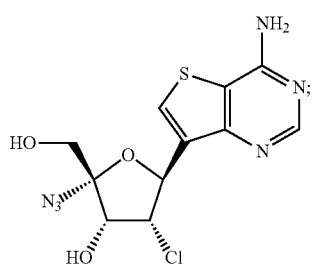 [SMILES: [N-]=[N+]=N[C@]1(CO)O[C@@H](c2csc3c(N)ncnc23)[C@H](Cl)[C@@H]1O]

and c) (2R,3S,4R,5S)-5-(4-aminothieno[3,2-d]pyrimidin-7-yl)-2,4-diazido-2-(hydroxymethyl)tetrahydrofuran-3-ol:

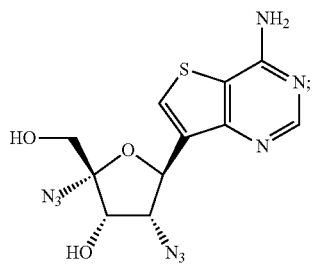 [SMILES: [N-]=[N+]=N[C@H]1[C@H](c2csc3c(N)ncnc23)O[C@@](CO)(N=[N+]=[N-])[C@H]1O]

d) (2R,3S,4R,5S)-5-(4-aminothieno[3,2-d]pyrimidin-7-yl)-4-azido-3-hydroxy-2-(hydroxymethyl)tetrahydrofuran-2-carbonitrile:

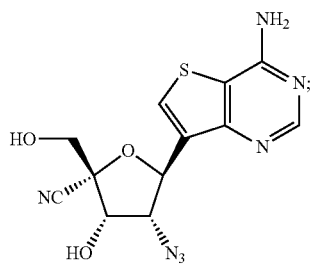 [SMILES: N#C[C@]1(CO)O[C@@H](c2csc3c(N)ncnc23)[C@H](N=[N+]=[N-])[C@@H]1O]

e) (2R,3R,4R,5S)-5-(4-aminothieno[3,2-d]pyrimidin-7-yl)-2-ethyl-4-fluoro-2-(hydroxymethyl)tetrahydrofuran-3-ol:

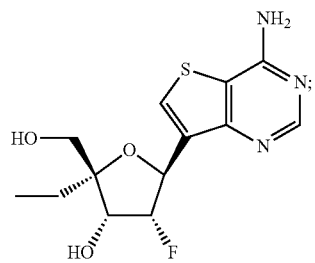 [SMILES: CC[C@]1(CO)O[C@@H](c2csc3c(N)ncnc23)[C@H](F)[C@@H]1O]

f) (2R,3R,4R,5S)-5-(4-aminothieno[3,2-d]pyrimidin-7-yl)-4-chloro-2-ethyl-2-(hydroxymethyl)tetrahydrofuran-3-ol:

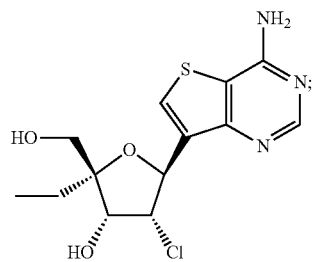 [SMILES: CC[C@]1(CO)O[C@@H](c2csc3c(N)ncnc23)[C@H](Cl)[C@@H]1O]

g) (2R,3S,4R,5S)-5-(4-aminothieno[3,2-d]pyrimidin-7-yl)-4-azido-2-ethyl-2-(hydroxymethyl)tetrahydrofuran-3-ol:

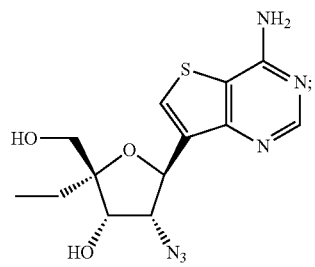 [SMILES: CC[C@]1(CO)O[C@@H](c2csc3c(N)ncnc23)[C@H](N=[N+]=[N-])[C@@H]1O]

h) (2R,3R,4R,5S)-5-(4-aminothieno[3,2-d]pyrimidin-7-yl)-2-(chloromethyl)-4-fluoro-2-(hydroxymethyl)tetrahydrofuran-3-ol:

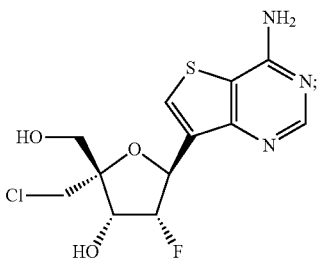 [SMILES: Nc1ncnc2c([C@@H]3O[C@@](CO)(CCl)[C@@H](O)[C@H]3F)csc12]

i) (2R,3R,4R,5S)-5-(4-aminothieno[3,2-d]pyrimidin-7-yl)-4-chloro-2-(chloromethyl)-2-(hydroxymethyl)tetrahydrofuran-3-ol:

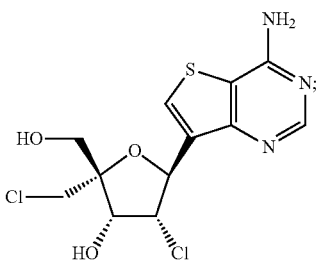 [SMILES: Nc1ncnc2c([C@@H]3O[C@@](CO)(CCl)[C@@H](O)[C@H]3Cl)csc12]

and j) (2R,3S,4R,5S)-5-(4-aminothieno[3,2-d]pyrimidin-7-yl)-4-azido-2-(chloromethyl)-2-(hydroxymethyl)tetrahydrofuran-3-ol:

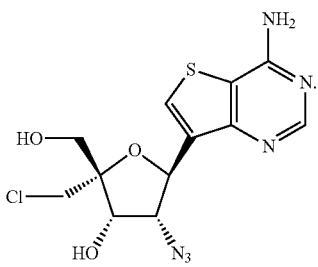 [SMILES: [N-]=[N+]=N[C@H]1[C@H](c2csc3c(N)ncnc23)O[C@@](CO)(CCl)[C@H]1O]

Antiviral Activity

Another aspect of the invention relates to methods of inhibiting viral infections, comprising the step of treating a sample or subject suspected of needing such inhibition with a composition of the invention.

Within the context of the invention samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as a tumor virus. Samples can be contained in any medium including water and organic solvent\water mixtures. Samples include living organisms such as humans, and manmade materials such as cell cultures.

If desired, the anti-viral activity of a compound of the invention after application of the composition can be observed by any method including direct and indirect methods of detecting such activity. Quantitative, qualitative, and semiquantitative methods of determining such activity are all contemplated. Typically one of the screening methods described above are applied, however, any other method such as observation of the physiological properties of a living organism are also applicable.

The antiviral activity of a compound of the invention can be measured using standard screening protocols that are known. For example, the antiviral activity of a compound can be measured using the following general protocols.

Respiratory Syncytial Virus (RSV) Antiviral Activity and Cytotoxicity Assays
Anti-RSV Activity Antiviral activity against RSV is determined using an infectious cytopathic cell protection assay in HEp-2 cells. In this assay, compounds inhibiting viral infection and/or replication produce a cytoprotective effect against the virus-induced cell killing that can be quantified using a cell viability reagent. The techniques used here are novel adaptations of methods described in published literature (Chapman et al., *Antimicrob Agents Chemother.* 2007, 51(9):3346-53.)

HEp-2 cells are obtained from ATCC (Manassas, Va.) and maintained in MEM media supplemented with 10% fetal bovine serum and penicillin/streptomycin. Cells are passaged twice a week and kept at subconfluent stage. Commercial stock of RSV strain A2 (Advanced Biotechnologies, Columbia, Md.) is titered before compound testing to determine the appropriate dilution of the virus stock that generates desirable cytopathic effect in HEp-2 cells.

For antiviral tests, HEp-2 cells are grown in large cell culture flasks to near confluency but not fully so. The compounds to be tested are prediluted in DMSO in 384-well compound dilution plates, either in an 8 or 40 sample per plate standardized dose response format. 3-fold serial dilution increments of each test compound are prepared in the plates and test samples are transferred via acoustic transfer apparatus (Echo, Labcyte) at 100 nl per well into cell culture assay 384-well plates. Each compound dilution is transferred in single or quadruplicate samples into dry assay plates, which are stored until assay is ready to go. The positive and negative controls are laid out in opposite on ends of the plate in vertical blocks (1 column).

Subsequently, an infectious mixture is prepared using an appropriate dilution of virus stock previously determined by titration with cells at a density of 50,000/ml and 20 uL/well is added to test plates w/compounds via automation (uFlow, Biotek). Each plate includes negative and positive controls (16 replicates each) to create 0% and 100% virus inhibition standards, respectively. Following the infection with RSV, testing plates are incubated for 4 days in a 37° C. cell culture incubator. After the incubation, a cell viability reagent, Cell TiterGlo (Promega, Madison, Wis.) is added to the assay plates, which are incubated briefly, and a luminescent readout is measured (Envision, Perkin Elmer) in all the assay plates. The RSV-induced cytopathic effect, percentage inhibition, is determined from the levels of remaining cell viability. These numbers are calculated for each tested concentration relative to the 0% and 100% inhibition controls, and the $EC_{50}$ value for each compound is determined by non-linear regression as a concentration inhibiting the RSV-induced cytopathic effect by 50%. Various potent anti-RSV tool compounds are used as positive controls for antiviral activity.

Cytotoxicity Assay in HEp-2 Cells

Cytotoxicity of tested compounds is determined in uninfected HEp-2 cells in parallel with the antiviral activity using the cell viability reagent in a similar fashion as described before for other cell types (Cihlar et al., *Antimicrob Agents Chemother.* 2008, 52(2):655-65.). The same protocol as for the determination of antiviral activity is used for the measurement of compound cytotoxicity except that the cells are not infected with RSV. Instead, an uninfected cell mixture at the same density is added at 20 ul/well to plates containing prediluted compounds, also at 100 nl/sample. Assay plates are then incubated for 4 days followed by a cell viability test using the same CellTiter Glo reagent addition and measurement of luminescent readouts. Untreated cell and cells treated at 2 uM puromycin (Sigma, St. Louis, Mo.) serve as 100% and 0% cell viability control, respectively. The percent of cell viability is calculated for each tested compound concentration relative to the 0% and 100% controls and the $CC_{50}$ value is determined by non-linear regression as a compound concentration reducing the cell viability by 50%.

Cytotoxicity Assay in MT-4 Cells

The MT-4 cell line was obtained from the NIH AIDS Research and Reference Reagent Program (Germantown, Md.) and cultured in RPMI-1640 medium (Irvine Scientific, Santa Ana, Calif., Cat #9160) supplemented with 10% FBS, 100 units/mL penicillin, 100 units/mL streptomycin, and 2 mM L-Glutamine. The MT-4 cells were passaged twice per week to maintain cell densities below $0.6 \times 10^6$ cells/mL. Complete RPMI-1640 media containing 100× concentrations of 3-fold serially diluted compound, ranging from 26 nM to 530 μM, were stamped in quadruplicate into black 384-well plates. After compound addition, $2 \times 10^3$ MT-4 cells were added to each well using a MicroFlo liquid dispenser (BioTek, Winooski, Vt.) and the cells were cultured for 5 days at 37° C. in a 5% $CO_2$ incubator. Following the incubation the cells were allowed to equilibrate to 25° C. and cell viability was determined by adding 25 μL of Cell-Titer Glo viability reagent. The mixture was incubated for 10 minutes at 25° C., and the luminescence signal was quantified on a Victor Luminescence plate reader. The $CC_{50}$ value is defined as the concentration of compound that reduces cell viability by 50% as determined by the Cell-Titer Glo signal. The data were analyzed using Pipeline Pilot Plate Data Analytics Collection software (Version 7.0, Accelrys, San Diego, Calif.). $CC_{50}$ values were calculated from a non-linear regression analysis using a 4-parameter sigmoidal dose-response equation: Y=Bottom+(Top−Bottom)/(1+10^[(Log CC50−X)*HillSlope]) where the Top and Bottom were fixed at 100% and 0% cell viability, respectively. $CC_{50}$ values were calculated as the average±standard deviation of 3 independent experiments.

| Example | $EC_{50}/\mu M$ | HEp-2 $CC_{50}/\mu M$ | MT-4 $CC_{50}/\mu M$ |
|---|---|---|---|
| 1 | 0.208 | >100 | 59 |
| 2 | 6.5 | >100 | >114 |
| 3 | 5.0 | >50 | >57 |
| 4 | >98 | >93 | 93 |
| PD1 | 0.556 | >50 | 10.4 |

RSV RNP Preparation

RSV ribonucleoprotein (RNP) complexes were prepared from a method modified from Mason et at (1). HEp-2 cells were plated at a density of $7.1 \times 10^4$ cells/cm² in MEM+10% fetal bovine serum (FBS) and allowed to attach overnight at 37° C. (5% $CO_2$). Following attachment, the cells were infected with RSV A2 (MOI=5) in 35 mL MEM+2% FBS. At 20 hours post-infection, the media was replaced with MEM+2% FBS supplemented with 2 μg/mL actinomycin D and returned to 37° C. for one hour. The cells were then washed once with PBS and treated with 35 mL of PBS+250 μg/mL lyso-lecithin for one minute, after which all liquid was aspirated. The cells were harvested by scrapping them into 1.2 mL of buffer A [50 mM TRIS acetate (pH 8.0), 100 mM potassium acetate, 1 mM DTT and 2 μg/mL actinomycin D] and lysed by repeated passage through an 18 gauge needle (10 times). The cell lysate was placed in ice for 10 minutes and then centrifuged at 2400g for 10 minutes at 4° C. The supernatant (S1) was removed and the pellet (P1) was disrupted in 600 uL of Buffer B [10 mM TRIS acetate (pH 8.0), 10 mM potassium acetate and 1.5 mM $MgCl_2$] supplemented with 1% Triton X-100 by repeated passage through an 18 gauge needle (10 times). The resuspended pellet was placed in ice for 10 minutes and then centrifuged at 2400g for 10 minutes at 4° C. The supernatant (S2) was removed and the pellet (P2) was disrupted in 600 uL of Buffer B supplemented with 0.5% deoxycholate and 0.1% Tween 40. The resuspended pellet was placed in ice for 10 minutes and then centrifuged at 2400g for 10 minutes at 4° C. The supernatant (S3) fraction, containing the enriched RSV RNP complexes, was collected and the protein concentration determined by UV absorbance at 280 nm. Aliquoted RSV RNP S3 fractions were stored at −80° C.

RSV RNP Assay

Transcription reactions contained 25 μg of crude RSV RNP complexes in 30 μL, of reaction buffer [50 mM TRIS-acetate (pH 8.0), 120 mM potassium acetate, 5% glycerol, 4.5 mM $MgCl_2$, 3 mM DTT, 2 mM ethyleneglycol-bis(2-aminoethylether)-tetraacetic acid (EGTA), 50 μg/mL BSA, 2.5 U RNasin (Promega), ATP, GTP, UTP, CTP and 1.5 uCi [α-$^{32}$P] NTP (3000 Ci/mmol)]. The radiolabed nucleotide used in the transcription assay was selected to match the nucleotide analog being evaluated for inhibition of RSV RNP transcription. Cold, competitive NTP was added at a final concentration of one-half its $K_m$ (ATP=20 μM, GTP=12.5 μM, UTP=6 μM and CTP=2 μM). The three remaining nucleotides were added at a final concentration of 100 μM.

To determine whether nucleotide analogs inhibited RSV RNP transcription, compounds were added using a 6 step serial dilution in 5-fold increments. Following a 90 minute incubation at 30° C., the RNP reactions were stopped with 350 μL of Qiagen RLT lysis buffer and the RNA was purified using a Qiagen RNeasy 96 kit. Purified RNA was denatured in RNA sample loading buffer (Sigma) at 65° C. for 10 minutes and run on a 1.2% agarose/MOPS gel containing 2M formaldehyde. The agarose gel was dried and exposed to a Storm phosphorimager screen and developed using a Storm phosphorimager (GE Healthcare). The concentration of compound that reduced total radiolabeled transcripts by 50% ($IC_{50}$) was calculated by non-linear regression analysis of two replicates.

REFERENCE

1) Mason, S., Lawetz, C., Gaudette, Y., Do, F., Scouten, E., Lagace, L., Simoneau, B. and Liuzzi, M. (2004) Polyadenylation-dependent screening assay for respiratory syncytial virus RNA transcriptase activity and identification of an inhibitor. Nucleic Acids Research, 32, 4758-4767.

| Example | $IC_{50}/\mu M$ |
|---|---|
| TP1 | 0.076 |
| TP2 | 0.042 |
| TP3 | 0.036 |
| TP4 | 0.2 |

What is claimed is:

1. A compound of Formula (III), or a pharmaceutically acceptable salt thereof:

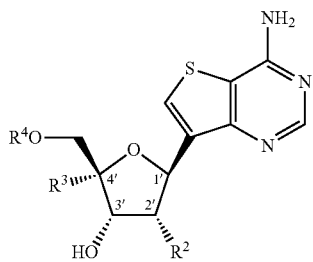
(III)

wherein:
R² is F, Cl, OH, NH₂, CN, and N₃;
R³ is selected from the group of CN, N₃, methyl, ethyl, propyl, vinyl, propenyl, ethynyl, CH₂F, CHF₂, CH₂Cl, CH₂SMe, and CH₂OMe; and
R⁴ is H or group of the formula:

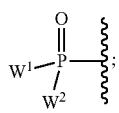

wherein W¹ and W² are each, independently, OH or a group of the Formula Ia:

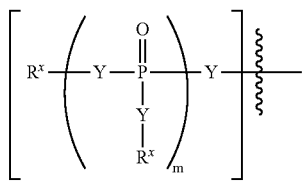
Formula Ia wherein:
each Y is independently a bond or O;
m is 0, 1, 2, or 3;
each R$^x$ is H, halogen or OH;
or
R⁴ is selected from H and:

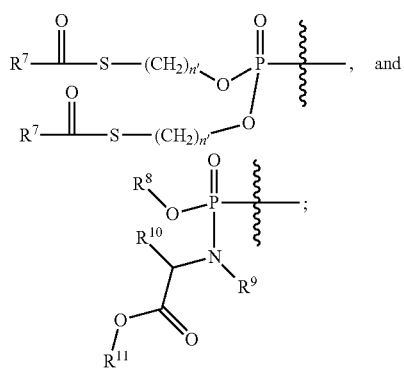

wherein:
n' is selected from 1, 2, 3, and 4;
R⁷ is selected from C₁-C₈ alkyl, —O—C₁-C₈ alkyl, benzyl, —O-benzyl, —CH₂—C₃-C₆ cycloalkyl, —O—CH₂—C₃-C₆ cycloalkyl, and CF₃;
R⁸ is selected from phenyl, 1-naphthyl, 2-naphthyl,

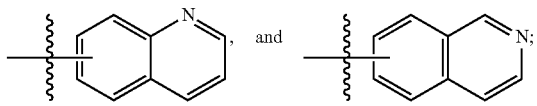

R⁹ is selected from H and CH₃;
R¹⁰ is selected from H or C₁-C₆ alkyl;
R¹¹ is selected from H, C₁-C₈ alkyl, benzyl, C₃-C₆ cycloalkyl, and —CH₂—C₃-C₆ cycloalkyl.

2. A compound of Formula (IX):

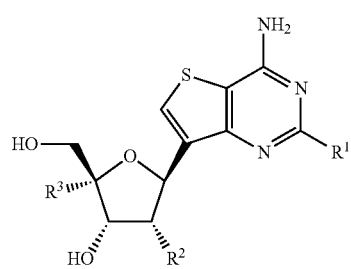
(IX)

wherein:
R¹ is selected from the group of H, CH₃, F, Cl, and NH₂;
R² is selected from the group of F, Cl, OH, NH₂, CN, and N₃; and
R³ is selected from the group of CN, N₃, methyl, ethyl, propyl, vinyl, propenyl, ethynyl, CH₂F, CHF₂, CH₂Cl, CH₂SMe, and CH₂OMe;
or a pharmaceutically acceptable salt thereof.

3. A compound of claim 2, or a pharmaceutically acceptable salt thereof, wherein R¹ is H.

4. A compound of claim 2, or a pharmaceutically acceptable salt thereof, wherein R¹ is F.

5. A compound of claim 2, or a pharmaceutically acceptable salt thereof, wherein R² is F.

6. A compound of claim 2, or a pharmaceutically acceptable salt thereof, wherein R² is Cl.

7. A compound of claim 2, or a pharmaceutically acceptable salt thereof, wherein R² is N₃.

8. A compound of claim 2, or a pharmaceutically acceptable salt thereof, wherein R³ is selected from the group of CN and N₃.

9. A compound of claim 2, or a pharmaceutically acceptable salt thereof, wherein R³ is selected from the group of methyl, ethyl, and propyl.

10. A compound of claim 2, or a pharmaceutically acceptable salt thereof, wherein R³ is selected from the group of CH₂F, CHF₂, and CH₂Cl.

11. A compound of claim 1, or a pharmaceutically acceptable salt thereof, wherein R⁴ is selected from the group of:

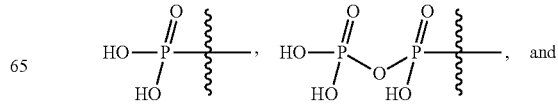

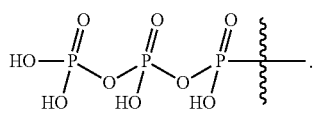

12. A compound of claim 1, or a pharmaceutically acceptable salt thereof, wherein $R^4$ is:

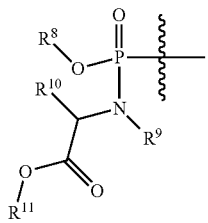

wherein $R^8$, $R^9$, $R^{10}$, and $R^{11}$ are as defined in claim 1.

13. A compound of claim 1, or a pharmaceutically acceptable salt thereof, wherein $R^4$ is:

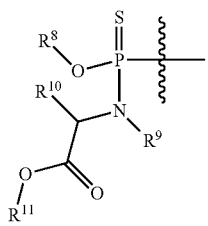

wherein $R^8$, $R^9$, $R^{10}$, and $R^{11}$ are as defined in claim 1.

14. A compound of claim 1, or a pharmaceutically acceptable salt thereof, wherein $R^4$ is:

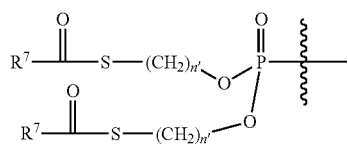

wherein n' is selected from 1, 2, 3, and 4; and $R^7$ is selected from the group of $C_1$-$C_8$ alkyl, —O—$C_1$-$C_8$ alkyl, benzyl, —O-benzyl, —$CH_2$—$C_3$-$C_6$ cycloalkyl, —O—$CH_2$—$C_3$-$C_6$ cycloalkyl, and $CF_3$.

15. A compound, or a pharmaceutically acceptable salt thereof, selected from the group of:

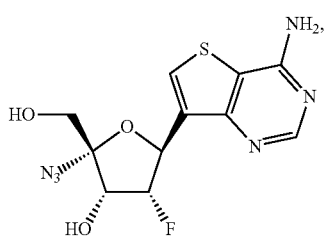
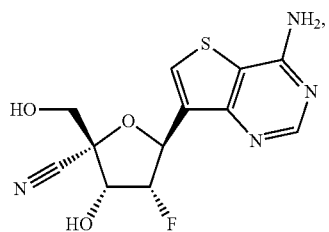
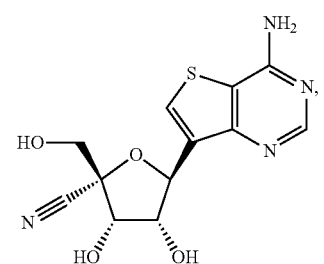
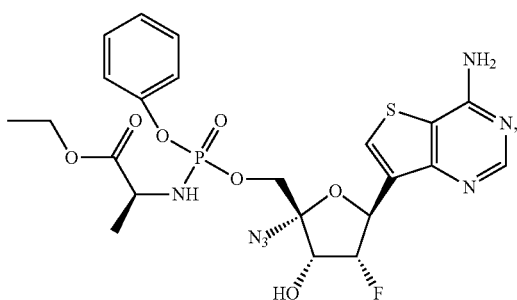
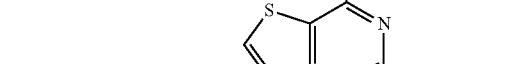

-continued

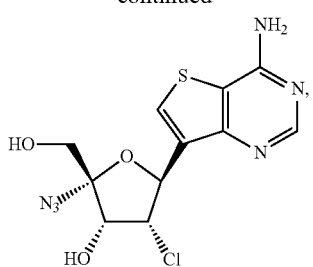

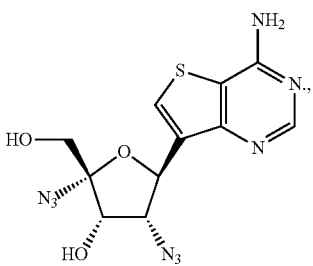

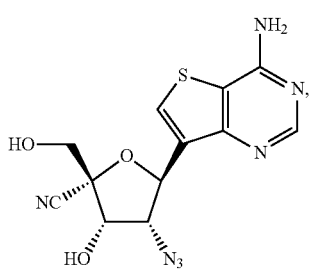

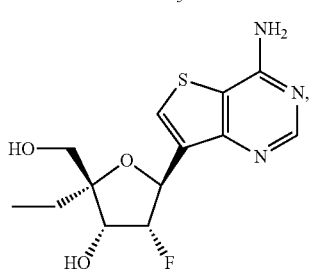

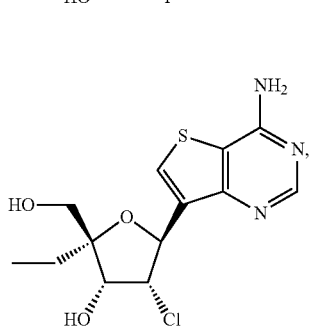

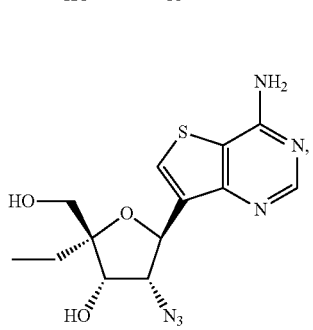

-continued

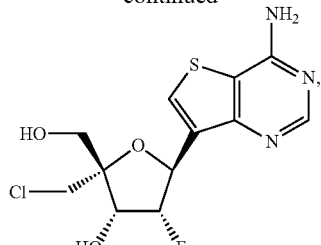

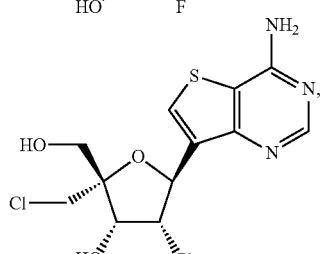

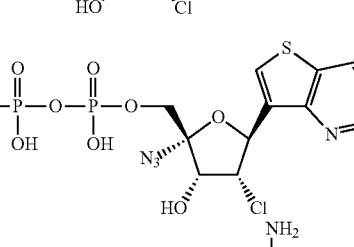

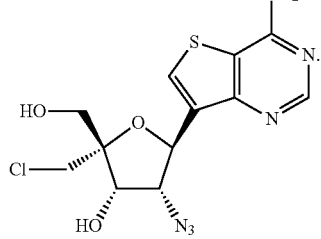

16. A method of treating Pneumovirinae virus infection in a human in need thereof, the method comprising administering to the human in need thereof a therapeutically effective amount of a compound of claim 1, or a pharmaceutically acceptable salt thereof.

17. The method of claim 16 wherein the Pneumovirinae virus infection is a respiratory syncytial virus infection.

18. A pharmaceutical composition comprising a compound of claim 1, or a pharmaceutically acceptable salt thereof, and a pharmaceutically acceptable carrier or excipient.

19. A pharmaceutical composition comprising a compound of claim 2, or a pharmaceutically acceptable salt thereof, and a pharmaceutically acceptable carrier or excipient.

20. A pharmaceutical composition comprising a compound of claim 8, or a pharmaceutically acceptable salt thereof, and a pharmaceutically acceptable carrier or excipient.

21. A pharmaceutical composition comprising a compound of claim 9, or a pharmaceutically acceptable salt thereof, and a pharmaceutically acceptable carrier or excipient.

22. A pharmaceutical composition comprising a compound of claim 15, or a pharmaceutically acceptable salt thereof, and a pharmaceutically acceptable carrier or excipient.

23. A method of treating Pneumovirinae virus infection in a human in need thereof, the method comprising administering to the human in need thereof a therapeutically effective amount of a compound of claim 2, or a pharmaceutically acceptable salt thereof.

24. The method of claim 23 wherein the Pneumovirinae virus infection is a respiratory syncytial virus infection.

25. A method of treating Pneumovirinae virus infection in a human in need thereof, the method comprising administering to the human in need thereof a therapeutically effective amount of a compound of claim 8, or a pharmaceutically acceptable salt thereof.

26. The method of claim 25 wherein the Pneumovirinae virus infection is a respiratory syncytial virus infection.

27. A method of treating Pneumovirinae virus infection in a human in need thereof, the method comprising administering to the human in need thereof a therapeutically effective amount of a compound of claim 15, or a pharmaceutically acceptable salt thereof.

28. The method of claim 27 wherein the Pneumovirinae virus infection is a respiratory syncytial virus infection.

\* \* \* \* \*